US006268393B1

(12) United States Patent
Xu et al.

(10) Patent No.: US 6,268,393 B1
(45) Date of Patent: Jul. 31, 2001

(54) METHOD FOR TREATING AND PREVENTING MYCOBACTERIUM INFECTIONS

(75) Inventors: Ze-Qi Xu; Yuh Meei Lin, both of Naperville; Michael T. Flavin, Darien, all of IL (US)

(73) Assignee: Sarawak Medichem Pharmaceuticals, Lemont, IL (US)

( * ) Notice: Subject to any disclaimer, the term of this patent is extended or adjusted under 35 U.S.C. 154(b) by 0 days.

(21) Appl. No.: 09/417,672

(22) Filed: Oct. 14, 1999

Related U.S. Application Data

(60) Provisional application No. 60/104,409, filed on Oct. 15, 1998.

(51) Int. Cl.$^7$ .................................................. A61K 31/353
(52) U.S. Cl. ............................................................ 514/453
(58) Field of Search ............................................. 514/453

(56) References Cited

U.S. PATENT DOCUMENTS

| 5,591,770 | 1/1997 | Boyd et al. | 514/453 |
| 5,723,631 | 3/1998 | Patil et al. | 549/277 |
| 5,859,049 | 1/1999 | Boyd et al. | 514/453 |

FOREIGN PATENT DOCUMENTS 0 699 202 B1    3/1999  (EP).

OTHER PUBLICATIONS

Bernstein, et al., "Chemotherapy of Experimental Tuberculosis," The American Review of Tuberculosis, vol. 65 [4], Apr. (1952), pp. 357–365.
Boyer, et al., Analysis of Nonnucleoside Drug–Resistant Variants of Human Immunodeficiency Virus Type 1 Reverse Transcriptase, Journal of Virology, vol. 67 [4], Apr. (1993), pp. 2412–2420.
Cole, et al., "Deciphering the biology of *Mycobacterium tuberculosis* from the complete genome sequence," Nature, vol. 393, (1998), pp. 537–544.
Currens, et al., "Antiviral Activity and Mechanism of Action of Calanolide A Against the Human Immunodeficiency Virus Type–1," Journal of Pharmacology and Experiemental Therapeutics, vol. 279 [2], (1998), pp. 645–651.
Davidson, et al., "Isoniazid Inhibition of the Synthesis of Monounsaturated Long–Chain Fatty Acids in *Mycobacterium tuberculosis* H37Ra," Antimicrobial Agents and Chemotherapy, vol. 16 [1], (1979), pp. 104–105.
Dessen, et al., "Crystal Structure and Function of the Isoniazid Target of *Mycobacterium tuberculosis*," Science, vol. 267, (1995), pp. 1638–1641.
Flavin, et al., "Synthesis, Chromatorgraphic Resolution, and Anti–Human Immunodeficiency Virus Activity of (±)–Calanolide A and Its Enantiomers," J. Med. Chem, vol. 39, (1996), pp. 1303–1313.

Frieden, M.D., et al., "The Emergence of Drug–Resistant Tuberculosis in New York City," New England Journal of Medicine, vol. 328 [8], (1993), pp. 521–526.
Fox, H., "The Chemical Approach to the Control of Tuberculosis," Science, vol. 116, (1952), pp. 129–134.
Herzog, H., "History of Tuberculosis," Respiration, vol. 65, (1998), pp. 5–15.
Heym, et al., "Implications of Multidrug Resistance for the Future of Short–course Chemotherapy of Tuberculosis: a Molecular Study," The Lancet, vol. 344, (1994), pp. 293–298.
Johnson, et al., "Mechanistic Studies of the Oxidation of Isoniazid by the Catalase Peroxidase from *Mycobacterium Tuberculosis*," Journal of the American Chemical Society, vol. 116 [16], (1994), pp. 7425–7426.
Khilevich, et al., "Synthesis Of (+)–Calanolide A, An Anti–Hiv Agent, Via Enzyme–Catalyzed Resolution Of The Aldol Products," Tetrahedron: Asymmetry, vol. 7 [11], (1996), pp. 3315–3326.
Konno, et al., "Pyrazinamide Susceptibility and Amidase Activity of Tubercle Bacili," Am. Rev. Respir. Dis., vol. 95, (1967), pp. 461–469.
Kucherenko, et al., "Novel Approach for Synthesis of (±)–Calanolide A and Its Anti–HIV Activity," Tetrahedron Letters, vol. 36 [31], (1995), pp. 5475–5478.
Levin, et al., "*Mycobacterium smegmatis* RNA polymerase: DNA supercoiling, action of rifampicin and mechanism of rifampicin resistance," Molecular Microbiology, vol. 2 [2], (1993), pp. 277–285.
Marttila, et al., "katG Mutations in Isoniazid–Resistant *Mycobacterium tuberculosis* Isolates Recovered from Finnish Patients," Antimicrobial Agents and Chemotherapy, vol. 40 [9], (1996), pp. 2187–2189.
Mdluli, et al., "Inhibition of a *Mycobacterium tuberculosis* β–Ketoacyl ACP Synthase by Isoniazid," Science, vol. 280, (1998), pp. 1607–1610.
Mdluli, et al., "Biochemical and Genetic Data Suggest that InhA Is Not the Primary Target for Activated Isoniazid in *Mycobacterium tuberculosis*," The Journal of Infectious Diseases, vol. 174, (1996), pp. 1085–1090.
Middlebrook, G., "Sterilization of Tubercle Bacilli by Isonicotinic Acid Hydrazide* and the Incidence of Variants Resistant to the Drug in Vitro," Am. Rev. Tuberc., vol. 65, (1952), pp. 765–767.
Mitchison, D. A., "Understanding the chemotherapy of tuberculosis—current problems," Journal of Antimicrobial Chemotherapy, vol. 29 (1992), pp. 477–493.

(List continued on next page.)

*Primary Examiner*—Phyllis G. Spivack
(74) *Attorney, Agent, or Firm*—McDonnell Boehnen Hulbert & Berghoff

(57) ABSTRACT

Calanolides and analogues thereof that demonstrate potent mycobacterium activity are provided. Also provided is a method of using calanolides and analogues thereof for treating or preventing mycobacterium infections. The calanolides and analogues thereof provided are obtained via syntheses employing chromene 4 and chromanone 7 as key intermediates.

18 Claims, 1 Drawing Sheet

OTHER PUBLICATIONS

Mitchison, D.A., "Pyrazinamide—on the antituberculosis drug frontiline," Nature Medicine, vol. 2 [6], (1996), pp. 635–636.

Morris, et al., "Molecular Mechanisms of Multiple Drug Resistance in Clinical Isolates of *Mycobacterium tuberculosis,*" Journal of Infectious Diseases, vol. 171, (1995), pp. 954–960.

Musser, et al., "Characterization of the Catalase–Peroxidase Gene (katG) and inhA Locus in Isoniazid–Resistant and – Susceptible Strains of *Mycobacterium tuberculosis* by Automated DNA Sequencing: Restricted Array of Mutations Associated with Drug Resistance," Journal of Infectious Diseases, vol. 173, (1996), pp. 196–202.

Nivin, et al., "A Continuing Outbreak of Multidrug–Resistant Tuberculosis, with Transmission in a Hospital Nursery," Clinical Infectious Diseases, vol. 26, (1998), pp. 303–307.

Özdemir, et al., "Tuberculosis Remains an Important Factor in the Morbidity and Mortality of Hemodialysis Patients," Transplantation Proceedings, vol. 30, (1998), pp. 846–847.

Pablos–Mendez, et al., "Global Surveillance for Antituberculosis–Drug Resistance," New England Journal of Medicine, vol. 338 [23], (1998), pp. 1641–1649.

Pansy, et al., "In Vitro Studies on Isonicotinic Acid Hydrazide," The Squibb Institute for Medical Research, (1952), pp. 761–764.

Perriëns, et al., "Increased Mortality and Tuberculosis Treatment Failure Rate among Human Immunodeficiency Virus (HIV) Seropositive Compared with HIV Seronegative Patients with Pulmonary Tuberculosis Treated with "Standard" Chemotherapy in Kinshasa, Zaire," Am. Rev. Respir. Dis, vol. 144, (1991), pp. 750–755.

Quémard, et al., "Enzymatic Characterization of the Target for Isoniazid in Mycobacterium," Biochemistry, vol. 34, (1995), pp. 8235–8241.

Raviglione, et al., "Global Epidemiology of Tuberculosis," JAMA, vol. 273 [3], (1995), pp. 220–226.

Robitzek, et al., "Hydrazine Derivatives of Isonicotinic Acid (Rimifon, Marsilid) in the Treatment of Active Progressive Caseous–Pneumonic Tuberculosis," Am. Ref. Tuberc., vol. 65, (1952), pp. 402–428.

Scorpio, et al., "Mutations in pncA, a gene encoding pyrazinamidase/nicotinamidase, cause resistance to the antituberculous drug pyrazinamide in tubercle bacillus," Nature Medicine, vol. 2 [6], (1996), pp. 662–667.

Snider, et al., "The New Tuberculosis," The New England Journal of Medicine, vol. 36 [10], (1992), pp. 703–705.

Takayama, et al., "Inhibition by Ethambutol of Mycolic Acid Transfer into the Cell Wall of *Mycobacterium smegmatis,*" Antimicrobial Agents and Chemotherapy, vol. 16 [2], (1979), pp. 240–242.

Winder, et al, "Inhibition by Isoniazid of Synthesis of Mycolic Acids in *Mycobacterium tuberculosis,*" Journal of General Microbiology, vol. 63, (1970), pp. 41–48.

Zhang, et al, "The catalase–peroxidase gene and isoniazid resistance of *Mycobacterium tuberculosis,*" Nature, vol. 358, (1992), pp. 591–593.

Collins, et al., "Microplate Alamar Blue Assay versus BACTEC 460 System for High–Throughput Screening of Compounds against *Mycobacterium tuberculosis* and *Mycobacterium avium,*" Antimicrobial Agents and Chemotherapy, vol. 41 [5], (1997), pp. 1004–1009.

Creagh, Ph.D., et al., "Preliminary Clinical Safety Profile (+)–Calanolide A—A New Novel NNRTI," $5^{th}$ Conference on Retroviruses and Opportunistic Infections, Jan. 22–26, 1997, Abstract 477.

Frank, et al., "Safety Assessment of (+)–Calanolide A, A Naturally Occurring Anti–HIV Agent," $4^{th}$ Conference on Retroviruses and Opportunistic Infections, Jan. 22–26, 1997, Abstract No. 225.

Inderlied, et al., "Antimycobacterial Agents and Susceptibility Tests," Manual of Clinical Microbiology, $6^{th}$ Ed., (1995), pp. 1601–1623.

Johnsson, et al., "Studies on the Mechanism of Action of Isoniazid and Ethionamide in the Chemotherapy of Tuberculosis," J. Am. Chem. Soc., vol. 117, (1995), pp. 5009–5010.

Kucherenko, et al., "Novel Approach for Synthesis of (±)–Calanolide A and Its Anti–HIV Activity," Tetrahedron Letters, vol. 36, No. 31, (1995), pp. 5475–5478.

Ormerod, "Rifampicin and isoniazid prophylactic chemotherapy for tuberculosis," Arch. Dis. Child, vol. 78, (1998), pp. 169–171.

Rahman, et al., "Anti–tuberculosis Activity of Quassinoids," Chem. Pharm. Bull., vol. 45 [9], (1997), pp. 1527–1529.

Winder, et al., "Inhibition by Isoniazid of Synthesis of Mycolic Acids in *Mycobacterium tuberculosis,*" Journal of General Microbiology, vol. 63, (1970), pp. 41–48.

Soulatrolide (−)-Calanolide B
or
Costatolide 7,8-Dihydrosoulatrolide (+)-*trans*-Ketone (±)-*trans*-Ketone (±)-*cis*-Ketone (±)-*trans*-7,8-Dihydroketone

METHOD FOR TREATING AND PREVENTING MYCOBACTERIUM INFECTIONS

This application is a continuation-in-part of provisional application Ser. No. 60/104,409, filed Oct. 15, 1998.

FIELD OF INVENTION

The present invention relates to a method and composition for treating and/or preventing mycobacterium infections in patients.

BACKGROUND OF INVENTION

Infectious diseases remain the largest cause of death in the world today, greater than cardiovascular disease or cancer.[1] Among infectious diseases, tuberculosis (TB) is the leading cause of death.[2] The emergence of multidrug-resistant (MDR) strains and the global human immunodeficiency virus (HIV) pandemic amplify the incidence of TB.

Tuberculosis mainly affects the lungs but can also involve other organs. TB strikes people of all ages but is more common among the elderly. The disease can also afflict animals, especially livestock such as cattle, hogs, and poultry. Rod-shaped bacteria, tubercle bacilli discovered by the German physician Robert Koch in 1882, cause the disease. Tubercle bacilli belong to a genus of bacteria called Mycobacterium. This disease once ranked among the most common causes of death in the world. Today, improved methods of prevention, detection, diagnosis, and treatment have greatly reduced both the number of people who contract the disease and the number of people who die from it. However, in the last decade, the outbreaks of MDR tuberculosis (MDRTB) and TB amplified by the global HIV pandemic make TB an urgent global issue.

One-third of the world's population is infected with *Mycobacterium tuberculosis* (Mtb),[3] a facultative intracellular bacillus. After infection with Mtb, the lifetime risk of developing TB is approximately 10%, while 90% of infected persons have latent infection with viable bacilli. This 10% rate of TB accounts for the 8 million persons reported annually with active TB, and the resultant 3 million deaths. Moreover, TB is a serious problem faced by hemodialysis patients,[4] and TB is the No. 1 killer of women of childbearing age around the world with 1.2 million women dying of the disease in 1997 according to reports by the World Health Organization.[11a]

a. Tuberculosis and AIDS

TB infection is a serious problem for acquired immunodeficiency syndrome (AIDS) patients. HIV-infected individuals are particularly susceptible to infection with Mtb and the development of TB. Compared to an individual who is not infected with HIV, an individual infected with HIV has a 10 times greater risk of developing TB. In an individual infected with HWV, the presence of other infections, including TB, may allow HIV to multiply more quickly. This may result in more rapid progression of HIV infection and AIDS.5 As HIV infection progresses, CD4+ lymphocytes decline in number and function. The immune system is less able to prevent the growth and local spread of Mtb. Even in HIV-infected patients, pulmonary TB (PTB) is still the most common form of TB. The presentation depends on the degree of immunosuppression.

As in adults, the natural history of TB in a child infected with HIV depends on the stage of HIV disease. Early in HIV infection, when immunity is strong, the signs of TB are similar to those in a child without HIV infection. As HIV infection progresses and immunity declines, dissemination of TB becomes more commnon. Tuberculous meningitis, miliary tuberculosis, and widespread tuberculous lymphadenopathy occur.

HIV-positive patients and staff in health units face daily exposure to TB. The risk of exposure is greatest in adult medical wards and TB wards where there are many PTB cases. From 1990–1992, the Centers for Disease Control and prevention (CDC) investigated outbreaks of multidrug-resistant tuberculosis (MDRTB) in several hospitals and a state correctional system. Almost 300 cases of MDRTB were identified in these outbreaks; most patients were HIV-seropositive. The mortality rate was 80%–90% and the median interval from diagnosis of tuberculosis to death ranged from 4–16 weeks.[6] In 1995, about one third of the 17 million HIVnfected people worldwide were also co-infected with Mtb.[5] (TB is the leading cause of death in AIDS patients).

b. Treatment of TB

Isoniazid (isonicotinic acid hydrazide) (INH) was first reported to be effective against Mtb and *M. bovis* in 1952.[7–9] Isoniazid, now still a front-line therapy against TB, has been shown to be an effective prophylactic antitubercular[10], and modern short-course chemotherapy is initiated with three drugs: isoniazid, rifampin and pyrazinamide (PZA), often with the inclusion of a fourth drug, usually ethambutol. Recently, rifapentine, a derivative of rifamycin, was approved by the FDA for the treatment of tuberculosis. [11b]

The American Thoracic Society and the CDC in the United States now recommend a treatment regimen of isoniazid, rifampin, and pyrazinamide for 2 months, followed by isoniazid and rifampin for an additional 4 months, as the standard 6-month regime. Isoniazid, cheap and safe, has a wide therapeutic margin and high early bactericidal activity so that it kills rapidly growing bacilli in lesions, but is inefficient in ultimately sterilizing these lesions. Rifampin and PZA are crucial in achieving sterilization by killing persisting semi-dormant bacilli, and are thus responsible for shortening the duration of treatment from the earlier norm of 12–18 months to the current standard of 6 months.[12] However, many people fail to complete the lengthy therapy, treatment failures are high, and MDR is increasing. A 4-year study, led by the World Health Organization, shows that of people who had been treated for TB for less than a month, 36 percent harbored microbes that resisted at least one of the four main anti-tuberculosis drugs. Moreover, 10% of infected people who had never been treated for the disease carried a strain of Mtb that resisted at least one drug.[13]

d. Mechanism of Drug Action

Isoniazid is a prodrug that requires activation by the mycobacterial catalase-peroxidase enzyme (KatG) to an active form that then exerts a lethal effect on an intracellular target or targets.[14–16] The lethal effect lies in the biosynthetic pathway for mycolic acids,[14, 17–19] alpha-branched and beta-hydroxylated fatty acids found in the envelope of mycobacteria.

Rifamycins (e.g. rifampin, rifabutin and rifapentine) are potent inhibitors of prokaryotic DNA-dependent RNA polymerase,[20] with little activity against the equivalent mammalian enzymes. This group of antimicrobial agents are compounds composed of aromatic rings linked by an aliphatic bridge. Most likely, the lipophilic properties of the molecule are important for the binding of the drug to the polymerase and aid in the penetration of the drug across the mycobacterial cell wall.

Pyrazinamide (PZA) is a synthetic derivative (pyrazine analog) of nicotinamide and in combination with isoniazid is rapidly bactericidal for replicating forms of Mtb, with an average MIC of 20 µg/mL. The activity of PZA depends on the presence of a bacterial amidase which converts PZA to pyrazinoid acid (PZOA), the active antibacterial molecule.[21] Amidase activity is present in PZA-sensitive but not in PZA-resistant species such as M. bovis, opportunistic mycobacteria and Mtb resistant to PZA as a result of drug therapy. The gene (pncA) encoding the PZA (and nicotinamide) amidase which is responsible for processing PZA into its bactericidal form has been identified, and the mutations in pncA that confer PZA resistance to tubercle bacilli have been recently reported.[22]

Ethambutol is active against Mtb, with MICs in the range of 1 to 5 µg/mL. The drug has much more variable activity against the other species of slowly growing mycobacteria and is significantly less active against rapidly growing mycobacteria. On the whole, ethambutol is inactive against other microorganisms. The mechanisms of action of ethambutol have focused on two targets: polyamine function and metabolism and cell wall synthesis. Ethambutol inhibits the transfer of mycolic acid into the cell wall and stimulates trehalose dimycolate synthesis.[23]

e. Multidrug Resistance

The importance of KatG mutations in isoniazid resistance is well established, although the extent to which such mutations account for the spectrum of resistance observed in clinical isolates is arguable.[24] Best estimates indicate that >50% of isoniazid-resistant clinical isolates are KatG mutants.[25]

Mycobacteria have a similar enzyme, InhA, required for mycolic acid biosynthesis.[26] A genetic approach revealed that InhA appeared to finction as a component of a type II fatty acid synthase system responsible for the final reduction step in chain elongation to form conventional fatty acids.[27-28] Sequencing of clinical isolates of Mtb has revealed mutations in putative regulatory regions upstream of the InhA gene and potential coding sequence mutations that may be directly involved in isoniazid resistance, but these occur only in a subpopulation of isoniazid-resistant, wild-type catalase-peroxidase isolates.[24-25, 29-31] Thus, although the InhA protein may be involved in isoniazid-resistance, it probably does not represent the target whose inhibition results in hexacosanoic acid accumulation, and mutations in InhA and KatG do not appear to be sufficient to account for all of the observed resistance.[32] Recently, a protein species purified from INH-treated Mtb was shown to consist of a covalent complex of isoniazid, 12-kilodalton acyl carrier protein (AcpM), and a beta-ketoacyl acyl carrier protein synthase, KasA. Amino acid-altering mutations in the KasA protein were identified in isoniazid-resistant patient isolates that lacked other mutations associated with resistance to this drug.[33]

Most recently, the complete genome sequence of the best-characterized strain of Mtb, H37Rv, has been determined and analyzed.[34] This will improve our understanding of the biology of this slow-growing pathogen and to help in the conception of new prophylactic and therapeutic interventions.

f. The Significance of the Recent TB Revival

Worldwide, the recorded number of new cases of TB correlates with economic conditions, the highest incidence being seen in Africa, Asia, and Latin America. In the industrialized nations, including Europe, the steady drop in TB incidence began to level off in the mid-1980s and then stagnated or even reversed somewhat. Much of this rise can be attributed to an influx of migrants from countries with a higher incidence of TB.[35]

Another element in this rising trend is HIV. The particular susceptibility and increased mortality of the disease among individuals infected with HIV pose a serious threat to TB control programs.[36] Moreover, the emergence of multidrug-resistant strains of M. tuberculosis (MDR-Mtb) has resulted in fatal outbreaks in many countries, including the United States.[37] Strains of MDR-Mtb, some of which are resistant to as many as seven drugs, are deadly to both HIV negative and HIV positive individuals.[38] The occurrence of MDRTB in patients with AIDS has led to significant changes in the management of tuberculosis in these patients, compared with tuberculosis in patients without AIDS.

g. Prophylactic Treatment

The prophylactic treatment of children with strongly positive tuberculin test by isoniazid and rifampicin has brought a marked reduction in the incidence of pediatric TB in high incidence geographic areas.[39] Controlled clinical studies have shown that isoniazid preventive treatment reduces the risk of TB disease in HIV-positive individuals also infected with Mtb.[6] Since (+)-calanolide A might be used in the clinic as an anti-AIDS drug in the near future, it might demonstrate a prophylactic and therapeutic effect on TB for AIDS patients when used in AIDS treatment.

SUMMARY OF THE INVENTION

The present invention relates to a composition and method for treating and/or preventing mycobacterium infections, especially tuberculosis infections, in patients. The method is useful for treating or preventing mycobacterium infections in immuno-comprised patients, particularly HIV infected patients.

Accordingly, one object of the invention is a method for treating or preventing mycobacteriun infection in a patient comprising administering an anti-mycobacterium effective amount of calanolide or analogues thereof. Representative mycobacterial organisms include *Mycobacterium avium* complex (MAC), *Mycobacterium kansaii*, *Mycobacterium marinum*, *Mycobacterium phlei*, *Mycobacterium ulcerans*, *Mycobacterium xenopi*, *Mycobacterium gordonae*, *Mycobacterium terrae* complex, *Mycobacterium haemophilum*, *Mycobacterium fortuitum*, *Mycobacterium tuberculosis*, *Mycobacterium laprae*, *Mycobacterium scrofulaceum* and *Mycobacterium smegmatis*.

Another object of the invention is to provide an anti-mycobacterium composition comprising calanolide or analogues thereof, particularly (+)-calanolide A, (−)-calanolide A, (−) calanolide B (also called costatolide), (±)-calanolide A, soulattrolide, and (−)-7,8-dihydro-soulattrolide. The Applicants discovered the anti-tuberculosis activity of these compounds, especially (+)-calanolide A and (−)-calanolide A, which demonstrated inhibitory activity against Mtb H37Rv in BACTEC 12B medium using the BACTEC 460 radiometric system with 96% and 98% inhibition, respectively, at a concentration of 12.5 µg/mL. The actual minimum inhibitory concentration (MIC) for (+)-calanolide A, defined as the lowest concentration inhibiting 99% of the inoculum, was 8 µM (3.13 µg/mL). The anti-mycobacterium composition may include one or more other pharmaceutically active agents such as anti-viral agents.

The present invention provides calanolide analogues obtained via syntheses employing chromene 4 and chromanone 7 as key intermediates, which is described in U.S. patent application Ser. Nos. 09/173,143, filed Oct. 15, 1998; 08/609,537, filed Mar. 1, 1996; and No. 08/510,213, filed Aug. 2, 1995, as well as U.S. Pat. No. 5,489,697, issued Feb. 6, 1996. herein incorporated by reference in its entirety.

Chromene 4 is synthesized by the sequence depicted in Scheme I. Thus, 5,7dihydroxy-4propylcoumarin, 2,[55] was prepared quantitatively from ethyl butyrylacetate and phloroglucinol under Pechmann conditions.[56] Product yield and purity were dependent on the amount of sulfuric acid used. The 8-position of 5,7-dihydroxy4-propylcounarin, 2, was then selectively acylated at 8–10° C. by propionyl chloride and $AlCl_3$ in a mixture of carbon disulfide and nitrobenzene to afford 5,7-dihydroxy-8-propionyl-4-propylcoumarin, 3.

In an alternative and preferred reaction, coumarin intermediate 3 may be produced in large scale quantities and with minimal formation of undesirable 6-position acylated product and 6,8-bis-acylated product by selective acylation of 5,7-dihydroxy-4-propylcoumarin 2 with a mixture of propionic anhydride and $AlCl_3$ at about 70–75° C.

The chromene ring was introduced upon treatment of compound 3 with 4,4-dimethoxy-2-methylbutan-2-ol, providing 4 in 78% yield (Scheme I). Chlorotitanium-mediated aldol reaction of chromene 4 with acetaldehyde led to formation of (±)-8a and (±)8b in a ratio of 95:5. The racemic syn aldol product [(±)-8a] was resolved by enzyme-catalyzed acylation. Thus, in the presence of lipase and vinyl acetate, (−)-8a was selectively acylated and the desired enantiomer (+)-8a was unreacted. The purified (+)-8a was subjected to a Mitsunobu[57a–d] reaction, exclusively leading to (+)-trans-chromanone [(+)-7].

Finally, Luche reduction [58] on (+)-7 led to formation of (+)-calanolide A [(+)-1] which contained 10% of (+)-calanolide B (see Scheme III). (+)-Calanolide A[(+)-1] was further separated from (+)-calanolide B by preparative normal phase HPLC and was identical with an authentic sample.

If desired, the racemic anti aldol product [(±)-8b] may also be resolved by enzyme-catalyzed acylation into (+)-8b and the ester 10 from (−)-8b (Scheme IV). Mitsunobu reaction ion (+)-8b would lead to formation of the cis-chromanone 7a which could then be reduced to produce calanolide C.

The synthetic sequence for (+)-calanolide A was extended to the synthesis of calanolide analogues. Thus, Pechmann reaction of phloroglucinol with various β-ketoesters yields substituted 5,7-dihydroxycoumarin 11 (Scheme V). Friedel-Crafts acylation of substituted 5,7-dihydroxycoumarin 11 leads to formation of 8-acylated 5,7-dihydroxycoumarin 12. Chromenylation of 12 can be achieved by reacting with substituted β-hydroxyaldehyde dimethylacetal, affording chromenocoumarin 13. Aldol reaction of chromenocoumarin 13 with carbonyl compounds in the presence of LDA with or without metal complexing agents forms the racemic aldol product (±)-14. Cyclization of (±)-14 under Mitsunobu conditions, by using triphenylphosphine and diethyl azodicarboxylate (DEAD), leads to formation of chromanone analogue (±)-15. Reduction of (±)-15 with sodiun borohydride with or without cerium chloride yields the 12-hydroxy analogue (±)-16 (Scheme V).

Catalytic hydrogenation of both (±)-15 and (±)-16 produces 7,8-dihydro derivatives (±)-17 and (±)-18 (Scheme VI). Treatment of (±)-15 with hydroxylamine or alkoxyamine affords oxime derivatives (±)-19 (Scheme VI). Reduction of (±)-19 under different conditions [59] should selectively yield hydroxylamino or amino compounds (20 and 21).

Optically active forms of 14–21 would be obtained by employing enzymatic acylation, as described in Scheme III for (+)-calanolide A[(+)-1]. Thus, enzyme-catalyzed acylation of the racemic aldol product (±)-14 would selectively acylate one enantiomer [i.e. (−)-14] and leave the other enantiomer [i.e. (+)-14] unreacted, which would be easily separated by conventional methods such as silica gel column chromatography. The acylated enantiomer [i.e. (−)-14] may be hydrolyzed to form the pure enantiomer [i.e. (−)-14]. The optically pure enantiomers thus obtained [(+)-14 and (−)-14] will be cyclized to (+)-15 and (−)-15, respectively, by Mitsunobu reaction. Reduction of (+)-15 and (−)-15 would lead to formation of (+)-16 and (−)-16. Hydrogenation of optically active forms of 15 and 16 would provide pure enantiomers of 17 and 18 [(+)-and (−)-17; (+)-and (−)-18]. Treatment of pure enantiomers of 15 with hydroxylamine and alkoxylamine affords enantiomerically pure oxime 19 [(+)-and (−)-19]. If desired, (+)-19 and (−)-19 may be reduced to produce enantiomerically pure 20 and 21 [(+)-and (−)-20; (+)-and (−)-21].

The 12-hydroxyl group in compound 1, 16, and 17 as well as their optically active forms can be epimerized by a number of methods including acidic conditions, neutral Mitsunobu conditions[57a–d], or with DAST.[57d] An example showing conversion of (−)-calanolide A [(−)-1] into (−)-calanolide B is depicted in Scheme VII.

The process may be utilized to prepare a wide variety of calanolide analogues such as Formulas i–v shown in Scheme VIII and Formulas vi–vii shown in Scheme IX. Additional exemplary calanolide analogues include but are not limited to Formulas 15 and 16

For Formula i, $R_1$ and $R_2$ are independently

······⃞ or ━━.

For Formula ii, $R_1$, $R_2$ and $R_3$ are independently H or $CH_3$.

For Formula iii, $R_1$ is $C_1$–$C_6$ linear or branched alkyl.

For Formula iv, $R_1$ is propyl or phenyl and $R_2$ is

······⃞OH or ━━OH.

For Formula vi, $R_1$ is $C_1$–$C_6$ linear or branched alkyl.

For Formula vii, $R_1$ is propyl or phenyl and $R_2$ is

······⃞OH or ━━OH.

shown in Scheme V, and Formulas 17 and 18 shown in Scheme VI.

Methods for treating and/or preventing viral infections using compounds of the invention are also described. Representative viral infections include HIV, hepatitis B, herpes simplex type 1 and 2, cytomegalovirus, varicella zoster virus, Epstein Barr virus, influenza A and B, parainfluenza, adenovirus, measles, and respiratory syncytial virus.

Accordingly, it is an object of the invention to provide calanolide analogues obtained via syntheses employing chromene 4 and chromanone 7 as key intermediates.

A further object of the invention is to provide a method for treating or preventing mycobacterium infections using calanolide analogues of the formula I:

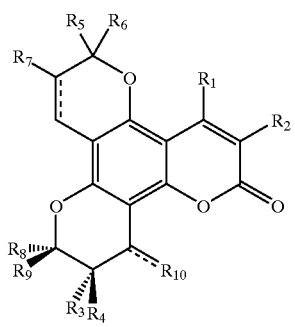

wherein

R₁ is H, halogen, hydroxyl, amino, $C_{1-6}$ alkyl, aryl-$C_{1-6}$ alkyl, mono-or poly-fluorinated $C_{1-6}$ alkyl, hydroxy-$C_{1-6}$ alkyl, $C_{1-6}$ alkoxy, amino-$C_{1-8}$ alkyl, $C_{1-6}$ alkyl amino, di($C_{1-6}$ alkyl)amino, $C_{1-8}$ alkylamino-$C_{1-8}$ alkyl, di($C_{1-6}$ alkyl) amino-$C_{1-8}$ alkyl, cyclohexyl, aryl, or heterocycle, wherein aryl or heterocycle may each be unsubstituted or substituted with one or more of the following: $C_{1-6}$ alkyl, $C_{1-6}$ alkoxy, hydroxy-$C_{1-4}$ alkyl, hydroxyl, amino, $C_{1-6}$ alkylamino, di($C_{1-6}$ alkyl) amino, amino-$C_{1-8}$ alkyl, $C_{1-8}$ alkylamino-$C_{1-8}$ alkyl, di($C_{1-6}$ alkyl)amino-$C_{1-8}$ alkyl, nitro, azido or halogen;

R₂ is H, halogen, hydroxyl, $C_{1-6}$ alkyl, aryl-$C_{1-6}$ alkyl, mono- or poly-fluorinated $C_{1-6}$ alkyl, aryl or heterocycle; R₃ and R₄ are independently selected from the group consisting of H, halogen, hydroxyl, amino, $C_{1-6}$ alkyl, aryl-$C_{1-6}$ alkyl, mono- or poly-fluorinated $C_{1-6}$ alkyl, hydroxy-$C_{1-6}$ alkyl, amino-$C_{1-8}$ alkyl, $C_{1-8}$ alkylamino-$C_{1-8}$ alkyl, di($C_{1-6}$ alkyl) amino-$C_{1-8}$ alkyl, cyclohexyl, aryl or heterocycle; and R₃ and R₄ can be taken together to form a 5–7 membered saturated cycle ring or heterocyclic ring;

R₅ and R₆ are independently selected from the group consisting of H, $C_{1-6}$ alkyl, aryl-$C_{1-6}$ alkyl, mono- or poly-fluorinated $C_{1-6}$ alkyl, aryl or heterocycle; and R₅ and R₆ can be taken together to form a 5–7 membered saturated cycle ring or heterocycle ring;

R₇ is H, halogen, methyl, or ethyl;

R₈ and R₉ are independently selected from the group consisting of H, halogen, $C_{1-6}$ alkyl, aryl-$C_{1-6}$ alkyl, mono- or poly-fluorinated $C_{1-6}$ alkyl, hydroxy-$C_{1-6}$ alkyl, amino-$C_{1-8}$ alkyl, $C_{1-8}$ alkylamino-$C_{1-8}$ alkyl, di($C_{1-6}$ alkyl) amino-$C_{1-8}$ alkyl, cyclohexyl, aryl or heterocycle; and R₈ and R₉ can be taken together to form a 5–7 membered saturated cycle ring or heterocyclic ring;

R₁₀ is halogen, O, OR₁₁, NOR₁₁, NHOR₁₁, NOR₁₂, NHOR₁₂, NR₁₁R₁₂, NR₁₂, or NR₁₂R₁₃; wherein R₁₁, is H, acyl, P(O)(OH)₂, S(O)(OH)₂, CO($C_{1-10}$ alkyl)CO₂H, ($C_{1-8}$ alkyl)CO₂H, CO($C_{1-10}$ alkyl)NR₁₂R₁₃, ($C_{1-8}$ alkyl) NR₁₂R₁₃; R₁₂ and R₁₃ are independently selected from the group consisting of H, $C_{1-6}$ alkyl, aryl, and aryl-$C_{1-6}$ alkyl; and R₁₂ and R₁₃ can be taken together to form a 5–7 membered saturated heterocyclic ring containing said nitrogen;

or a pharmaceutically acceptable salt thereof

These and other objects of the invention will be clear in light of the detailed descriptions below:

SCHEME I

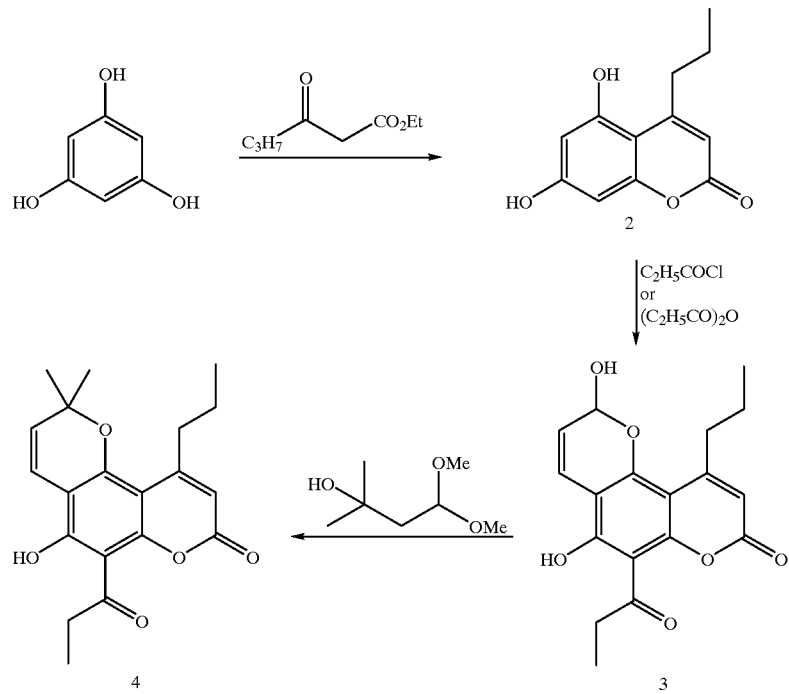

SCHEME II
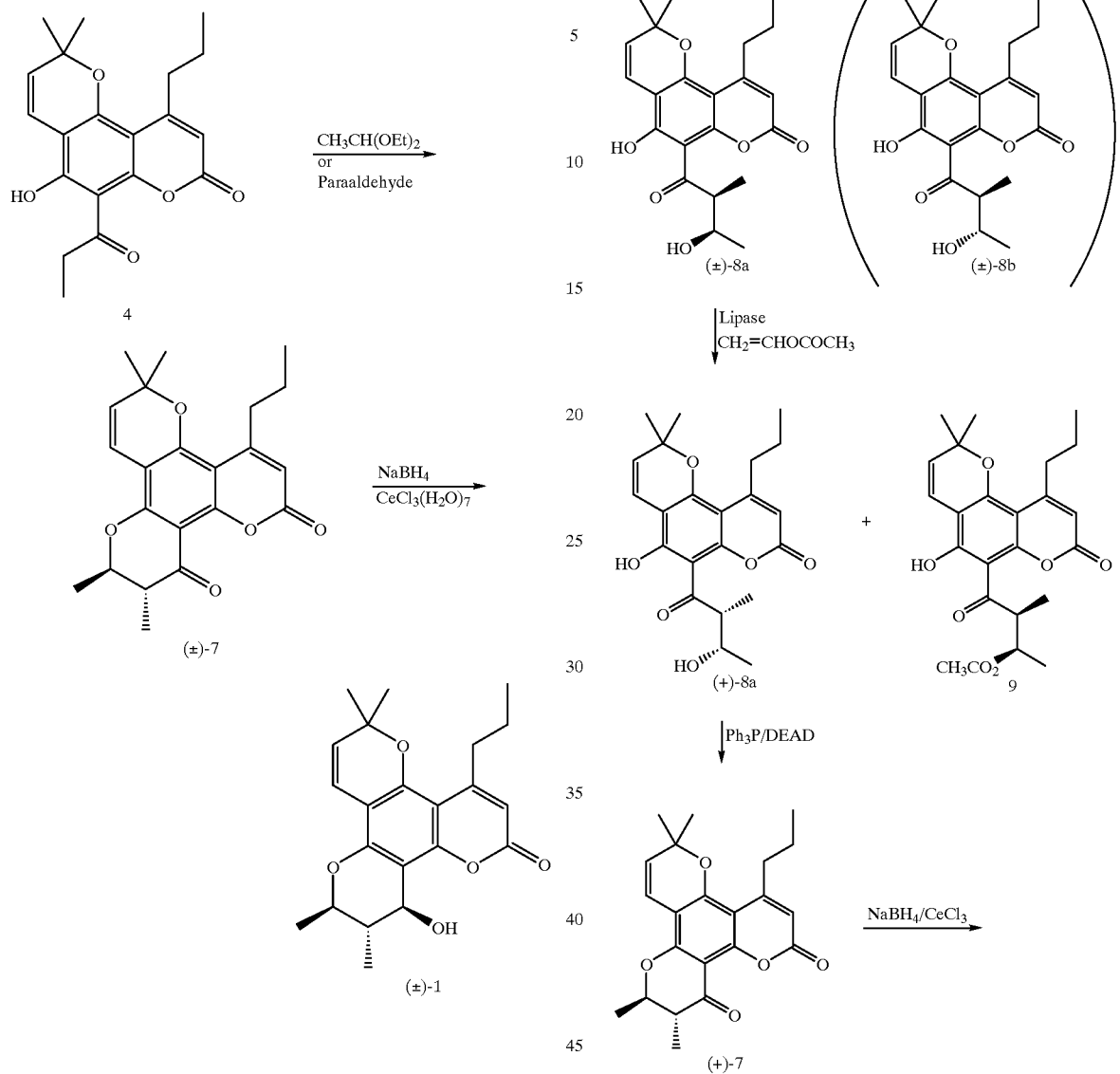
SCHEME III
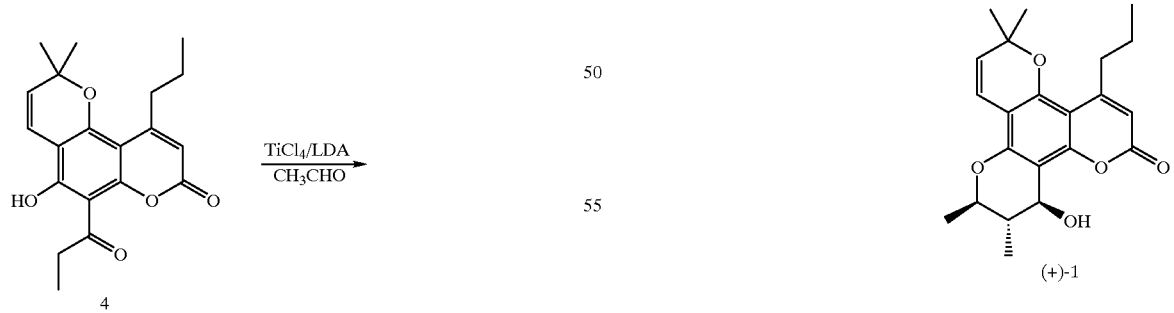

SCHEME IV
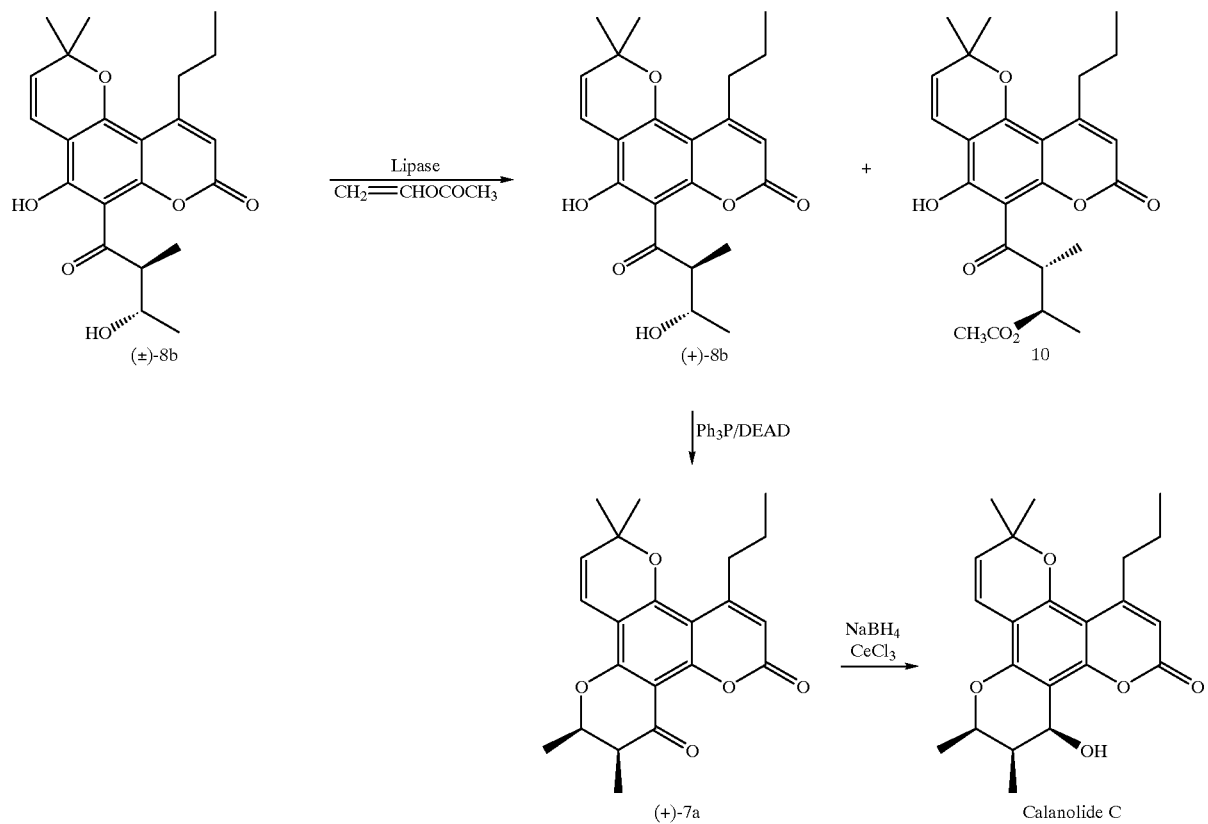
SCHEME V
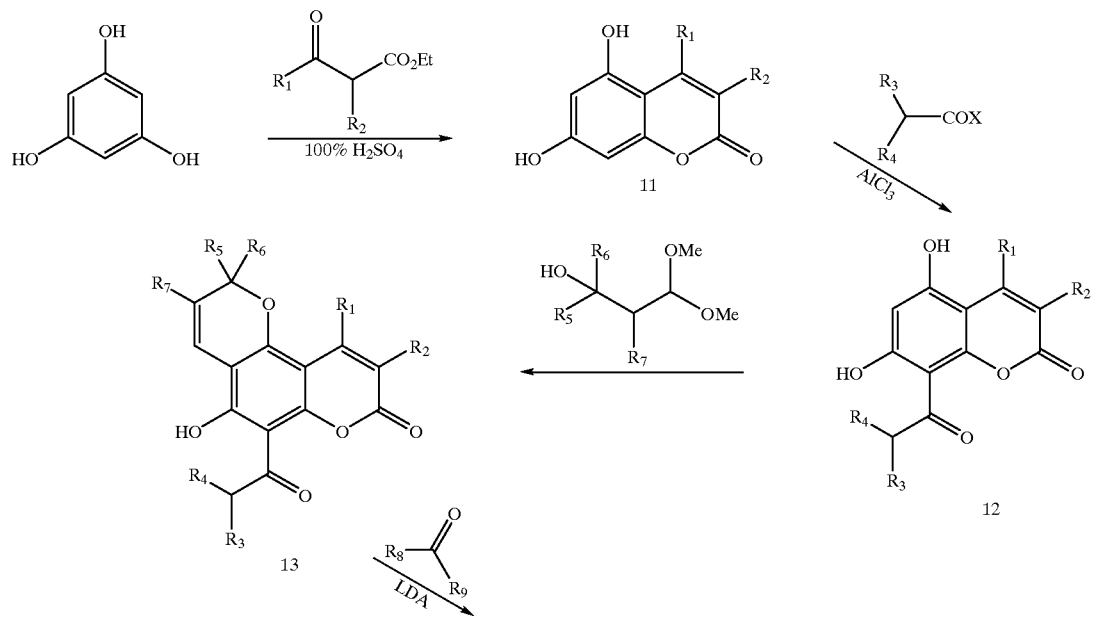

-continued
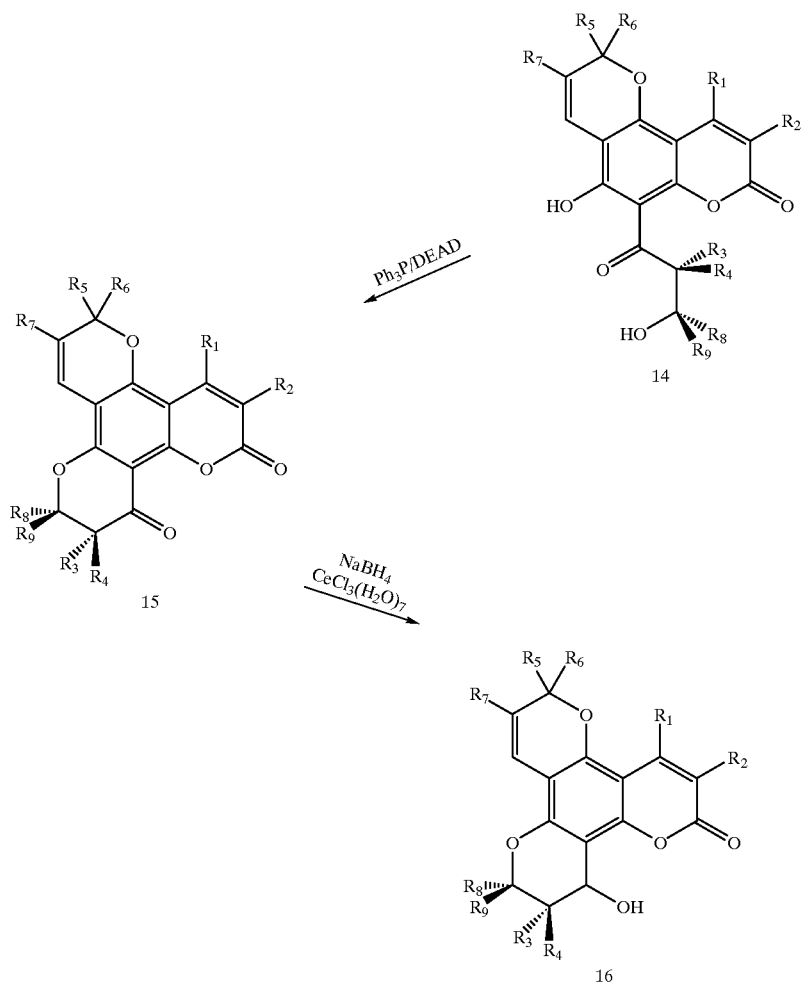
SCHEME VI
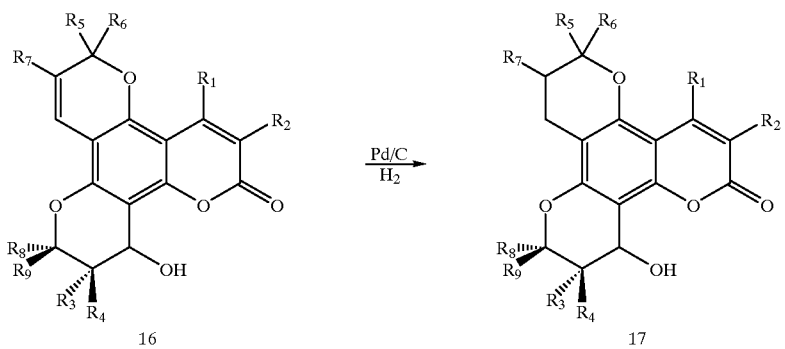

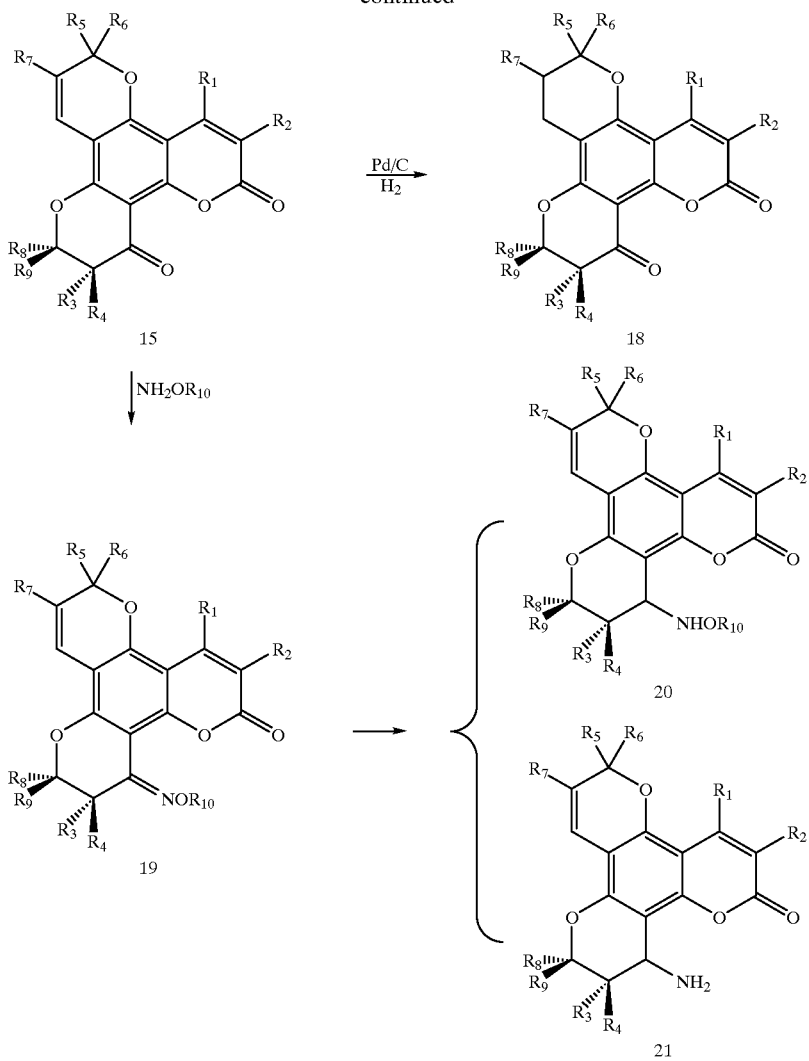
SCHEME VII
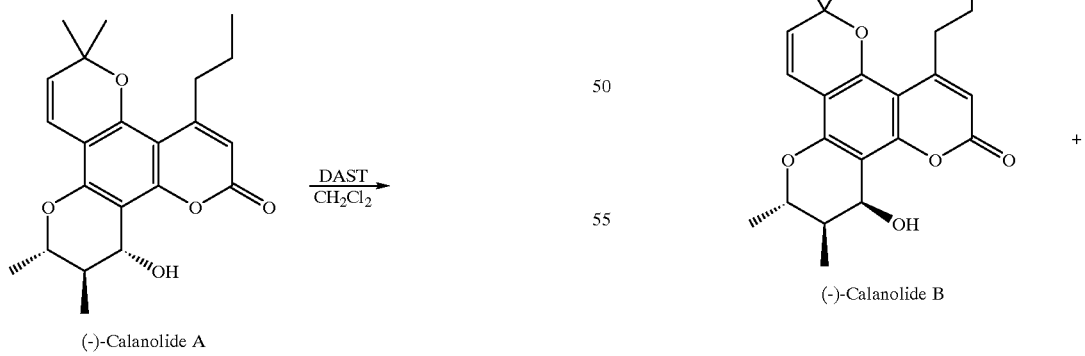

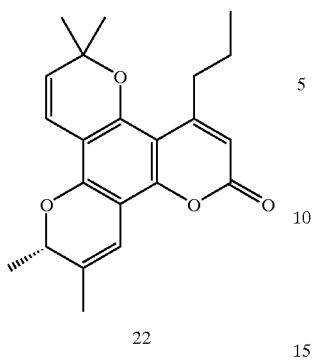

22

SCHEME VIII

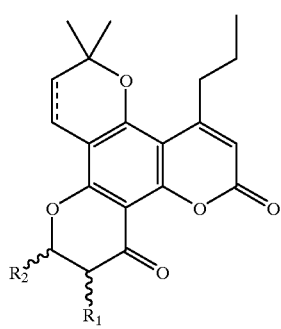

i

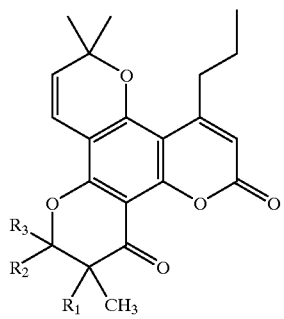

ii

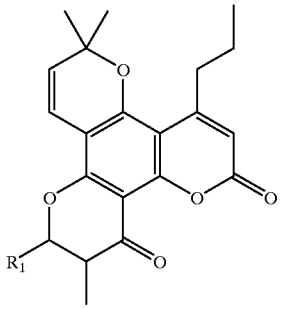

iii

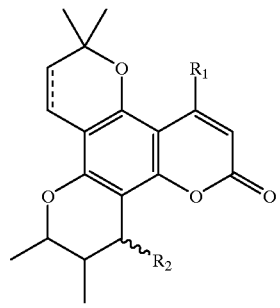

iv

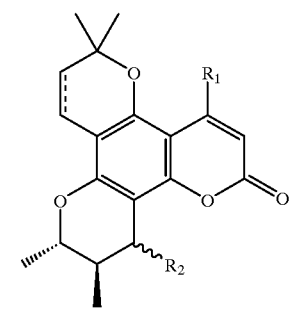

v

SCHEME IX

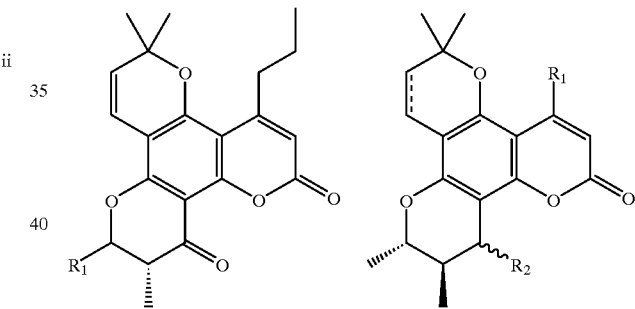

vi            vii

Figure 1:
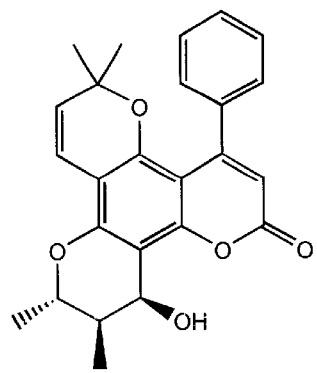
FIG. 1 illustrates a representative example of inventive compounds that were evaluated in the in vitro assay of example 38 in vitro MTT assay results, as described in Example 37, using G910-6 HIV viral strain which is AZT-resistant.
Figure 1:
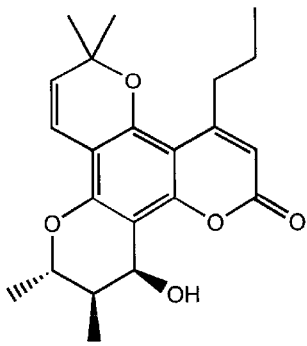
Figure 1:
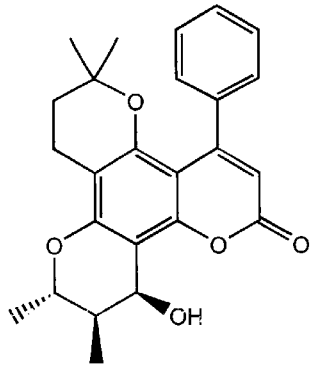
Figure 1:
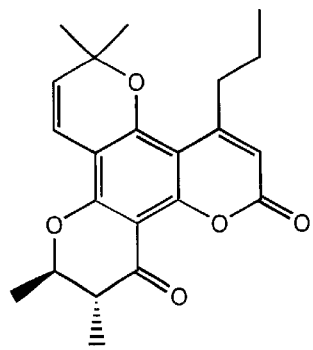
Figure 1:
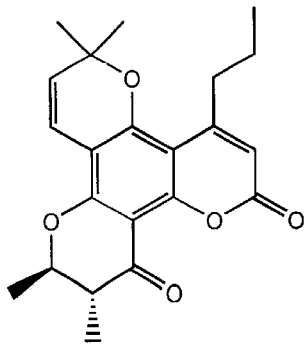
Figure 1:
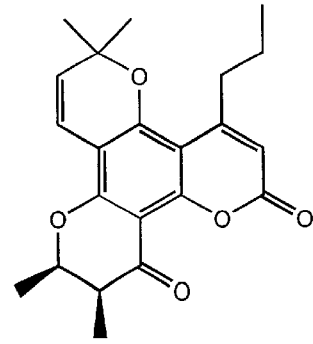
Figure 1:
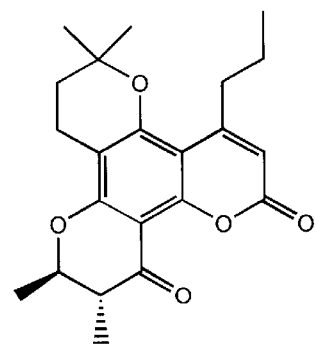

These and other objects of the invention would be clear in light of the detailed description below.

DETAILED DESCRIPTION OF THE INVENTION

All patents, patent applications, and references cited herein are incorporated by reference in their entirety.

(+)-Calanolide A, an anti-HIV agent currently undergoing Phase I/II clinical trials, was originally isolated from the rain forest tree, *Calophyllum lanigerum,* in Sarawak, Malaysia. Due to the scarce supply of (+)-calanolide A from natural resources, the applicants developed synthetic routes for both (±) and (+)-calanolide A.[40–43] The processes have been employed for kilogram-scale production of (+)-calanolide A. See, for instance, U.S. Pat. No. 5,489,697, WO96/04263, U.S patent application Nos. 08/510213 and 08/609,537 which are incorporated by reference in their entirety. The synthetic material has been utilized for various studies that include virological, pharmacological, toxicological, and pharmacokinetic evaluations in animals as well as in humans.

(−)-Calanolide A, an enantiomer of (+)-calanolide A, displayed strong anti-tuberculosis activity with 98% inhibition against Mtb H37Rv at a drug concentration of 12.5 $\mu$g/mL. Since both (+)-and (−)-calanolide A demonstrated potent anti-tuberculosis activity, (±)-Calanolide A might result in stronger activity than (+)- and (−)-calanolide A due to a positive synergetic effect. In addition, (±)-calanolide A has the advantage of being more easily synthesized.

The present invention relates to calanolide and analogues thereof and methods of using such compounds for treating or preventing mycobacterium infections. In one embodiment, the invention provides calanolide analogues obtained via syntheses employing chromene 4 and chromanone 7 as key intermediates, as shown in Schemes I and III. According to this synthetic scheme, chromene 4 may be prepared from 5,7-dihydroxy-4-propylcoumarin, 2, as shown in Scheme I. According to this synthetic scheme, 5,7-dihydroxy-4-propylcoumarin, 2,[55] was prepared quantitatively from ethyl butyrylacetate and phloroglucinol under Pechmann conditions.[56]

In conducting this reaction, a volume of a concentrated acid is added in a dropwise manner to a stirring mixture of ethyl butyrylacetate and phloroglucinol with a molar ratio ranging between about 3:1 and about 1:3, with a preferable range being about 0.9:1.0. The dropwise addition of an acid was conducted at a rate such that the temperature of the reaction mixture is maintained at a temperature ranging between about 0° C. and about 120° C., preferably about 90° C.

Suitable, but not limiting, examples of concentrated acid include sulfuric acid, trifluoroacetic acid, and methanesulfonic acid. In making compounds of the invention, concentrated sulfuric acid is particularly preferred. As the product yield and purity appear to be dependent on the amount of concentrated sulfuric acid used, it is preferred that the amount of concentrated sulfuric acid ranges between about 0.5 and 10 mole, most preferably ranging between about 2 and about 3.5 mole, per mole of ethyl butyrylacetate.

The reaction mixture is then heated to a temperature ranging between about 40° C. and about 150° C., preferably about 90° C., until the reaction reaches completion as detemiined by TLC analysis. The reaction mixture is then poured onto ice and the precipitated product is collected by filtration and dissolved in an organic solvent. Suitable, but non-limiting, examples of organic solvents include ethyl acetate, chloroform, and tetrahydrofuran. A preferred solvent is ethyl acetate. The resulting solution is then washed with brine and dried over a suitable drying agent, e.g., sodium sulfate. The yields of this reaction are generally quantitative.

Thereafter, 5,7-dihydroxy-8-propionyl-4-propylcoumarin, 3, was prepared by selectively acylating the 8-position of 5,7-dihydroxy-4-propylcoumarin, 2, with propionyl chloride in the presence of a Lewis acid catalyst (Friedel-Crafts acylation). In conducting this reaction, a solution of propionyl chloride in a suitable solvent, e.g., carbon disulfide, was added in a dropwise manner to a vigorously stirred solution of 5,7-dihydroxy-4-propylcoumarin, 2, a Lewis acid and an organic solvent cooled in an ice bath. Dropxwise addition of propionyl chloride is conducted such that the temperature of the reaction mixture is maintained at a temperature ranging between 0° C. and about 30° C., preferably between about 8° C. and 10° C.

In making compounds of the invention, the amount of propionyl chloride used generally ranges between about 0.5 and about 6 moles, preferably ranging between about 1 and about 2 moles, per mole of 5,7-dihydroxy-4-propylcoumazin, 2.

Non-limiting examples of Lewis acid catalysts useful in the acylation reaction include $AlCl_3$, $BF_3$, $SnCl_4$, $ZnCl_2$, $POCl_3$ and $TiCl_4$. A preferred Lewis acid catalyst is $AlCl_3$. The amount of Lewis acid catalyst relative to 5,7-dihydroxy-4-propylcoumarin, 2, ranges between about 0.5 and about 12 moles, preferably ranging between about 2 and about 5 moles, per mole of 5,7-dihydroxy-4-propylcoumarin, 2.

Non-limiting examples of organic solvent for use in preparing the 5,7-dihydroxy-4-propylcoumarin, 2, solution include nitrobenzene, nitromethane, chlorobenzene, or toluene and mixtures thereof. A preferred organic solvent for use in this invention is nitrobenzene.

Upon completion of the addition of propionyl chloride, the vigorously stirred reaction mixture is maintained at a temperature ranging between about 0° C. and about 120° C., preferably ranging between about 25° C. and 80° C., until the reaction reaches completion as monitored by conventional means such as TLC analysis. The reaction mixture is then poured onto ice and extracted several times with a suitable solvent such as ethyl acetate, chloroform, methylene chloride, tetrahydrofuran, or a mixture of chloroform/methanol. A preferred solvent for this extraction is ethyl acetate. The extracts are then dried over a suitable drying agent, e.g., sodium sulfate, and the product may be purified by conventional means such as silica gel column chromatography.

On small scale (<1 gram), the yield of 5,7-dihydroxy-8-propionyl-4-propylcoumarin 3, produced by the above described reaction is generally quantitative. However, on larger scale (>1 gram), the reaction was very difficult to control and did not exclusively afford the desired product as the desired 8-position acylated product 3 was accompanied by the formation of undesired 6-position acylated product and 6,8-bis-acylated product. Thus, an alternative and preferred route for preparing 5,7-dihydroxy-8-propionyl-4-propylcoumnarin 3 in large scale quantities was devised.

Preparation of 8-acylated coumarin 3 on a 5 gram scale as a single product (45% yield) has been achieved by adding a mixture of propionic anhydride, a Lewis acid, e.g., $AlCl_3$, and suitable solvent, e.g., 1,2-dichloroethane, into a vigorously stirring pre-heated mixture of coumarin, a Lewis acid, e.g., $AlCl_3$, and suitable solvent, e.g., 1,2-dichloroethane, at a temperature ranging between about 40° C. and about 160° C., preferably ranging between about 70° C. and about 75° C. Dropwise addition of the propionic anhydride solution is conducted at a rate such that the temperature of the reaction mixture is maintained within the desired temperature range.

The amount of propionic anhydride used in the reaction generally ranges between about 0.5 and about 10 moles, preferably ranging between about 1 and about 2 moles, per mole of 5,7-dihydroxy-4-propylcoumarin 2.

Non-limiting examples of Lewis acid catalysts useful in the acylation reaction include $AlCl_3$, $BF_3$, $POCl_3$, $SnCl_4$, $ZnCl_2$ and $TiCl_4$. A preferred Lewis acid catalyst is $AlCl_3$. The amount of Lewis acid catalyst relative to 5,7hydroxy-4-propylcoumarin, 2, ranges between about 0.5 and about 12 moles, preferably ranging between about 2 and about 4 moles, per mole of 5,7-dihydroxy-4-propylcoumarin, 2.

Suitable but nonlimiting examples of solvents for use in making compounds of the invention include diglyme, nitromethane, 1,1,2,2-tetrachloroethane, and 1,2-dichloroethane (preferred). Upon completion of the addition of propionyl anhydride, the vigorously stirred reaction mixture is maintained at a temperature ranging between about 40° C. and about 160° C., preferably ranging between about 70° C. and 75° C., until the reaction reaches completion as monitored by conventional means such as TLC analysis. The workup procedure is the same as described above.

The product was purified without the use of column chromatography to afford the desired product 3. This procedure has been scaled-up to 1.7 kg of coumarin (for details see experimental section) and the yield for 8-acylated coumarin 3 was 29% after recrystallization. The yield for 8-acylated coumarin 3 may be further improved by changing the purification processing. For example, the crude product may be recrystallized from solvent(s) other than dioxane, or a simple washing with an appropriate solvent may lead to product pure enough for the next reaction step.

Thereafter, chromene 4 was prepared by introducing the chromene ring into 5,7-dihydroxy-8-propionyl-4-propylcoumarin, 3, using 4,4-dimethoxy-2-methylbutan-2-ol. A solution of 5,7-dihydroxy-8-propionyl-4-propylcoumarin, 3, and 4,4-dimethoxy-2-methylbutan-2-ol in a suitable organic solvent in the presence of a base was reacted at a temperature ranging between about 40° C. and about 180° C., preferably ranging between about 100° C. and about 120° C., until the reaction reached completion as determned by conventional means such as TLC analysis. Water and methanol formed during the reaction were removed azeotropically via a Dean-Stark trap.

In making compounds of the invention, the amount of 4,4-dimethoxy-2-methylbutan-2-ol employed in the reaction generally ranges between about 0.5 and about 8 moles, preferably ranging between about 2 and about 4 moles, per mole of 5,7dihydroxy-8-propionyl-4-propylcoumarin 3.

Suitable, but not limiting examples of organic solvents include pyridine, triethylamine, N,N-dimethylformamide (DMF), toluene, tetrahydrofuran (THF) or 1,2-dichloroethane. Suitable, but non-limiting examples of the bases include pyridine, 4-dimethylaminopyridine, triethylamine, N,N-diethylaniline, 1,5-diazabicyclo-[4,3,0]-non-5-ene (DBN), 1,8-diazabicyclo-[5,4,0]undec-7-ene (DBU), sodium carbonate and sodium bicarbonate. Pyridine was used as both base and solvent in this invention on a small scale; for scale-up, however, pyridine was used as a base and toluene was used as a solvent.

Upon completion of the reaction, the solvent is removed under reduced pressure and the reaction product is dissolved in a suitable solvent, e.g., ethyl acetate. The solution is then washed sequentially with water and brine and dried over a suitable drying agent, e.g., sodium sulfate. Thereafter, the crude chromene 4 product can be purified by conventional means such as silica gel column chromatography using 25% ethyl acetate/hexane as the elution solvent. The yields of chromene 4 generally fall with the range of about 60% and about 85%, usually resulting in about 78% yield. Chromene 4 was then used to prepare chromanone 7.

A number of alternative routes were devised for preparing chromanone 7 from chromene 4 in large scale quantities. These routes were described in U.S. patent application Ser. No. 08/510,213, filed Aug. 2, 1995, the disclosure which is incorporated herein in its entirety. For instance, U.S. patent application Ser. No. 08/510,213 describes a one-step reaction process (paraldehyde one-step reaction), shown in Scheme II, and a two-step reaction process (LDA/sulfuric acid process or LDA/Mitsunobu process) for preparing chromanone 7 from chromene 4. Examples of these reactions are provided in the Examples below. In this invention, a new route for preparing chromanone 7 from chromene 4 was devised, shown in Scheme III, which introduces a chiral resolution step between the two step LDA/Mitsunobu process described in the 08/510,213 application and illustrated below. One of the benefits for including the enzyme acylation/resolution step at this stage of the process is that it provides a more practical and economical means for producing large scale amounts of chromanone (+)-7, which would lead to formation of (+)calanolide A after reduction without the subsequent need for chiral BPLC resolution of the racermic calanolide A.

According to Scheme III, (+)-chromanone 7 was prepared by a chlorotitanium-mediated aldol condensation reaction of chromene 4 with acetaldehyde which led to formation of aldol products (±)-8a and (±)8b in a ratio of 95:5, respectively. In conducting the aldol condensation reaction, a solution of LDA was added dropwise to a solution of chromene 4 dissolved in a solvent at a temperature ranging between about −78° C. and about 0° C., preferably about −30° C. and about −78° C. Thereafter, a solution of titanium tetrachloride was added dropwise to the stirng reaction mixture. The resulting solution was then warmed to a temperature ranging between about −78° C. and about 40° C., preferably about −40° C., and allowed to stir for about 45 minutes to allow for transmetallation. Thereafter, the solution was recooled to −78° C.

The amount of LDA added per mole of chromene 4 ranged between about 1 and about 4 moles, preferably ranging between about 2 and about 3 per mole of chromene 4. Dropwise addition LDA is conducted such that the reaction temperature is maintained within the desired range.

The amount of titanium tetrachloride ranges between about 0.5 and about 10 moles, preferably ranging between about 2 and about 4 moles per mole of chromene 4.

Suitable, but not limiting examples of solvent include methylene chloride, THF, diethyl ether, dioxane, etc.

Acetaldehyde was then added dropwise to the reaction mixture in amounts ranging between about 1 and about 12 moles, preferably ranging between about 4 and about 6 moles per mole of chromene 4. Dropwise addition of acetaldehyde is conducted such that the reaction temperature is maintained within the aforementioned range. The reaction was monitored by conventional means, e.g., TLC analysis, until it reached completion.

The aldol reaction of chromene 4 with acetaldehyde may be carried out under conditions which employs bases other than LDA. For example, metal hydroxides such as NaOH, KOH and $Ca(OH)_2$, metal alkoxides such as MeONa, EtONa and t-BuOK, and amines such as pyrrolidine, piperidine, diisopropylethylamine, 1,5-diazabicyclo[4,3,0] non-5-ene (DBN), 1,8-diazabicyclo[5,4,0]undec-7-ene (DBU), $NaNH_2$ and LiHMDS as well as hydrides such as NaH and KH can all be employed for the aldol reactions.[60]

Also, aldol reactions can be mediated by metal complexes of Al, B, Mg, Sn, Zn, Zr and other Ti compounds such as $(i\text{-PrO})_3\text{TiCl}$, $(i\text{-PrO})_4\text{Ti}$, $\text{PhBCl}_2$, $(n\text{-Bu})_2\text{BCl}$, $\text{BF}_3$, $(n\text{-Bu})_3\text{SnCl}$, $\text{SnCl}_4$, $\text{ZnCl}_2$, $\text{MgBr}_2$, $\text{Et}_2\text{AlCl}$ with or without chiral auxiliaries such as 1,1'-binaphthol, norephedrinesulfonate, camphanediol, diacetone glucose and dialkyl tartrate[61⊖]

Thereafter, the reaction mixture was quenched at −30° C. to −10° C. with saturated aqueous amnmonium chloride solution and extracted with a suitable solvent, e.g., ethyl acetate. The pooled extracts were washed with brine and dried over a suitable drying agent, e.g., sodium sulfate. The yields of aldol product generally range between about 40% and about 80%, usually about 70%.

It should be noted that the aldol reaction of chromene 4 results in a product having two asymmetric centers which in turn would result in a diastereomeric mixture of two sets of enantiomers (four optically active forms). The mixture may be separated by conventional means to produce racemic syn aldol product (±)8a and racemic anti aldol product (±)8b which may be resolved into optically active forms. Conventional resolution methods may be used such as chromatography or fractional crystallization of suitable diastereoisomeric derivatives such as salts or esters with optically active acids (e.g., camphor-10-sulfonic acid, camnphoric acid, methoxyacetic acid, or dibenzoyltartaric acid) or enzymatically catalyzed acylation or hydrolysis of the racemic esters. The resultant or synthetic enantiomer may then be transformed to enantioselective synthesis of (+)-calanolide A and its congeners.

In one method, the racemic aldol product may be resolved by high performance liquid chromatography (HPLC) with organic solvent system as a mobile phase. HPLC is performed on a column packed with chiral packing material. Suitable, but not limiting, examples of chiral packing material include amylose carbamate, D-phenylglycine, L-phenylglycine, D-leucine, L-leucine, D-naphthylalanine, L-naphthylalanine, or L-naphthylleucine. These materials may be bounded, either ionically or covalently, to silica sphere which particle sizes ranging between about 5 microns and about 20 microns. Suitable, but non-limiting, mobile phase includes hexane, heptane, cyclohexane, ethyl acetate, methanol, ethanol, or isopropanol and mixtures thereof. The mobile phase may be employed in isocratic, step gradient or continuous gradient systems at flow rates generally ranging between about 0.5 mL/min. and about 50 mL/min.

In making compounds of the invention, the racemic product, i.e., syn aldol product [(±)-8a], is resolved preferably by enzyme-catalyzed acylation. Enzymatic resolution may employ enzymes such as lipase CC (*Candida cylindracea*), lipase AK (*Candida cylindracea*), lipase AY (*Candida cylindracea*), lipase PS (Pseudomonas Species), lipase AP (*Aspergillus niger*), lipase N (*Rhizopus nieveuis*), lipase FAP (*Rhizopus nieveus*), lipase PP (Porcine Pancrease), pig (porcine) liver esterase (PLE), pig liver acetone powder (PLAP), or subtilisin. Immobilized forms of the enzyme on celite, molecular sieves, or ion exchange resin are also contemplated for use in this method. The amount of enzyme used in the reaction depends on the rate of chemical conversion desired and the activity of the enzyme. The preferred enzyme for use in the enzyme-catalyzed acylation reaction is lipase.

The enzymatic acylation reaction is carried out in the presence of an acylating agent. Suitable, but not limiting, examples of acylating agents include vinyl acetate, vinyl propionate, vinyl butyrate, vinyl stearate, acetic anhydride, propionic anhydride, phthalic anhydride, acetic acid, propionic acid, hexanoic acid or octanoic acid. The enzymatic reaction employs at least one mole of acylating agent per mole of aldol product. Acylating agent can be used as a solvent in the acylation reaction or in solution with another solvent such as hexanes, chloroform, benzene, tert-butylmethyl ether, and THF. The preferred solvent and acylating agent for use in the enzyme-catalyzed acylation are tert-butylmethyl ether and vinyl acetate, respectively.

Suitable, but not limiting examples of solvents for use in the enzymatic hydrolysis reaction include water, suitable aqueous buffers such as sodiun phosphate buffers, or alcohols such as methanol or ethanol.

One skilled in the art will appreciate that racemic esters of aldol products can be made by conventional esterification means and selectively hydrolyzed by enzymes so as to produce, in high enantiomeric excess, optically active aldol product, i.e., (+)-8, in free or esterified form.

The purified (+)-8a was subjected to a neutral Mitsunobu reaction, selectively leading to (+)-trans-chromanone [(+)-7]. In performing this reaction, diethyl azodicarboxylate (DEAD) was added dropwise to a solution containing (+)-8a and triphenylphosphine at a temperature ranging between about −10° C. and about 40° C., preferably about ambient temperature. The amount of DEAD used in the reaction generally ranges between about 1 mole and about 10 moles preferably about 1 mole and about 4 moles, per mole of aldol (+)-8a. The amount of triphenylphosphine used in the reaction generally ranged between about 1 mole and about 10 moles, preferably ranging between about 1 mole and about 4 moles, per mole of aldol (+)-8a.

Instead of DEAD, other suitable azo reagents reported in the literature can be employed such as diisopropyl azodicarboxylate (DIAD), dibutyl azodicarboxylate (DBAD), dipiperidinoazodicarboxamide, bis($N^4$-methylpiperazin-1-yl)azodicarboxamide, dimorpholinoazodicarboxamide, N,N,N',N'-tetramethylazodicarboxamide (TMAD)[64]. Also, in addition to triphenylphosphine, other phosphine derivatives such as tri-n-butylphosphine,[64] triethylphosphine, trimethylphosphine and tris(dimethylamino)phosphine may be used.

Thereafter, the reaction was quenched with saturated ammonium chloride upon completion and extracted with a suitable solvent, e.g., ethyl acetate. The pooled organic layers were washed with brine, concentrated in vacuo and the crude chromanone (+)-7 was purified by conventional means as discussed above. The yields of chromanone (+)-7 from the Mitsunobu reaction generally range between about 60% and about 80%, usually about 70%.

Finally, mild borohydride reduction of chromanone (+)-7 in the presence of $\text{CeCl}_3(\text{H}_2\text{O})_7$ (Luche reduction) produced (+)-calanolide A with the desired stereochemical arrangement. In conducting the reduction reaction, a solution of chromanone (+)-7 was added dropwise into a solution of reducing agent, e.g., sodium borohydride and a metal additive, e.g., $\text{CeCl}_3(\text{H}_2\text{O})_7$ in ethanol. The rate of addition is such that the reaction mixture temperature is maintained within a range of between about −40° C. and about 60° C., preferably ranging between about −10° C. and about −30° C. Thereafter, the reaction mixture was stirred at a temperature ranging between about −40° C. and about 60° C.

In general, the amount of metal additive, e.g., $\text{CeCl}_3(\text{H}_2\text{O})_7$ present in the reaction mixture ranged between about 0.1 and about 2 moles, preferably ranging between bout 0.5 and about 1 mole, per mole of sodium borohydride. In addition, the amount of reducing agent, e.g., sodium borohydride employed in the reaction generally ranged between about 0.1 and about 12 moles, preferably ranging between about 2 and about 4 moles, per mole of chromanone (+)-7. Suitable, but non-limiting, examples of reducing agents include NABH$_4$ LiAlH$_4$,(i-Bu)$_2$AlH,(n-Bu)$_3$SnH,9-BBN, Zn(BH$_4$)$_2$, BH$_3$, DIP-chloride, selectrides and enzymes such as baker yeast. Suitable, but non-limiting, examples of metal additives include CeCl$_3$, ZnCl$_2$, AlCl$_3$, TiCl$_4$, SnCl$_3$, and LnCl$_3$ and their mixture with triphenylphosphine oxide. In practicing this invention, sodium borohydride as reducing agent and CeCl$_3$(H$_2$O)$_7$ as metal additive are preferred.

Thereafter, the reduction mixture was diluted with water and extracted with a suitable solvent, e.g., ethyl acetate. The extract was dried over a suitable drying agent, e.g., sodium sulfate, and concentrated. The resulting residue was then purified by conventional means such as silica gel chromatography, using ethyl acetate/hexane solvent mixtures. Luche reduction on (+)-7 led to formation of (+)-calanolide A [(+)-1] which contained 10% of (+)-calanolide B. (+)-Calanolide A [(+)-1] was further separated from (+) calanolide B by preparative normal phase HPLC and was identical with an authentic sample.

Thus, (+)-calanolide A, 1, was successfully prepared with the desired stereochemical arrangement by treatment of the key intermediate chromene 4 with chlorotitanium catalyzed aldol reaction to produce (±)-8a, enzyme resolution of the racemate to produce (+)8a, and neutral Mitsunobu reaction of (+)-8a to produce chromanone (+)-7, followed by Luche reduction via chromanone (+)-7 (see Scheme III).

Enzyme resolution of trans-(±)-8b racemate with vinyl acetate and lipase allowed for the separation of (+)-8b, which, following treatment under neutral Mitsunobu reaction with triphenylphosphine and DEAD and subsequent Luche reduction, would result in calanolide C (Scheme IV).

In another embodiment of the invention, analogues of calanolide A are provided by extension of the aforementioned synthetic sequence for (+)-calanolide A. Pechmann reaction of phloroglucinol with substituted β-ketoesters yields substituted 5,7-dihydroxycoumarin 11 as shown in Scheme V. The conditions and reagents used in the Pechmann reaction are described above.

Suitable, but non-limiting, β-ketoesters include those of formula α:

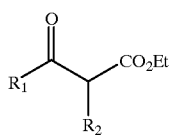

a wherein R$_1$ is H, halogen, hydroxyl, amino, C$_{1-6}$ alkyl, aryl-C$_{1-6}$ alkyl, mono- or poly-fluorinated C$_{1-6}$ alkyl, hydroxy-C$_{1-6}$ alkyl, C$_{1-6}$ alkoxy, amino-C$_{1-8}$ alkyl, C$_{1-6}$ alkylamino, di(C$_{1-6}$ alkyl)amino, C$_{1-8}$ alkylamino-C$_{1-8}$ alkyl, di(C$_{1-6}$ alkyl) amino-C$_{1-8}$ alkyl, cyclohexyl, aryl, or heterocycle, wherein aryl or heterocycle may each be unsubstituted or substituted with one or more of the following: C$_{1-6}$ alkyl, C$_{1-6}$ alkoxy, hydroxy-C$_{1-4}$ alkyl, hydroxyl, amino, C$_{1-6}$ alkylamino, di(Ci$_{1-6}$ alkyl)amino, amino-C$_{1-8}$ alkyl, C$_{1-8}$ alkylamino-C$_{1-8}$ alkyl, di(C$_{1-6}$ alkyl-amino-C$_{1-8}$ alkyl, nitro, azido or halogen; and R$_2$ is H, halogen, hydroxyl, C$_{1-6}$ alkyl, aryl-C$_{1-6}$ alkyl, mono- or poly-fluorinated C$_{1-6}$ alkyl, aryl or heterocycle.

Friedel-Crafts acylation of substituted 5,7-dihydroxycoumarin 11 leads to formation of 8-acylated 5,7-dihydroxycoumarin 12. The conditions and reagents used in the Friedel-Crafts acylation reaction are described above.

Non-limiting examples of carboxylic acid anhydrides and halides include formula b carboxylic acid anhydrides and halides:

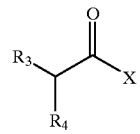

b wherein X is halogen (e.g. chloro) or OCOCHR$_3$R$_4$ wherein R$_3$ and R$_4$ are independently selected from the group consisting of H, halogen, hydroxyl, C$_{1-6}$ alkyl, aryl-C$_{1-6}$ alkyl, mono- or poly-fluorinated C$_{1-6}$ alkyl, hydroxy-C$_{1-6}$ alkyl, amino-C$_{1-8}$ alkyl, C$_{1-8}$ alkylamino-C$_{1-8}$ alkyl, di(C$_{1-6}$ alkyl)amino-C$_{1-8}$ alkyl, cyclohexyl, aryl or heterocycle; and R$_3$ and R$_4$ can be taken together to form a 5–7 membered saturated cycle ring or heterocyclic ring.

Chromenylation of 12 can be achieved by reacting with substituted β-hydroxyaldehyde dimethylacetal, affording chromenocoumarin 13. The conditions and amounts of reagents are described above. Representative examples of substituted β-hydroxyaldehyde dimethylacetals of formula c comprise:

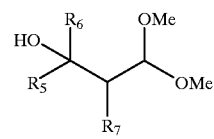

c wherein R$_5$ and R$_6$ are independently selected from the group consisting of H, C$_{1-6}$ alkyl, aryl-C$_{1-6}$ alkyl, mono- or poly-fluorinated C$_{1-6}$ alkyl, aryl or heterocycle; R$_5$ and R$_6$ can be taken together to form a 5–7 membered saturated cycle ring or heterocycle ring; and R$_7$ is H, halogen, methyl, ethyl.

Aldol condensation reaction of chromene 13 with carbonyl compounds in the presence of LDA forms the racemic aldol product (±)-14. According to the present invention, a solution of LDA in THF was added dropwise to a solution of chromene 13 in THF at a temperature ranging between about −78° C. and about 0° C., preferably about −30° C. and about −78° C. The amount of LDA added per mole of chromene 13 ranged between about 1 and about 4 moles, preferably ranging between about 2 and about 3 moles per mole of chromene 13. Dropwise addition of LDA is conducted such that the reaction temperature is maintained within the desired range.

A carbonyl compound of formula iv was then added dropwise to the reaction mixture in amounts ranging between about 1 and about 12 moles, preferably between about 4 and about 6 moles per mole of chromene 13. Dropwise addition of carbonyl compound is conducted such that the reaction temperature is maintained within the aforementioned range. The reaction was monitored by conventional means, e.g., TLC analysis, until it reached completion.

Representative examples of formula d carbonyl compounds comprise:

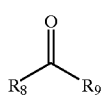

d wherein R₈ and R₉ are independently selected from the group consisting of H, halogen, $C_{1-6}$ alkyl, aryl-$C_{1-6}$ alkyl, mono- or poly-fluorinated $C_{1-6}$ alkyl, hydroxy-$C_{1-6}$ alky, amino-$C_{1-8}$ alkyl, $C_{1-8}$ alkylamino-$C_{1-8}$ alkyl di($C_{1-4}$ allkyl)amino-$C_{1-8}$ alkyl, cyclohexyl, aryl or heterocycle; and R₈ and R₉ can be taken together to form a 5–7 membered saturated cycle ring or heterocyclic ring.

One skilled in the art will appreciate that the aldol reaction of chromene 13 with carbonyl compounds of formula d to form 14 can be carried out under conditions which employs bases other than LDA. For example, metal hydroxides such as NaOH, KOH and Ca(OH)₂, metal alkoxides such as MeONa, EtONa and t-BuOK, and amines such as pyrrolidine, piperidine, dilsopropylethylamine, 1,5-diazabicyclo[4,3,0]non-5-ene (DBN), 1,8-diazabicyclo[5,4,0]undec-7-ene (DBU), NaNH₂ and LiHMDS as well as hydrides such as NaH and KH can all be employed for the aldol reactions.[10] Also, aldol reactions can be mediated by metal complexes of Al, B, Mg, Sn, Ti, Zn and Zr compounds such as TiCl₄, (i-PrO)₃TiCl, (i-PrO)₄Ti, PhBCl₂, (n-Bu)₂BCl, BF₃, (n-Bu)₃SnCl,SnCl₄, ZnCl₂, MgBr₂, Et₂AlCl with or without chiral auxiliaries such as 1,1'-binaphthol, norephedrinesulfonate, camphanediol, diacetone glucose and dialkyl tartrate.[11–13]

Thereafter, the reaction mixture was quenched at −30° C. to −10° C. with saturated aqueous ammonium chloride solution and extracted with a suitable solvent, e.g., ethyl acetate. The pooled extracts were washed with brine and dried over a suitable drying agent, e.g., sodium sulfate. The yields of aldol product (±)-14 generally range between about 40% and about 80%, usually about 70%.

Cyclization of (±)-14 under neutral Mitsunobu conditions, by using triphenylphosphine and diethyl azodicarboxylate (DEAD), leads to formation of chromanone analogue (±)-15. Reduction of (±)-15 with sodium borohydride with or without metal additives such as cerium chloride yields the 12-hydroxy analogue (±)-16 (Scheme V). The conditions and amounts of reagents used in the Mitsunobu and borohydride reduction reactions are described above.

Catalytic hydrogenation of both (±)-15 and (±)-16 produces 7,8-dihydro derivatives (±)-17 and (±)-18 (Scheme VI). To a solution of (±)-15 or (±)-16 in ethanol or ethanol/methylene chloride mixtures in a conventional Parr apparatus under H₂, hydrogenation catalyst was added at ambient temperature. The mixture was shaken under hydrogen for a time sufficient to complete the hydrogenation reaction. The solution was then gravity filtered to remove catalyst and solvent was evaporated.

Suitable, but non-limiting, hydrogenation catalysts for use in the invention include Pd/C, PtO₂ and Rh/C, Raney-Ni. In making compounds of the invention, 10% palladium/carbon is preferred. The amount of catalyst employed generally ranges between about 0.01 and about 0.5 mole, preferably ranging between about 0.05 and about 0.1 mole per mole of (±)-15 or (±)-16.

In yet another embodiment of the invention, intermediate chromanones (±)-7, (+)-7, (+)-7a and (±)-15 can be used to prepare oxime, hydroxyamino, alkoxyamino or amino calanolide derivatives. Treatment of the said chromanones with hydroxylamine or alkoxyamine affords oxime derivatives (±)-19 (Scheme VI).

Representative amines for preparing oxirne derivatives comprise NH₂OR₁₀ wherein R₁₀ is H, $C_{1-8}$ alkyl, phenyl, benzyl, acyl P(O)(OH)₂, S(O)(OH)₂, CO($C_{1-10}$ alkyl)CO₂H, ($C_{1-8}$ alkyl)CO₂H, CO($C_{1-10}$ alkyl)NR₁₂ R₁₃, ($C_{1-8}$ alkyl) NR₁₂R₁₃; wherein R₁₂ and R₁₃ are independently selected from the group consisting of H, $C_{1-6}$ alkyl; and R₁₂ and R₁₃ can be taken together to form a 5–7 membered saturated heterocyclic ring containing said nitrogen. Examples of useful alkoxyamnines include methoxyamine and benzyloxyamine.

The oxime derivatives may be prepared by refluxing a methanolic solution of the chromanone with hydroxyl amine or alkoxyamine in the presence of a metal carbonate such as potassium carbonate or pyridine until the reaction reaches completion. The amount of amine generally ranges between about 1 and about 20 moles, preferably between about 3 and about 6 moles, per mole of chromanone.

Upon completion of the reaction, filtration of the solution to remove solids and removal of solvent resulted in an oil which was purified via silica gel chromatography. The yields of oximes generally range between about 30% and about 80%, usually about 50%.

If desired, oxime derivatives (±)-19 may be reduced under different conditions[59] to yield hydroxyamino or amino compounds (20 and 21).

Thus, optically active forms of 14–21 (Scheme V and VI) would be obtained by employing enzymatic acylation, as described above, in the procedure outlined in Scheme III for (+)-calanolide A [(+)-1]. Enzyme-catalyzed acylation of the racemic aldol product (±)-14 would selectively acylate one enantiomer [i.e. (−)-14] and leave the other enantiomer [i.e. (+)-14] unreacted, which would be easily separated by conventional methods such as silica gel column chromatography. The acylated enantiomer [i.e. (−)-14] may be hydrolyzed to form the pure enantiomer [i.e. (−)-14]. The optically pure enantiomers thus obtained [(+)-14 and (−)-14] will be cyclized to (+)-15 and (−)-15, respectively, by the Mitsunobu reaction as described above. Subsequent reduction of (+)-15 and (−)-15 would lead to formation of (+)-16 and (−)-16, respectively. Hydrogenation of optically active forms of 15 and 16 would provide pure enantiomers of 17 and 18 [(+)-and (−)-17; (+)and (−)-18], respectively. Treatment of pure enantiomers of 15 with hydroxylamine or alkoxyamine, as described above, should afford enantiomerically pure oxime 19 [(+)-and (−)-19]. Reduction of (+)-19 and (−)-19 would lead to formation of enantiomerically pure 20 and 21 [(+)-and (−)-20; (+)-and (−)-21].

The 12-hydroxyl group in compound 1, 16, and 17 as well as their optically active forms can be epimerized under a variety of conditions including acidic conditions, neutral Mitsunobu conditions[57a–c], or with DAST.[57d] An example showing conversion of (−)-calanolide A [(−)-1] into (−)-calanolide B using DAST[57d] is depicted in Scheme VII.

Thus, the process used to produce compounds of the present invention may be utilized to prepare a wide variety of calanolide analogues such as Formulas i–v shown in Scheme VIII and Formulas vi–vii shown in Scheme IX.

For Formula i, R₁ and R₂ are independently

⋯⋯ꞁꞁꞁ or ◀.

For Formula ii, R₁, R₂, and R₃ are independently H or CH₃.

For Formula iii, R₁ is $C_1–C_6$ linear or branched alkyl.

For Formula iv, $R_1$ is propyl or phenyl and $R_2$ is

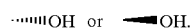

For Formula vi, $R_1$ is $C_1$–$C_6$ linear or branched alkyl.
For Formula vii, $R_1$ is propyl or phenyl and $R_2$ is

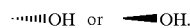

Additional exemplary calanolide analogues include but are not limited to Formulas 15 and 16 shown in Scheme V, and Formulas 17 and 18 shown in Scheme.

In another embodiment of the invention, (–)-calanolide B, obtained via conversion of (–)-calanolide A, is provided. It has been discovered that (–)-calanolide A may be converted readily to (–)-calanolide B using diethylamidosulfur trifluoride (DAST) or the Mitsunobi reaction, e.g., diethyl azodicazboxylate and triphenylphosphine, under the conditions and ranges described above.

The amount of DAST employed in the inversion reaction generally ranges between about 0.5 and about 5.0 moles, preferably ranging between about 1 and about 2.0 moles, per mole of (–)-calanolide A. Suitable, but non-limiting, reaction solvents for use in the invention include methylene chloride, THF, diethyl ether, or chloroform. In practicing the invention, the preferred solvent is methylene chloride. The reaction may be conducted at a temperature ranging between about −78° C. and about 50° C., preferably about −78° C., until the reaction is complete as determined by usual methods such as thin layer chromatography.

The calanolide compounds of the invention may be formulated as a solution of lyophilized powders for parenteral administration. Powders may be reconstituted by addition of a suitable diluent or other pharmaceutically acceptable carrier prior to use. The liquid formulation is generally a buffered, isotonic, aqueous solution. Examples of suitable diluents are normal isotonic saline solution, standard 5% dextrose in water or in buffered sodium or ammonium acetate solution. Such formulation is especially suitable for parenteral administration, but may also be used for oral administration. It may be desirable to add excipients such as polyvinylpyrrolidone, gelatin, hydroxy cellulose, acacia, polyethylene glycol, manuitol, sodium chloride or sodium citrate.

Alternatively, the compounds of the present invention may be encapsulated, tableted or prepared in an emulsion (oil-in-water or water-in-oil) syrup for oral administration. Pharmaceutically acceptable solids or liquid carriers, which are generally known in the pharmaceutical formulary arts, may be added to enhance or stabilize the composition, or to facilitate preparation of the composition. Solid carriers include starch (corn or potato), lactose, calcium sulfate dihydrate, terra alba, croscarmellose sodium, magnesium stearate or stearic acid, talc, pectin, acacia, agar, gelatin, maltodextrins and microcrystalline cellulose, or colloidal silicon dioxide. Liquid carriers include syrup, peanut oil, olive oil, corn oil, sesame oil, saline and water. The carrier may also include a sustained release material such as glyceryl monostearate or glyceryl distearate, alone or with a wax. The amount of solid carrier varies but, preferably, will be between about 10 mg to about 1 g per dosage unit.

The dosage ranges for administration of the calanolide compounds of the invention are those to produce the desired effect whereby symptoms of infection are ameliorated. For example, as used herein, a pharmaceutically effective amount for an mycobacterium infection refers to the amount administered so as to maintain an amount which suppresses or inhibits mycobacterium infection as evidenced by standard assay. The dosage will also be determined by the existence of any adverse side effects that may accompany the compounds. It is always desirable, whenever possible, to keep adverse side effects to a minimum.

One skilled in the art can easily determine the appropriate dosage, schedule, and method of administration for the exact formulation of the composition being used in order to achieve the desired effective concentration in the individual patient. However, the dosage can vary from between about 0.001 mg/kg/day to about 150 mg/kg/day, but preferably between about 0.01 to about 20.0 mg/kg/day.

The pharmaceutical composition may contain other pharmaceuticals in conjunction with the antimycobacterial calanolide analogues of the invention. For example, other pharmaceuticals may include, but are not limited to, antiviral compounds (e.g., AZT, ddC, ddI, D4T, 3TC, acyclovir, gancyclovir, fluorinated nucleosides and nonnucleoside analog compounds such as TIBO derivatives and nevirapine, α-interfon and recombinant CD4), protease inhibitors (e.g., indinavir, saquinavir, ritonavir, and nelfinavir), immunostimulants (e.g., various interleukins and cytokines), immunomodulators, (antimicrobials such as anti-TB agents isoniazid, rifampin, rifabutin, rifapentine, pyrazinamide, and etiambutol, antibacterial, antifungal, anti-pneumocysitis agents) and chemokine inhibitors. Administration of the inhibitory compounds with anti-retroviral agents that act against other HIV proteins such as protease, intergrase and TAT will generally inhibit most or all replicative stages of the viral life cycle.

The calanolides and analogues thereof described herein can be used either alone or in conjunction with other pharmaceutical compounds to effectively combat a single infection. For example, calanolides and analogues of the invention can be used either alone or combined with acyclovir in a combination therapy to treat HSV-1. Calanolides and analogues can also be used either alone or in conjunction with other pharmaceutical compounds to combat multiple infections. For example, calanolides and analogues thereof can be used in combination with one or more antimycobacterial acents agents such as anti-TB agents such as Isoniazid, rifamycins (e.g., rifampin, rifabutin and rifapentine), pyrazinamide, and ethambutol as a prophylatic or therapeutic treatment. Calanolides and analogues thereof can also be used in combination with Intron A and/or a biflavanoid for treating Hepatitis B; with gancyclovir, progancyclovir, famcyclovir, foscarnet, vidarabine, cidovir, and/or acyclovir for treating herpes viruses; and with ribavarin, amantidine, and/or rimantidine for treating respiratory viruses.

The following example is illustrative of the invention but does not serve to limit its scope.

EXPERIMENTAL

All chemical reagents and solvents referred to herein are readily available from a number of commercial sources including Aldrich Chemical Co. or Fisher Scientific. NMR spectra were run on a Hitachi 60 MHz R-1200 NMR spectrometer or a Varian VX-300 NMR spectrometer. IR spectra were obtained using a Midac M series Fr-IR instrument. Mass spectral data were obtained using a Finnegan MAT 90 mass spectrometer. All melting points are corrected.

EXAMPLE 1

5,7-Dihydroxy-4-propylcoumarin[55] (2)

Concentrated sulfric acid (200 mL) was added into a mixture of phloroglucinol dihydrate (150 g, 0.926 mol) and ethyl butyrylacetate (161 g, 1.02 mol). The resulting mixture was stirred at 90° C. for two hours whereupon it was poured onto ice. The solid product was collected by filtration, and then dissolved in ethyl acetate. The solution was washed with brine and dried over $Na_2SO_4$. After removal of the solvent in vacuo, the residue was triturated with hexane to provide essentially pure compound 2 (203 g) in quantitative yield, mp 233–235° C. (Lit.[55] 236–238° C.). $^1$H-NMR[55] (DMSO-$d_6$) δ0.95 (3H, t, J=6.9 Hz, $CH_3$); 1.63 (2H, apparent sextet, J=7.0 Hz, $CH_2$); 2.89 (2H, t, J=7.5Hz,$CH_2$); 5.85 (1H, s, $H_3$); 6.22 (1H, d, J=2.0 Hz, $H_6$); 6.31 (1H, d, J=2.0 Hz, $H_8$); 10.27 (1H, s, OH); 10.58 (1H, s, OH); MS (EI); 220(100, M$^+$); 205 (37.9, M-$CH_3$); 192 (65.8, M-$C_2H_4$); 177 (24.8, M-$C_3H_7$); 164 (60.9, M-$CHCO_2$+1); 163 (59.6 M-$CHCO_2$); IR (KBr): 3210 (vs and broad, OH); 1649 (vs, sh); 1617 (vs, sh); 1554 (s) cm$^{-1}$; Anal. calcd. for $C_{12}H_{24}O_4$: C, 65.45; H, 5.49;.Found: C, 65.61; H, 5.44.

EXAMPLE 2

5,7-Dihydroxy-8-propionyl-4-propylcoumarin (3)

A three-neck flask (500 mL) equipped with an efficient mechanical stirrer, thermometer and addition funnel was charged with 5,7-dihydroxy-4-propylcoumarin, 2, (25.0 g, 0.113 mol), aluminum chloride (62.1 g; 0.466 mol), and nitrobenzene (150 mL) and the mixture was stirred until a solution was obtained, which was cooled to 0° C. in an ice bath. A solution of propionyl chloride (15.2 g; 0.165 mol) in carbon disulfide (50 mL) was added dropwise at such a rate that the reaction temperature was maintained at 8–10° C. Addition was completed over a period of 1 hour with vigorous stirring. The reaction was monitored by TLC using a mobile phase of 50% ethyl acetate/hexane. After three hours, an additional portion of propionyl chloride (2.10 g; 0.0227 mol) in carbon disulfide (10 mL) was added. Immediately after the TLC analysis indicated the total consumption of starting material, the reaction mixture was poured onto ice, and allowed to stand overnight. The nitrobenzene was removed by steam distillation, and the remaining solution was extracted several times with ethyl acetate. The extracts were combined and dried over $Na_2SO_4$. The crude product obtained by evaporation in vacuo was purified by chromatography on a silica gel column eluting with 50% ether/hexane to provide the desired propionylated coumarin 3, mp 244–246° C. $^1$H-NMR (DMSO-$d_6$) δ0.96 (3H, t, J=7.3 Hz, $CH_3$); 1.10 (3H, t, J=7.2 Hz, $CH_3$); 1.60 (2H, m, $CH_2$); 2.88 (2H, t, J=7.7 Hz, $CH_2$); 3.04 (2H, q, J=7.2 Hz, $CH_2$); 5.95 (1H, s, $H_3$); 6.31 (1H, s, $H_6$); 11.07 (1H, s, OH); 11.50 (1H, s, OH); MS (EI): 277 (6.6, M+1); 276 (9.0, M$^+$); 247 (100, M-$C_2H_5$); IR (KBr): 3239 (s and broad, OH); 1693 (s, C=O), 1625 and 1593 (s) cm$^{-1}$; Anal. calcd. for $C_{15}H_{16}O_5$: C, 65.21; H, 5.84; Found: c, 64.92; H, 5.83. The isomer assignment was made by analogy to precedent.[65]

EXAMPLE 3

2,2-Dimethyl-5hydroxy-6-propionyl-10-propyl-2H, 8H-benzo[1,2-b:3,4-b']dipyran-8one (4)

A mixture of 3 (2.60 g, 9.42 mmol) and 4,4-dimethoxy-2-methylbutan-2-ol (5.54 g, 37.7 mmol) were dissolved in anhydrous pyridine (6.5 mL). The mixture was refluxed under nitrogen for three days. After removal of the solvent in vacuo, the residue was dissolved in ethyl acetate. The ethyl acetate was washed several times with 1 N HCl and brine. It was then dried over $Na_2SO_4$. The crude product obtained by evaporation in vacuo was purified by silica gel column chromatography, eluting with 25% ethyl acetate/ hexane to afford 2.55 g of 4 in 78.6% yield, mp 96–98° C. $^1$H-NMR (CDCl$_3$) δ1.05 (3H, t, J=7.3 Hz, $CH_3$); 1.22 (3H, t, J=7.5 Hz, $CH_3$); 1.53 (6H, s, 2 $CH_3$); 1.75 (2H, m, $CH_2$); 2.92 (2H, t, J=7.1 Hz, $CH_2$); 3.35 (2H, q, J=7.1 Hz, $CH_2$); 5.56 (1H, d, J=10.0 Hz, $H_3$); 5.98 (1H, s, $H_9$); 6.72 (1H, d, J=10.0 Hz, $H_4$); MS EI): 343 (5.7, M+1); 342 (22.5, M$^+$); 327 (100, M-$CH_3$); IR (KBr): 1728 (vs, C=O) cm$^{-1}$; Anal. calcd. for $C_{20}H_{22}O_5$: C, 70.16; H, 6.48; Found: C, 70.45; H, 6.92.

EXAMPLE 4

10,11 -Didehydro-12-oxocalanolide A (5)

A mixture of 4 (1.76 g, 5.11 mmol) and sodium acetate (0.419 g, 5.11 mmol) in acetic anhydride (12 mL) were refluxed for 10 hours whereupon the solvent was removed in vacuo. The residue was purified by silica gel column chromatography, eluting first with 25% ethyl acetate/hexane followed by 50% ethyl acetate/hexane to provide 1.16 g (62% yield) of enone 5 (6,6,10,11-tetramethyl-4-propyl-2H, 6H,12H-benzo[1,2-b:3,4-b':5,6-b"]tripyran-2,12-dione) as a white solid, mp 209–209.5° C. $^1$H-NMR (CDCl$_3$) δ1.05 (3H, t, J=6.6 Hz, $CH_3$); 1.56 (6H, s, 2 $CH_3$); 1.73 (2H, m, $CH_2$); 1.98 (3H, s, $CH_3$); 2.38 (3H, s, $CH_3$); 2.91 (2H, t, J=7.5 Hz, $CH_2$); 5.69 (1H, d, J=10.0 Hz, $H_7$); 6.11 (1H, s, $H_3$); 6.71 (1H, d, J=10 Hz, $H_8$); MS (EI): 366 (29.6, M$^+$); 351 (100, M-$CH_3$); 323 (16.5, M-$C_3H_7$); IR (KBr): 1734 (vs, C=O), 1657, 1640, 1610, and 1562 cm$^{-1}$; Anal. calcd. for $C_{22}H_{22}O_5$: 72.12; H, 6.05; Found: C, 72.14; H, 6.15.

EXAMPLE 5

10,11-Didehydrocalanolide A (6)

A mixture of enone 5 (160 mg, 0.437 mmol) and tri-n-butyltin hydride (0.318 g, 1.09 mmol) in dry dioxane (2.0 mL) was refluxed under nitrogen for 12 hours. The solvent was then removed in vacuo and the residue was purified by preparative TLC using 25% ethyl acetate in hexane as the mobile phase. The product exhibited an $R_f$ of about 0.4. Enol 6 (12-hydroxy-6,6,10,11-tetramethyl-4-propyl-2H,6H,12H-benzo[1,2-b:3,4-b':5,6-b"]tripyran-2-one) (13.3 mg, 8%) was isolated as an oil from the plate by ethyl acetate elution. This elution may have been inefficient, and the actual yield higher, as indicated by analytical TLC of the crude product $^1$H-NMR (CDCl$_3$) δ0.92 (3H, t, J=6.0 Hz, $CH_3$); 1.26 (3H, s, $CH_3$); 1.39 (3H, s, $CH_3$); 1.63 (2H, m, $CH_2$); 1.96 (3H, s, $CH_3$); 2.36 (3H, s, $CH_3$); 2.45 (2H, t, J=6.0 Hz, $CH_2$); 3.65 (1H, s, $H_{12}$); 5.51 (1H, d, J=10.0 Hz, $H_7$); 6.06 (1H, S, $H_3$); 6.67 (1H, d, J=10.0 Hz, $H_8$); 13.25 (1H, br s, OH); MS (EI): 369 (3.8, M+1), 368 (4.4, M$^+$), 367 (8.3, M-1) 366 (28.4, M-2), 351 (100, M—OH); IR(KBr): 1651 (s), 1589 (m)cm$^{-1}$.

EXAMPLE 6

12-Oxocalanolide A [(±)-(7)

A solution containing chromene 4 (344 mg, 1.0 mmol), acetaldehyde diethylacetal (473 mg, 4.0 mmol), trifluoro-acetic acid (1.5 mL, 19.4 mmol) and anhydrous pyridine (0.7 mL) was heated at 140° C. under $N_2$. The reaction was monitored by TLC analysis. After 4 hours, the reaction mixture was cooled. to room temperature, diluted with ethyl acetate and washed several times with 10% aqueous NaHCO$_3$ and brine. The organic layer was separated and dried over $Na_2SO_4$. The solvent was removed in vacuo and the crude product was purified by silica gel column chromatography eluting with ethyl acetate/hexane (2:3). Chromanone (±)-7 (10,11-trans-dihydro-4-propyl-6,6,10,11-tetramethyl-2H,6H,12H-benzo[1,2-b:3,4-b':5,6-b"]-tripyran-2,12-dione) (110 mg, 30% yield) was obtained m.p. 176–177° C. (Lit.[55] 130–132° C.). $^1$HNMR[55] (CDCl$_3$) δ1.02 (3H, t, J=7.5 Hz, CH$_3$); 1.21 (3H, d, J=6.8 Hz, CH$_3$); 1.51 (3H, d, J=7.0 Hz, CH$_3$); 1.55 (6H, 2s, 2 CH$_3$); 1.63 (2H, sextet, J=7.0 Hz, CH$_2$); 2.55 (1H, dq, J=6.9 Hz, J=11.0 Hz, H$_{11}$); 2.88 (2H, t, J=7.6 Hz, CH$_2$); 4.28 (1H, dq, J=6.3 Hz, J=11.0 Hz, H$_{10}$); 5.60 (1H, d, J=9.9 Hz, H$_7$); 6.04 (1H, s, H$_3$); 6.65 (1H, d, J=11.8 Hz, H$_8$); MS (CI): 369 (100, M+1).

EXAMPLE 7

7:(±)-Calanolide A (1)

To a solution of chromanone (±)-7 (11 mg, 0.03 mmol) in ethanol (0.4 mL) was added sodium borohydride (2.26 g, 0.06 mmol) and CeCl$_3$(H$_2$O)$_7$ (11.2 mg, 0.03 mmol) in ethanol (5 mL) at room temperature. After stirring for 45 minutes, the mixture was diluted with H$_2$O and extracted with ethyl acetate. The organic layer was dried over Na$_2$SO$_4$ and concentrated. The crude product was purified by preparative TLC eluting with ethyl acetate/hexane (1:1) to afford (±)-calanolide A (1) (10.5 mg, 94%). m.p. 52–54° C., which increased to 102° C. after it was dried thoroughly (Lit[55]. 56–58° C.). $^1$NMR (CDCl$_3$): δ1.03 (3H, t, J=7.3Hz, CH$_3$), 1.15 (3H, d, J=6.8 Hz, CH$_3$), 1.46 (3H, d, J=6.8Hz, CH$_3$), 1.47 (3H, s, CH$_3$), 1.51 (3H, s, CH$_3$), 1.66 (2H, m, CH$_2$), 1.93 (1H, m, H$_{11}$), 2.89 (2H, m, CH$_2$), 3.52 (1H, broad-s, OH), 3.93 (1H, m, H$_{10}$), 4.72 (1H, d, J=7.8 Hz, H$_{12}$), 5.54 (1H, d, J=10.0 Hz, H$_7$), 5.94 (1H, s, H$_3$), 6.62 (1H, d, J=9.9Hz, H$_8$); MS (CI): 371 (75.4, M+1), 370 (16.1, M$^+$), 353 (100, M—OH); Anal. calcd. for C$_{22}$H$_{25}$O$_5$: C, 71.33; H, 7.07; Found: C, 71.63; H, 7.21.

EXAMPLE 8

5,7-Dihydroxy-4-propylcoumarin (2)

In this Example, kilogram scale preparation of intermediate 2 is described. Into a stirring suspension of phloroglucinol (3574.8 g, 28.4 mol, pre-dried to constant weight) and ethyl butyrylacetate (4600 mL, 28.4 mol) was added concentrated sulfuric acid dropwise at such a rate that the internal temperature did not exceed 40° C. After 100 mL of sulfric acid was added, the temperature rose to 70° C. and the suspension turned into a yellow solid. Analysis of TLC indicated that the reaction had proceeded to completion. The reaction mixture was diluted with water (10 L) and stirred at ambient temperature overnight. The precipitated product was collected by filtration and then rinsed with water until the filtrate was neutral. A quantity of 4820 g (77% yield) of 5,7-dihydroxy-4-propylcoumarin 2 was obtained after being dried, which was identical with an authentic sample by comparison of TLC, melting point and spectroscopic data.

EXAMPLE 9

5,7-Dihydroxy-8-propionyl-4-propylcoumarin (3)

In this Example, kilogram quantities of intermediate 3 were synthesized using propionic anhydride instead of propionyl chloride. 5,7-dihydroxy-4-propylcoumarin 2 (1710 g, 7.77 mol) and AlCl$_3$ (1000 g, 7.77 mol) were mixed in 1,2-dichloroethane (9 L). The resulting orange suspension was stirred and heated to 70° C. until a solution was obtained. Then, a mixture of propionic anhydride (1010 g. 7.77 mol) and AlCl$_3$ (2000 g, 15.54 mol) in 1,2-dichloroethane (3.4 L) was added dropwise over 3 h. The reaction was allowed to stir at 70° C. for an additional hour. After being cooled down to room temperature, the reaction mixture was poured into a rapidly stirring mixture of ice water and 1N HCl. The precipitated product was taken into ethyl acetate (30 L) and the aqueous solution was extracted with the same solvent (10 L×2). The combined extracts were successively washed with 1 N HCl (10 L), saturated aq. NaHCO$_3$ (10 L), and water (10 L). After being dried over MgSO$_4$ and concentrated in vacuo, a solid product (1765 g) was obtained which was washed with ethyl acetate (15 L) and recrystallized from dioxane (9.5 L) to provide 514 g of pure compound 3. From the ethyl acetate washings, an additional 100 g of compound was obtained after recrystallization from dioxane. Thus, the combined yield for compound 3, which was identical with an authentic sample by comparison of TLC, melting point and spectroscopic data, was 29%.

EXAMPLE 10

2,2-Dimethyl-5-hydroxy-6-propionyl-10-propyl-2H, 8H-benzo[1,2-b:3,4-b']dipyran-8one (4)

In this Example, intermediate 4 was prepared in half kilogram quantities from 3 via modification of the reaction conditions described in Example 3. A mixture of compound 3 (510.6 g, 1.85 mol) and 4,4-dimethoxy-2-methylbutan-2-ol (305.6 g, 2.06 mol) were dissolved in a mixture of toluene (1.5 L) and dry pyridine (51 mL). This mixture was stirred and refluxed; water and methanol formed during the reaction were removed azeotropically via a Dean-Stark trap. The reaction was monitored by TLC. After 6 days, the reaction had proceeded to completion. The mixture was then cooled to ambient temperature and diluted with ethyl acetate (2 L) and 1 N HCl (1 L). The ethyl acetate solution was separated and washed with 1N HCl (500 mL) and brine (1 L). After being dried over Na$_2$SO$_4$ and evaporated in vacuo, a quantity of 590 g (93% yield) of compound 4 was obtained which was greater than 95% pure without further purification and was compared with an authentic sample by TLC and spectroscopic data.

EXAMPLE 11

12-Oxocalanolide A ((±)-7)

In this Example, chromanone (±)-7 was prepared from two alternative pathways involving either a one-step paraldehyde reaction (procedure A) or a two-step reaction process (procedures B and C).

Procedure A. Paraldehyde One-Step Reaction: To a stirring solution of chromene 4 (350 mg, 1.0 mmol) and PPTS (250 mg, 1.0 mmol) in 1,2-dichloroethane (2 mL) at ambient temperature under N$_2$ was added 3 mL paraldehyde (22.5 mmol). The resulting mixture was refluxed for 7 h. Then, CF$_3$CO$_2$H (1 mL), an additional equivalent of PPTS and 1 mL of paraldehyde were added; the mixture was refluxed overnight. The reaction mixture was neutralized with saturated aqueous NaHCO$_3$ and extracted with ethyl acetate (50 mL×3). The crude product obtained by evaporation under reduced pressure was washed with hexane. The residue was purified by column chromatography eluting with ethyl acetate/hexane (1:2) to afford 100 mg (27% yield) of chromanone (±)-7 and 30 mg (8% yield) of (±)-7a. Chromanone (±)-7 (10,11-trans-dihydro-4-propyl-6,6,10,11-tetramethyl-2H,6H, 12H-benzo[1,2-b:3,4-b': 5,6-b"]tripyran-2,12-dione) obtained by this method was identical with an authentic sample by comparison of TLC, HPLC and spectroscopic data.

Procedure B LDA/Sulfuric Acid Two-Step Reaction: To a stirring solution of chromene 4 (5.0 g, 14.6 mmol) in THF (75 mL) at −30° C. under $N_2$ was added 18.3 mL (36.5 mmol) of 2 M LDA in THF. After 15 min at the same temperature, acetaldehyde (5.0 mL, 89.5 mmol) was added via syringe. The reaction was monitored by TLC analysis. After 1 h, the reaction mixture was quenched at −10° C. with saturated aqueous $NH_4Cl$ (75 mL) and extracted with ethyl acetate (125 mL×3). The combined extracts were washed with brine (125 mL) and dried over $Na_2SO_4$. Removal of solvents in vacuo afforded a reddish oil of (±)-8a and (±)-8b (8.5 g).

The crude (±)-8a and (±)8b was dissolved in acetic acid (100 mL) and then 50% $H_2SO_4$ (100 mL) was added with stirring. The resulting mixture was heated at 75° C. for 2.5 h and then at 50° C. for 4 h. TLC analysis indicated that the starting material had been consumed. The reaction mixture was determined to contain both chromanone (±)-7 and 10,11-cis-dimethyl derivative (±)-7a in a 1:1 ratio. After cooling to ambient temperature, the reaction mixture was poured into a mixture of ice water (500 mL) and ethyl acetate (500 mL). The layers were separated and the aqueous layer was extracted with ethyl acetate (200 mL×3). The ethyl acetate solutions were combined and washed with saturated aqueous $NaHCO_3$ and brine. After being concentrated in vacuo, the product was purified by chromatography on a silica gel column eluting with ethyl acetate/hexane (2:3) to provide 850 mg (16% yield) of chromanone (±)7, which was further purified by recrystallization from ethyl acetate/hexane and was identical with an authentic sample by comparison of TLC, HPLC and spectroscopic data.

Procedure C. LDA/Mitsunobu Two-Step Reaction: Into a stirring solution of THF (10 mL) containing triphenylphosphine (1.27 g, 4.80 mmol) and the crude mixture of (±)-8a and (±)8b, obtained from chromene 4 (1.0 g, 2.34 mmol), 2.5 equivalents of LDA and 6.0 equivalents of acetaldehyde by the procedure described above, was added dropwise diethyl azodicarboxylate (DEAD, 0.77 mL, 4.89 mmol). The resulting reddish solution was stirred at ambient temperature under $N_2$ for 1 h, after which the reaction mixture was quenched with saturated aqueous $NH_4Cl$ and extracted with ethyl acetate (50 mL×3). The extracts were washed with brine and dried over $Na_2SO_4$. After removal of solvents, the crude product was purified by column chromatography on silica gel eluting with ethyl acetate/hexane (2:3) to provide 412 mg (48% yield, based on chromene 4) of chromanone (±)-7, the predominant product of the reaction, which was identical with an authentic sample by comparison of TLC, HPLC and spectroscopic data.

EXAMPLE 12

(±)-Calanolide A (1)

In this Example, (±)-calanolide A was prepared in multi-gram scale using the procedure described in Example 7. To a stirring solution of chromanone (±)-7 (51.5 g, 0.14 mol) in ethanol (1.5 L) was added $CeCl_3(H_2O)_7$ (102 g, 274 mmol). The mixture was stirred for 1.5 h at room temperature under $N_2$ and then cooled to −30° C. with an ethylene glycol/$H_2O$ (1:2 w/w) dry ice bath. After the temperature was equilibrated to −30° C., $NaBH_4$ (21.3 g, 563 mmol) was added and stirred at the same temperature for 8.5 h, at which time the reaction was quenched with $H_2O$ (2 L) and extracted with ethyl acetate (2 L×3). The extracts were combined, washed with brine (2 L) and dried over $Na_2SO_4$. The crude product obtained by removal of solvent under reduced pressure was passed through a short silica gel column to provide 53 g of mixture which contained 68% of (±)-calanolide A, 14% of calanolide B and 13% of chromanone (±)-7 as shown by HPLC. This material was subjected to further purification by preparative HPLC to afford pure (±)-calanolide A (1).

EXAMPLE 13

Chromatographic Resolution of Synthetic (±)-Calanolide A

The synthetic (±)-1 was resolved into enantiomers, (+)-calanolide A and (−)-calanolide A, by preparative HPLC[66]. Thus, using a normal phase silica gel HPLC column (250 mm×4.6 mm I.D. Zorbasil, 5 μm particle size, MAC-MOD Analytical, Inc., PA, USA), the synthetic (±)-1 appeared as one peak with a retention time of 10.15 minutes when hexane/ethyl acetate (70:30) was used as the mobile phase at a flow rate of 1.5 minutes and a wavelength of 290 nm was used as the uv detector setting. However, on a chiral HPLC column packed with amnylose carbamate (250 mm×4.6 mm I.D. Chiralpak AD, 10 μm particle size, Chiral Technologies, Inc., PA, USA), two peaks with retention times of 6.39 and 7.15 minutes in a ratio of 1:1 were observed at a flow rate of 1.5 mL/min. The mobile phase was hexane/ethanol (95:5) and the uv detector was set at a wavelength of 254 nm. These two components were separated using a semi-preparative chiral HPLC column, providing the pure enantiomers of calanolide A. The chemical structures of the separated enantiomers, which were assigned based on their optical rotations and compared with the reported natural product, were characterized by spectroscopic data. HPLC chromatograms of (±)-calanolide A and its optical forms are shown in FIG. 1.

(+)-Calanolide A (1): mp 47–50° C. (Lit.[67] 45–48° C.);[α]$_D^{25}$=+68.80° ($CHCl_3$, c 0.7) (Lit.[67] [α]$_D^{25D}$=+66.6°) ($CHCl_3$; c 0.5); $^1H$ NMR ($CDCl_3$) δ1.03 (3H, t, J=7.3 Hz, $CH_3$), 1.15 (3H, d, J=6.8 Hz, $CH_3$), 1.46 (3H, d, J=6.4 Hz, $CH_3$), 1.47 (3H, s, $CH_3$), 1.51 (3H, s, $CH_3$), 1.66 (2H, m, $CH_2$), 1.93 (1H, m, $H_{11}$), 2.89 (2H, m, $CH_2$), 3.52 (1H, d, J=2.9 Hz, OH), 3.93 (1H, m, $H_{10}$), 4.72 (1H, dd, J=7.8 Hz, J=2.7 Hz, $H_{12}$), 5.54 (1H, d, J=9.9 Hz, $H_7$), 5.94 (1H, s, $H_3$), 6.62 (1H, d, J=9.9 Hz, $H_8$); $^{13}C$ NMR ($CDCl_3$) 13.99 ($CH_3$), 15.10 ($CH_3$), 18.93 ($CH_3$), 23.26 ($CH_2$), 27.38 ($CH_3$), 28.02 ($CH_3$), 38.66 ($CH_2$), 40.42 (CH), 67.19 (CH—OH), 77.15 (CH—O), 77.67 (C—O), 104.04 ($C_{4a}$), 106.36 ($C_{8a}$ and $C_{12a}$), 110.14 ($C_3$), 116.51 ($C_8$), 126.97 ($C_7$), 151.14 ($C_{4b}$), 153.10 ($C_{8b}$), 154.50 ($C_{12b}$), 158.88 ($C_4$), 160.42 (C=O); CIMS: 371 (100, M+1), 370 (23.6,M⁺), 353 (66.2, M—OH); 1R: 3611 (w) and 3426 (m, broad, OH), 1734 (vs. C=O), 1643 (m), 1606 (m) and 1587 (vs) $cm^{-1}$; UV $λ_{max}$ (methanol): 204 (32,100), 228 (23,200), 283 (22,200), 325 (12,700) nm; Anal. calcd. for $C_{22}H_{26}O_5$·¼$H_2O$: C, 70.47; H, 7.12; Found: C, 70.64; H, 7.12.

(−)-Calanolide A (1): mp 47–50° C.;[α]$_D^{25}$=75.6° ($CHCl_3$, c 0.7) Lit.[67][α]$_D^{25}$=66.6° ($CHCl_3$, c 0.5); $^1H$ NMR ($CDCl_3$) δ1.03 (3H, t, J=7.4 Hz, $CH_3$), 1.15 (3H, d, J=6.8 Hz, $CH_3$), 1.46 (3H, d, J=6.3 Hz, $CH_3$), 1.47 (3H, s, $CH_3$), 1.51 (3H, s, $CH_3$), 1.66 (2H, m, $CH_2$), 1.93 (1H, m, $H_{11}$), 2.89 (2H, m, $CH_2$), 3.50 (1H, d, J=2.9 Hz, OH), 3.92 (1H, m, $H_{10}$), 4.72 (1H, dd, J=7.8 Hz, J=2.7 Hz, $H_{12}$), 5.54 (1H, d, J=10.0 Hz, $H_7$), 5.94 (1H, s, $H_3$), 6.62 (1H, d, J=10.0 Hz, $H_8$); $^{13}C$ NMR ($CDCl_3$) δ13.99 ($CH_3$), 15.10 ($CH_3$), 18.93 ($CH_3$),23.36 ($CH_2$), 27.38 ($CH_3$), 28.02 ($CH_3$), 38.66 ($CH_2$), 40.42 (CH), 67.19 (CH—OH), 77.15 (CH—O), 77.67 (C—O), 104.04 ($C_{4a}$) 106.36 ($C_{8a}$ and $C_{12a}$), 110.14 ($C_3$), 116.51 ($C_8$), 126.97 ($C_7$), 151.14 ($C_{4b}$), 153.11 ($C_{8b}$), 154.50 ($C_{12b}$), 158.90 ($C_4$), 160.44 (C=O); CIMS: 371 (95.2, M+1), 370 (41.8,M⁺), 353 (100, M—OH); IR: 3443 (m, broad, OH), 1732 (vs, C=O), 1643 (m), 1606 (m) and 1584 (vs) cm$^{-1}$; UV $\lambda_{max}$ (methanol): 200 (20,500), 230 (19,400), 283 (22,500), 326 (12,500) nm; Anal. calcd. for (C$_{22}$ H$_{26}$O$_5$¼H$_2$O: C, 70.47; H, 7.12; Found: C, 7027; H, 7.21.

EXAMPLE 14

Enzymatic Resolution of (±)-Calanouide A

To a magnetically stirred suspension of (±)-calanolide A, prepared by the method of the present invention, and vinyl butyrate (0.1 mL) in hexane (0.5 mL) at ambient temperature was added 1 mg of lipase PS-13 (Pseudomonas Species) (Sigma Corporations, St. Louis, Mo., USA). The reaction mixture was stirred and monitored by conventional means such as TLC analysis. At 10 days, an additional 1 mg of lipase PS-13 was added. After stirring for a total of 20 days, the reaction was stopped because there was no obvious increase in ester formation. The enzyme was filtered out and the filtrate was concentrated to dryness. The residue was analyzed by HPLC (see Example 13), which showed that 21% of (−)-calanolide A had been converted into its butyrate ester form. The enriched (+)calanolide A and the butyrate ester of (−)-calanolide A can be easily separated by conventional means such as column chromatography. The enriched (+)-calanolide A may be repeatedly treated with vinyl butyrate and lipase PS-13 as described above so as to obtain high e.e. of (+)-calanolide A.

EXAMPLE 15

Aldol Reaction (Scheme III) of Chromene 4 in the Presence of LDA

To a stirring solution of chromene 4 (1.0 g, 2.9 mmol) in THF (15 mL) at −78° C. under N$_2$ was added 2 M LDA in THF (3.2 mL, 6.4 mmol). After 1 h at the same temperature, acetaldehyde (1.0 mL, 17.5 mmol) was added via syringe. The reaction was monitored by TLC analysis. After 1 h, the reaction mixture was quenched with a precooled 2 N HCl in methanol (15 mL) and extracted with ethyl acetate (30 mL×3). The combined extracts were washed with brine and dried over Na$_2$SO$_4$. Removal of solvents in vacuo afforded a reddish oil, which was purified by silica gel column chromatography eluting with a discontinuous gradient of 5%, 10%, 15%, 25% and 30% of ethyl acetate in hexane to obtain 780 mg (70% yield) of a mixture of (±)-8a and (±)-8b in a ratio of 1:1, as indicated by $^1$H NMR. Pure samples of (±)-8a and (±)-8b were obtained by carefully collecting the front fractions and later fractions from column chromatography, analytical data of which were described below:

6,6-Dimethyl-9-hydroxy-10-[2(S*)-methyl-3-(R*)-hydroxybutyro]-4-propyl-2H,6H-benzo[1,2-b:3,4-b'] dipyran-2-one [syn-(±)8a]. m.p. 66–67° C.; $^1$H NMR (CDCl$_3$): 1.05 (3H, t, J=7.3 Hz, CH$_3$), 1.30 (3H, d, J=6.0 Hz, CH$_3$), 1.33 (3H, d, J=6.6 Hz, CH$_3$), 1.54 (6H, s, 2 CH$_3$), 1.67 (2H, m, CH$_2$), 2.62 (1H, broad-s, OH), 2.91 (2H, t, J=7.7 Hz, CH$_2$), 3.98 (1H, dq, J=2.7 Hz, J=7.0 Hz, H$_{2'}$), 4.29 (1H, m, H$_{3'}$), 5.59 (1H, d, J=10.0 Hz, H$_7$), 6.01 (1H, S, H$_3$), 6.73 (1H, d, J=10.0 Hz, H$_8$), 14.11 (1H, s, OH); 1H NMR (DMSO-d$_6$): 1.00 (3H, t, J=7.3 Hz, CH$_3$), 1.13 (3H, d, J-6.6 Hz, CH$_3$), 1.16 (3H, d, J=6.8 Hz, CH$_3$), 1.49 (3H, s, CH$_3$), 1.50 (3H, s, CH$_3$), 1.60 (2H, apparent sextet, J=7.6 Hz, CH$_2$), 2.88 (2H, apparent dd, J=6.3 Hz, J=9.0 Hz, CH$_2$), 3.39 (1H, broad-s, OH), 3.68 (1H, dq, J=5.2 Hz, J=6.7 Hz, H$_{2'}$), 3.97 (1H, apparent quintet, J=5.8 Hz, H$_3$), 5.78 (1H, d, J=10.1 Hz, H$_7$), 6.11 (1H, s, H$_3$), 6.63 (1H, d, J=10.1 Hz, H$_8$), 13.25 (1H, S, OH); MS (CI): 388 (36.5, M+2), 387 (100, M+1), 386 (6.6, M$^+$), 369 (21.6, M—OH), 343 (50.7, M—C$_3$H$_7$); UV $\lambda_{max}$ (methanol) nm: 199 (41,000), 270 (25,700), 306 (21,900); IR (KBr) cm$^-$: 3395 (broad, m, OH), 1734 (s) and 1707 (vs) (C=O), 1644 (m), 1608 (vs), 1578 (vs) and 1547 (vs); Anal. Calcd. for C$_{22}$H$_{26}$O$_6$.⅓H$_2$0: C, 67.33; H, 6.84; Found: C, 67.43; H, 6.93.

6,6-Dimethyl-9-hydroxy-10-[2(S*)-methyl-3(S*)-hydroxybutyro]-4-propyl-2H,6H-benzo[1,2-b:3,4-b'] dipyran-2-one [anti-(±)-8b]. m.p. 115° C.; $^1$H NMR (CDCl$_3$): 1.05 (3H, t, J=7.4 Hz, CH$_3$), 1.25 (3H, d, J=6.4 Hz, CH$_3$), 1.29 (3H, d, J=6.9 Hz, CH$_3$), 1.54 (6H, s, 2 CH$_3$), 1.66 (2H, apparent sextet, J=7.6 Hz, CH$_2$), 2.92 (2H, t, J=7.8 Hz, CH$_2$), 2.95 (1H, d, J=5.5 Hz, OH), 3.98 (1H, dq, J=6.1 Hz, J=6.8 Hz, H$_{2'}$ ), 4.22 (1H, apparent sextet, J=6.2 Hz, H$_3$ ), 5.59 (1H, d, J=10.1 Hz, H$_7$), 6.03 (1H, s, H$_3$), 6.73 (1H, d, J=10.1 Hz, H$_8$), 14.25 (1H, s, OH); $^1$H NMR (DMSO-d$_6$): 1.00 (3H, t, J=7.3 Hz, CH$_3$), 1.11 (6H, d, J=6.7 Hz, 2 CH$_3$), 1.49 (3H, s, CH$_3$), 1.50 (3H, s, CH$_3$), 1.60 (2H, apparent sextet, J=7.3 Hz, CH$_2$), 2.85, 2.90 (2H, t-AB type, J=7.7 Hz, J$_{AB}$=21.4 Hz, CH$_2$), 3.59 (1H, apparent quintet, J=7.1 Hz, H$_{2'}$), 3.96 (1H, apparent quintet, J=7.0 Hz, H$_3$), 4.97 (1H, broad-s, OH), 5.78 (1H, d, J=10.1 Hz, H$_7$), 6.10 (1H, s, H$_3$), 6.63 (1H, d, J=10.0 Hz, H$_8$), 12.69 (1H, s, OH); MS (EI): 387 (2.8, M+1), 386 (9.4, M$^+$), 371 (5.3, M—CH$_3$), 369 (1.5, M—OH), 353 (54.0, M—CH$_3$—H$_2$O), 342 (22.5, M—C$_3$H$_7$-1), 327 (100, M—C$_3$H$_7$—OH+1); UV$\lambda_{max}$ (methanol) nm: 199 (41,000), 270 (25,700), 306 (21,900); IR (KBr) cm$^{-1}$: 3478 (broad, m, OH), 1736 (vs) and 1707 (vs) (C=O), 1645 (m), 1603 (vs), 1584 (vs, sh); Anal. Calcd. for C$_{22}$H$_{26}$O$_6$.⅓H$_2$O: C, 67.33; H, 6.84; Found: C, 67.34; H, 6.45.

EXAMPLE 16

Aldol Reaction (Scheme III) of Chromene 4 in the Presence of LDA/TiCl$_4$

In this Example, two procedures are provided for effecting the Aldol reaction. Procedure B was found to be more suitable for scale-up because of simplification of temperature control.

Procedure A. To a stirring solution of chromene 4 (200 mg, 0.58 mmol) in dry methylene chloride (10 mL) at −78° C. under N$_2$ was added 2 M solution of LDA in heptane/THF/ ethyl benzene (0.64 mL, 1.28 mmol). The reaction mixture was stirred at −78° C. for 30 min and then TiCl$_4$ (0.13 mL, 1.17 mmol) was added. The resulting yellow solution was warmed to −40° C. and stirred for 45 min. The mixture was recooled to −78° C., and acetaldehyde (150 mg, 3.5 mmol) was added via syringe. After 4 h, the reaction was quenched by slow addition of pre-cooled saturated NH$_4$Cl (10 mL). Water (3 mL) was added to dissolve the oily solid. The mixture was extracted with ethyl acetate (50 mL×3). The combined extracts were washed with brine (100 mL) and dried over MgSO$_4$. The crude product obtained by evaporation was purified by silica gel column chromatography, eluting with hexanelethyl acetate (5:1) to afford unreacted chromene 4 (30 mg, 15% yield) and syn-(±)8a (140 mg, 61% yield), which contained 7% of anti-(±)-8b as shown by HPLC.

Procedure B. To a stirring solution of chromene 4 (20 g, 58.4 mmol) in dry methylene chloride (300 mL) at −40° C. under N$_2$ was added TiCl$_4$ (19 mL, 175 mmol). The mixture was then cooled to −78° C., followed by slow addition of 2 M solution of LDA in heptane/THF/ethyl benzene (64 mL, 128 mmol). After 30 min at the same temperature, acetaldehyde (9 mL, 175 mmol) was added via syringe. The reaction mixture was stirred at −78° C. for 2 h. TLC analysis (hexane/ethyl acetate, 5:1) indicated that approximately 90% chromene 4 had been converted. The mixture was then poured into pre-cooled saturated NH₄Cl (240 mL). Water (120 mL) was added to dissolve the oily solid and the mixture was stirred for 20 min. Layers were separated and the aqueous solution was extracted with ethyl acetate (600 mL×3). The combined extracts were washed with brine (600 mL) and dried over MgSO₄. Removal of solvents in vacuo afforded a reddish oil (23 g), which was taken up into ether (250 mL). The undissolved residue was filtered and the etheral solution was concentrated to half volume and then slowly added into rapidly stirring hexane cooled at −78° C. Precipitates thus formed were collected by filtration to afford syn-(±)8a (11.1 g, 49% yield), which contained 4% of (±)8b as shown by HPLC.

EXAMPLE 17

Enzymatic Resolution of syn-(±)-8a (Scheme III)

Into a stirring solution of syn-(±)-8a (7.6 g, 19.7 mmol) in tert-butyl methyl ether (130 mL) at ambient temperature under $N_2$ were added successively vinyl acetate (33 mL), 4 Å molecular sieves (17 g) and Lipase PS-30 (3.8 g) (Amano Enzyme U.S.A. Co., Ltd., Troy, Va.). The resulting mixture was vigorously stirred at ambient temperature for 4 days, whereupon it was filtered through celite and the celite was washed with ethyl acetate (20 mL). The crude product obtained from evaporation was subjected to silica gel column chromatography eluting with a discontinuous gradient of 5%, 10%, 15%, 25%, 30% and 40% of ethyl acetate in hexane to afford 4.8 g (63% yield) of the acetate (9), which was contaminated by over-acylation product of (±)-8a, and 2.8 g (37% yield) of pure syn-(±)8a.
6,6-Dimethyl-9-hydroxy-10-[2(R)-methyl-3(S) hydroxybutyro]4-propyl-2H,6H-benzo[1,2-b:3,4-b'] dipyran-2-one [syn-(+)-8a]. m.p. 82–85° C.; $[\alpha]_D^{25}=0°$ (CHCl₃, c 0.7; $[\alpha]_D^{25}=0°$ (CHCl₃, c 0.35); ¹H NMR (CDCl₃): 1.05 (3H, t, J=7.4 Hz, CH₃), 1.31 (3H, d, J=5.6 HZ, CH₃), 1.33 (3H, d, J=6.9 Hz, CH₃), 1.54 (6H, s, 2 CH₃), 1.67 (2H, apparent sextet, J=7.6 Hz, CH₂), 2.75 (1H, broad-s, OH), 2.91 (2H, t, J=7.8 Hz, CH₂), 3.98 (1H, dq, J=2.7 Hz, J=7.0 Hz, $H_2$), 4.30 (1H, dq, J=2.7 Hz, J=6.5 Hz, $H_3$), 5.59 (1H, d, J=10.2 Hz, $H_7$), 6.01 (1H, s, $H_3$), 6.72 (1H, d, J=10.3 Hz, $H_8$), 14.10 (1H, s, OH); ¹³C NMR (CDCl₃): 10.42 (CH₃), 14.00 (CH₃), 20.61 (CH₃), 23.32 (CH₂), 28.31 (2 CH₃), 39.05 (CH₂), 50.93 (CHCO), 68.03 (CH—O), 79.92 (C—O), 102.95 ($C_{8a}$), 103.69 ($C_{4a}$), 106.12 ($C_{10}$), 110.60 ($C_3$), 115.80 ($C_8$), 126.51 ($C_7$), 157.03 and 157.11 ($C_9$ and $C_{10a}$), 158.58 ($C_{4b}$), 159.01 ($C_4$), 163.13 ($CO_2$), 210.61 (C=O); MS (CI): 388 (33.4, M+2), 387 (100, M+1), 386 (8.5, M⁺), 369 (36.3, M—OH), 343 (97.2, M—C₃H₇); Anal. calcd. for $C_{22}H_{26}O_6$: C, 68.38; H, 6.78; Found: C, 68.02; H, 6.62.

EXAMPLE 18

10(R),11(R)-trans-Dihydro-6,6,10,11-tetramethyl-4-propyl-2H,6H,12H-benzo-[1,2-b:3,4b':5,6-b"] tripyran-2,12-dione [Scheme III, (+)-7]

Into a stirring solution of syn-(+)-8a (2.0 g, 5.2 mmol) in THF (50 mL) were added triphenylphosphine (1.9 g, 7.2 mmol) and diethyl azodicaiboxylate (DEAD, 1.2 mL, 7.6 mmol). The resulting reddish solution was stirred at ambient temperature under $N_2$ for 5 h, after which the reaction mixture was quenched with saturated aqueous NH₄Cl (20 mL) and extracted with ethyl acetate (50 mL×3). The combined extracts were washed with brine (50 mL) and dried over Na₂SO₄. The crude product (5.8 g) obtained by evaporation was purified by column chromatography on silica gel eluting with a discontinuous gradient of 10%, 20%, 30% and 40% of ethyl acetate in hexane to afford 1.2 g (63% yield) of pure (+)-7. mp 171–175° C.; $[\alpha]_D^{25}=+37.9°$ (CHCl₃, C 0.73); ¹H NMR [CDCl₃/CD₃OD (3:1)]: 1.06 (3H, t, J=7.3 Hz, CH₃), 1.22 (3H, d, J=7.0 Hz, CH₃), 1.54 (3H, s, CH₃), 1.57 (3H, d, J=6.0 Hz, CH₃), 1.58 (3H, s, CH₃), 1.67 (2H, apparent sextet, J=7.6 Hz, CH₂), 2.59 (1H, dq, J=6.9 Hz, J=11.1 Hz, $H_{11}$), 2.92 (2H, t, J=7.8 Hz, CH₂), 4.37 (1H, dq, J=6.3 Hz, J=11.1 Hz, $H_{10}$), 5.66 (1H, d, J=10.1 Hz, $H_7$), 6.05 (1H, s, $H_3$), 6.67 (1H, d, J=10.1 Hz, $H_8$); ¹³C NMR [CDCl₃/CD₃OD (3:1)]: δ9.87 (CH₃), 13.34 (CH₃), 18.97 (CH₃), 22.85 (CH₂), 27.40 and 27.73 (2 CH₃), 38.38 (CH₂), 46.82 (CHCO), 79.17 (CH—O and C—O), 102.91 ($C_{8a}$), 104.11 ($C_{4a}$), 105.46 ($C_{12a}$), 111.09 ($C_3$), 115.21 ($C_8$), 126.90 ($C_7$), 154.83 and 155.86 ($C_{8b}$ and $C_{12b}$), 157.89 ($C_{4b}$), 158.99 ($C_4$), 160.27 ($CO_2$), 190.50 (C=O); MS (CI): 370 (49.0, M+2), 369 (100, M+1), 368 (17.2, M⁺); Anal. Calcd. for $C_{22}H_{24}O_5$: C, 71.72; H, 6.57; Found: C, 71.46; H, 6.60.
(+)-Calanolide A: To a stirring solution of (+)-7 (660 mg, 1.79 mmol) in ethanol (18 mL) were added CeCl₃(H₂O)₇ (2.7 g, 7.17 mmol) and triphenylphosphine oxide (2.0 g, 7.17 mmol). The mixture was stirred for 1 h at ambient temperature under $N_2$ and then cooled to −30° C. with an ethylene glycol/H₂O (1:2 w/w) dry ice bath. After the temperature was equilibrated to −30° C., NaBH₄ (271 mg, 7.17 mmol) was added and stirred at the same temperature for 5.5 h, at which time the reaction was quenched with saturated NH₄Cl (20 mL) and extracted with ethyl acetate (30 mL×3). The combined extracts were washed with brine (50 mL) and dried over Na₂SO₄. The crude product obtained by removal of solvent under reduced pressure was purified by column chromatography on silica gel eluting with 20% of ethyl acetate in hexane to afford 520 mg (78% yield) of a mixture containing 90% of (+)-calanolide A[(+)-1] and 10% of (+)-calanolide B. (+)-Calanolide A [(+)-1] was further separated from (+)-calanolide B by normal phase HPLC and was identical with an authentic sample.

EXAMPLE 19

Enzymatic Resolution (Scheme IV) of anti-(±)-8b

Into a stirring solution of anti-(±)-8b (3.0 g, 7.8 mmol) in tert-butyl methyl ether (78 mL) at ambient temperature under $N_2$ were added successively vinyl acetate (26 mL), 4 Å molecular sieves (3.0 g) and Lipase PS-30 (1.5 g) (Amano Enzyme U.S.A. Co., Ltd., Troy, Va.). The resulting mixture was vigorously stirred at ambient temperature for 41 h, whereupon it was filtered through the celite and the celite was washed with ethyl acetate (20 mL). The crude yellowish solid product (3.2 g) obtained from evaporation was purified by silica gel column chromatography eluting with a discontinuous gradient of 5%, 10%, 15%, 25%, 30% and 40% of ethyl acetate in hexane to afford 1.68 g (50% yield) of the acetate (10) and 1.37 g (46% yield) of anti-(+)-8b.
6,6-Dimethyl-9-hydroxy-10-[2(S)-methyl-3(S)-hydroxybutyro]-4-propyl-2H,6H-benzo-[1,2-b:3,4-b'] dipyran-2-one [anti-(+)-8b]. m.p. 131–134° C.; $[\alpha]_D^{25}=+45.3°$ (CHCl₃, c 0.72); ¹H NMR (CDCl₃): 1.06 (3H, t, J=7.3 Hz, CH₃), 1.25 (3H, d, J=6.6 Hz, CH₃), 1.29 (3H, d, J=6.7 Hz, CH₃), 1.55 (6H, s, 2 CH₃), 1.67 (2H, apparent sextet, J=7.6 Hz, CH₂), 2.92 (2H, t, J=7.8 Hz, CH₂), 2.96 (1H, d, J=7.1 Hz, OH), 3.98 (1H, apparent quintet, J=6.1 Hz, $H_2$), 4.22 (1H, apparent sextet, J=6.0 Hz, $H_3$), 5.60 (1H, d, J=10.1 Hz, $H_7$), 6.03 (1H, s, $H_3$), 6.73 (1H, d, J=10.1 Hz, H$_8$), 14.25 (1H, s, OH); MS (CI): 388 (41.4, M+2), 387 (100, M+1), 386 (13.0, M$^+$), 369 (42.8, M— OH), 343 (63.8, M—C$_3$H$_7$); Anal. calcd. for C$_{22}$H$_{26}$O$_6$: C, 68.38; H, 6.78; Found: C, 68.50; H, 6.91.

6,6Dimethyl-9-hydroxy-10-[2(R)-methyl-3(R)-acetoxybutyro]-4-propyl-2H,6H-benzo-[1,2-b:3,4-b']dipyran-2one [anti-(+)-10]. m.p. 61–64° C.; [α]$_D^{25}$=+30.0° (CHCl$_3$, c 0.73); $^1$H NMR (CDCl$_3$): 1.06 (3H, t, J=7.2 Hz, CH$_3$), 1.29 (3H, d, J=6.2 Hz, CH$_3$), 1.32 (3H, d, J=6.7 Hz, CH$_3$), 1.54 (6H, s, 2 CH$_3$), 1.67 (2H, apparent sextet, J=7.6 Hz, CH$_2$), 1.93 (3H, s, CH$_3$CO), 2.91 (2H, m, CH$_2$), 4.18 (1H, dq, J=8.3 Hz, J=6.9 Hz, H$_{2'}$), 5.34 (1H, dq, J=8.2 Hz, J=6.4 Hz, H$_{3'}$), 5.59 (1H, d, J=10.1 Hz, H$_7$), 6.02 (1H, s, H$_3$), 6.73 (1H, d, J=10.1 Hz, H$_8$), 14.02 (1H, s, OH); MS (CI): 430 (37.1, M+2), 429 (95.2, M+1), 428 (7.2, M$^+$), 369 (100, M—AcO); Anal. calcd. for C$_{24}$H$_{28}$O$_7$: C, 67.28; H, 6.59; Found: C, 67.75: H, 6.90.

EXAMPLE 20

5,7-Dihydroxy-4-trifluoromethylcoumarin (Scheme V, 11a, R$_1$=CF$_3$, R$_2$=H)

Into a mixture of anhydrous phloroglucinol (8 g, 63.0 mmol) and ethyl 4,4,4-trifluoroacetoacetate (12 g, 65.0 mmol) was added concentrated H$_2$SO$_4$ (11 mL). The resulting mixture was heated at 100° C. and stirred for 2 h, whereupon the reaction mixture was cooled to room temperature. Ice (100 g) and H$_2$O (150 mL) were then added while cooling with ice bath. The precipitated product was collected and dissolved in AcOEt (100 mL), which was washed with H$_2$O and dried over Na$_2$SO$_4$. The crude product (16 g) obtained by evaporation under vacuum was chromatographed in methylene chloridethanol (95:5) to furnish 11a (6 g, 39% yield) along with another unidentified product. 11a: mp 250–252° C. after recrystallization from methylene chloride-hexane. $^1$H NMR (DMSO-d$_6$): 6.30 (1H, s, H$_3$), 6.33 and 6.54 (2H, 2 s, H$_7$ and H$_8$), 10.68 and 10.99 (2H, 2 s, 2 OH); MS (CI) m/z: 246 (100, M$^+$), 226 (14.6, M—HF), 218 (10.0, M—CO), 198 (59.6, M—HF—CO); IR (KBr) cm$^{-1}$: 3537(m, sh) and 3384 (s, broad, OH), 1709 (s, C=O), 1618 (s, C=C—C=O), 1154 (s, C—F); Anal. Calcd. for C$_{10}$H$_5$F$_3$O$_4$: C, 48.80; H, 2.05; Found, C, 48.83; H, 2.10.

EXAMPLE 21

5,7-Dihydroxy-8-isobutyryl-4-propylcoumarin (Scheme V, 12a, R$_1$=n-Pr, R$_2$=H, R$_3$=R$_4$Me)

Into a flame-dried 500 mL 3-necked round-bottom flask was placed 5,7-dihydroxy4-propylcoumarin (2, 10.0 g, 48.1 mmol) and AlCl$_3$ (12.0 g, 90 mmol) under N$_2$. Dichloroethane (120 mL) was then added, and the solution warmed to 75° C. with a water bath with mechanical stirring. After stirring 15 min at 75° C., a homogenous solution was obtained. To this solution was added a mixture of isobutyric anhydride (7.61 g, 48.1 mmol) and AlCl$_3$ (12.0 g) in dichloroethane (60 mL) dropwise over 1 h. After addition was completed, the solution was stirred for an additional 1 h at 75° C., then cooled to room temperature. The solution was poured into a mixture of crushed ice (100 g) and 2 N HCl (100 mL), at which point a white precipitate formed. The mixture was diluted with ethyl acetate (1.8 L), and the organic layer separated. The organic solution was washed sequentially with 1 N HCl (500 mL) and saturated brine (500 mL), dried over magnesium sulfate, filtered and evaporated to provide an orange powder. The powder was triturated with acetone (80 mL), collected on a Büchner funnel, rinsed with diethyl ether (80 mL) and dried to provide a cream colored solid (4.22 g). The product was fuirther purified via recrystallization from ethanol (200 mL) to give colorless plates (3.63 g, 26.0%); mp 263–265° C., with softening at 250° C. (Lit.[65] 272–273° C.); $^1$H NMR (DMSO-d$_6$): 0.95 (3H, t, J=7.4 Hz, CH$_3$), 1.08 (6H, d, J=6.9 Hz, 2 CH$_3$), 1.59 (2H, sextet, J=7.4 Hz, CH$_2$), 2.87 (2H, t, J=7.4 Hz, CH$_2$), 3.24 (1H, heptet, J=6.9 Hz, CH), 5.93 (1H, s, H$_3$), 6.37 (1H, s, H$_6$), 11.16 and 11.44 (2H, 2 s, 2 OH); EIMS: 290 (23.2, M$^+$), 247 (100, M—C$_3$H$_7$), 219 (11.1, M—C$_3$H$_7$CO); IR (KBr) cm$^{-1}$: 3216 (s, OH), 1684 (s, C=O); Anal. calcd. for C$_{16}$H$_{18}$O$_5$: C, 66.20; H, 6.25. Found: C, 66.15; H, 6.21.

EXAMPLE 22

6,6-Dimethyl-9-hydroxy-10-isobutyryl-4-propyl-2H, 6H-benzo[1,2-b:3,4b']dipyran-2-one (Scheme V, 13a, R$_1$=n-Pr, R$_2$=R$_7$=H, R$_3$=R$_4$=R$_5$=Me)

To a solution of 12a (2.90 g, 10.0 mmol) in pyridine (5 mL) was added 4,4dimnethoxy-2-methylbutan-2-ol (1.49 g, 10.1 mmol), and the solution heated to reflux. After heating for 40 h, TLC indicated complete consumption of starting material. The reaction was cooled to room temperature and the pyridine removed in vacuo. The dark colored residue was dissolved in ethyl acetate (50 mL) and washed sequentially with 2 N HCl (50 mL×2), 5% NaHCO$_3$ (50 mL) and saturated brine (50 mL). The solution was dried over magnesium sulfate, filtered and evaporated to provide a dark orange solid, which was chromatographed on a silica gel column (125 g) and eluted with ethyl acetate/hexane (1:4) to afford the pure product as a bright orange crystalline solid (2.51 g, 70.5%), mp 70–72° C.; $^1$H NMR (CDCl$_3$): 1.05 (3H, t, J=7.3 Hz, CH$_3$), 1.26 (6H, d, J=6.7 Hz, 2 CH$_3$), 1.54 (6H, s, 2 CH$_3$), 1.66 (2H, sextet, J=7.7 Hz, CH$_2$), 2.91 (2H, t, J=7.7 Hz, CH$_2$), 4.06 (1H, heptet, J=6.7 Hz, CH), 5.58 (1H, d, J=9.9 Hz, H$_7$), 6.01 (1H, s, H$_3$), 6.73 (1H, d, J=9.9 Hz, H$_8$), 14.45 (1H, s, OH); EIMS: 356 (48.0, M$^+$), 341 (100, M—CH$_3$), 313 (65.0, M—C$_3$H$_7$); IR (KBr) cm$^{-1}$: 1732; Anal. calcd. for C$_{21}$H$_{24}$O$_5$: C, 70.77; H, 6.79. Found: C, 70.73; H, 6.78.

EXAMPLE 23

(±)6,6-Dimethyl-10-(2,2-dimethyl-3-hydroxybutyro)-9-hydroxy4-propyl-2H,6H-benzo[1,2-b:3,4-b']dipyran-2-one (Scheme V, 14a, R$_1$=n-Pr, R$_2$=R$_7$=R$_8$=H, R$_3$=R$_4$=R$_5$=R$_6$=R$_9$=Me)

To a solution of 13a (1.25 g, 3.51 mmol) in anhydrous THF (20 mL) under N$_2$ at −78° C. was added LDA (2.0 M in heptane/THF/ethyl benzene, 4.39 mL, 8.78 mmol) dropwise, and the resulting red solution stirred for 1 h. A solution of acetaldehyde (1.54 g, 35.1 mmol) in THF (6 mL) was added dropwise, and the reaction mixture stirred at −78° C. for 3 hours whereupon the reaction was quenched by slowly adding 2.5 M ethanolic HCl (10 mL), and the solution then allowed to warm to room temperature. The solvent was evaporated in vacuo and the residue partitioned between ethyl acetate (100 mL) and saturated NaHCO$_3$ (100 mL). The organic layer was collected and washed with saturated brine (100 mL), dried over magnesium sulfate, filtered and evaporated to provide a brown solid. The product was triturated with ethyl acetate/hexane (1:1, 15 mL), collected on a Büchner funnel, rinsed with fresh solvent and air dried to give the desired product as a white powder (654 mg, 46.6%). An analytical sample was obtained via recrystallization from ethyl acetate/hexane (1:1); mp 190–191° C.; $^1$H NMR (CDCl$_3$): 1.04 (3H, t, J=7.4

Hz, $CH_3$), 1.25 (3H, s, $CH_3$), 1.29 (3H, d, J=6.4 Hz, $CH_3$), 1.33 (3H, s, $CH_3$), 1.48 (3H, s, $CH_3$), 1.52 (3H, s, $CH_3$), 1.66 (2H, sextet, J=7.5 Hz, $CH_2$), 2.39 (1H, broad-s, OH), 2.88 (m, 2H, $CH_2$), 4.47 (1H, q, J=6.4 Hz, CH), 5.56 (1H, d, J=10.0 Hz, $H_7$), 5.92 (1H, s, $H_3$), 6.64 (1H, d, J=10.0 Hz, $H_8$), 8.99 (1H, s, OH): EIMS: 400 (1.1, $M^+$), 356 (37.5, M—$C_2H_4O$), 341 (100, M—$CH_3$—$C_2H_4O$), 313 (68.2, M—$C_3H_7$—$C_2H_4O$); IR (KBr) $cm^{-1}$: 3246 (broad-s, OH), 1686 (s, C=O); Anal. calcd. for $C_{23}H_{28}O_6$: C, 68.98; H, 7.05. Found. C, 69.03; H, 6.99.

EXAMPLE 24

(±)-6.6-Dimethyl-10(2,3-dimethyl-3-hydroxybutyro)-9-hydroxy-4-propyl-2H,6H-benzo[1,2-b:3,4-b']dipyran-2-one (Scheme V, 14b, $R_1$=n-Pr, $R_2$=$R_3$=$R_7$=H, $R_4$=$R_5$=$R_6$=$R_8$=$R_9$=Me)

To a suspension of 4 (1.2 g, 3.50 mmol) in THF (16 mL) at −78° C. was added a solution of LDA in heptane/THF/ethyl benzene (2 M, 5.0 mL, 10.0 mmol) dropwise under $N_2$. The solution was stirred at −78° C. for 1 h and acetone (2.0 mL, 27.2 mmol) was added quickly via syringe. The solution was stirred at −78° C. for 3 h, quenched with methanolic HCl (2 M, 15 mL) at −78° C., then allowed to warm to room temperature. The reaction mixture was concentrated and partitioned between ethyl acetate (150 mL) and saturated $NaHCO_3$ (100 mL). The organic layer was collected and washed with saturated brine (50 mL), dried over magnesium sulfate, filtered and concentrated to provide a red oil (1.36 g), an analytical sample of which was obtained via silica gel column chromatography (ethyl acetate/hexane, 1:4) as an off-white solid: mp 99–102° C.; $^1$H NMR ($CDCl_3$): 1.05 (3H, t, J=7.3 Hz, $CH_3$), 1.29 (3H, s, $CH_3$), 1.32 (3H, s, $CH_3$), 1.39 (3H, d, J=6.8 Hz, $CH_3$), 1.55 (6H, s, 2 $CH_3$), 1.67 (2H, sextet, J=7.7 Hz, $CH_2$), 2.91 (2H, t, J=7.7 Hz, $CH_2$), 3.52 (1H, broad-s, OH), 4.03 (1H, q, J=6.8 Hz, CH), 5.60 (1H, d, J=9.9 Hz, $H_7$), 6.03 (1H, s, $H_3$), 6.73 (1H, d, J=10.1 Hz, $H_8$), 13.81 (1H, s, OH); EIMS: 401 (5.1, M+1), 400 (21.5, $M^+$), 385 (6.2, M—$CH_3$), 342 (38.9, M—$C_2H_7O$+1), 327 (100, M—$CH_3$—$C_3H_7O$+1); IR (KBr) $cm^{-1}$: 3547 (w, OH), 3449 (vw, broad, OH), 1734 (vs, C=O); Anal. calcd. for $C_{23}H_{28}O_6$: C, 68.98; H, 7.04. Found: C, 68.98; H, 7.04.

EXAMPLE 25

(±)-syn and (±)-anti-6,6-Dimethyl-9-hydroxy-10(2-methyl-3-hydroxypentanoyl)-4-propyl-2H,6H-benzo[1,2-b:3,4-b']dipyran-2-one (Scheme V, 14c, $R_1$=n=Pr, $R_2$=$R_3$=$R_7$=$R_8$=H, $R_4$=$R_5$=$R_6$=Me, $R_9$=Et)

To a solution of 4 (1.75 g, 5.1 1 mmol) in THF (27.0 mL) at −78° C. was added dropwise a solution of LDA in heptane/THF/ethyl benzene (2 M, 7.0 mL, 14.0 mmol) under $N_2$. The solution was stirred at −78° C. for 1 h, and propionaldehyde (2.2 mL, 31.2 mmol) was added quickly via syringe. The solution was stirred at −78° C. for 3 h, quenched with methanolic HCl (2 M, 25 mL) at −78° C., then warmed to room temperature. The mixture was extracted with ethyl acetate (350 mL), washed sequentially with 150 mL each of saturated $NaHCO_3$ and saturated brine, dried over magnesium sulfate, filtered and concentrated to provide a diastereomeric mixture of the product as a red oil (2.44 g, 100%), which was not further purified and used for the next step.

EXAMPLE 26

(±)-10,11-Dihydro-6,6,10,11,11-pentamethyl-4-propyl-2H,6H, 12H-benzo[1,2-b:3,4-b':5,6b"]tripyran-2,12-dione (Scheme V, 15a, $R_1$=n-Pr, $R_2$=$R_7R_8$=H, $R_3$=$R_4$=$R_5$=$R_6$=$R_9$=Me)

To a solution of 14a (0.5 g, 1.25 mmol) and triphenylphosphine (492 mg, 1.88 mmol) in THF (10 mL) was added a solution of diethyl azodicarboxylate (327 mg, 1.88 mmol) in THF (2 mL) dropwise under $N_2$. The reaction mixture was stirred for 2.5 h, after which it was poured into saturated $NH_4Cl$ (100 mL). The solution was extracted with ethyl acetate (100 mL), and the separated organic layer washed sequentially with $H_2O$ (100 mL) and saturated brine (100 mL). After drying over magnesium sulfate, the solution was filtered and concentrated in vacuo to provide a yellow oil. Column chromatography through 75 g silica gel (ethyl acetate/hexane, 1:2) provided the desired product as a white crystalline solid (449 mg, 94.0%). An analytical sample was obtained via recrystallization from ethyl acetatelhexane (2:1): mp 157° C.; $^1$H NMR ($CDCl_3$): 1.03 (3H, t, J=7.3 Hz, $CH_3$), 1.09 (3H, s, $CH_3$), 1.19 (3H, s, $CH_3$), 1.43 (3H, d, J=6.5 Hz, $CH_3$), 1.53 (3H, s, $CH_3$), 1.55 (3H, s, $CH_3$), 1.64 (2H, sextet, J=7.7 Hz, $CH_2$), 2.88 (2H, t, J=7.7 Hz, $CH_2$), 4.34 (1H, q, J=6.4 Hz, $H_{10}$), 5.60 (1H, d, J=10.0 Hz, $H_7$), 6.04 (1H, s, $H_3$), 6.66 (1H, d, J=10.0 Hz, $H_8$); EIMS: 382 (60.8, $M^+$), 367 (100, M—$CH_3$), 312 (50.3 (M—$C_5H_{10}$), 297 (74.5, M—$CH_3$—$C_5H_{10}$); IR (KBr) $cm^{-1}$: 1730 (vs, C=O); Anal. calcd. for $C_{23}H_{26}O_5$: C, 72.23; H, 6.85. Found: C, 72.35; H, 6.90.

EXAMPLE 27

(±)10,11-Dihydro-6,6,10,10,11-pentamethyl-4-propyl-2H, 6H, 12H-benzo[1,2-b:3,4b':5,6b"]tripyran-2,12-dione (Scheme V, 15b, $R_1$=n-Pr, $R_2$=$R_3$=$R_7$=H, $R_4$=$R_5$=$R_6$=$R_8$=$R_9$=Me)

To a solution of crude 14b (980 mg, 2.19 mmol) and triphenylphosphine (859.0 mg, 3.28 mmol) in THF (15 mL) was slowly added diethyl azodicarboxylate (DEAD, 0.50 mL, 3.17 mmol) under $N_2$. The red solution was stirred for 2.5 h at room temperature, then quenched with saturated $NH_4Cl$ (10 mL). The solution was extracted with ethyl acetate (200 mL), washed sequentially with 50 mL each of $H_2O$ and saturated brine, dried over magnesium sulfate, filtered and concentrated to provide a yellow residue (2.37 g). Purification by silica gel column chromatography (ethyl acetatelhexane, 1:10) provided, after overnight drying under high vacuum in the presence of $P_2O_5$, the desired product as an off-white solid (373.7 mg, 44.6%): mp 140–141° C.; $^1$H NMR ($CDCl_3$): 1.03 (3H, t, J=7.3 Hz, $CH_3$), 1.19 (3H, d, J=7.0 Hz, $CH_3$), 1.34 (3H, s, $CH_3$), 1.53 (6H, s, 2 $CH_3$), 1.55 (3H, s, $CH_3$), 1.65 (2H, sextet, J=7.8 Hz, $CH_2$), 2.72 (1H, q, J=7.0 Hz, $H_{11}$), 2.85–2.91 (2H, m, $CH_2$), 5.60 (1H, d, J=10.1 Hz, $H_7$), 6.03 (1H, s, $H_3$), 6.65 (1H, d, J=10.0 Hz, $H_8$); EIMS: 382 (61.2, $M^+$), 367 (82.0, M—$CH_3$), 312 (46.0, M—$C_5H_{10}$), 297 (100, M—$CH_3$—$C_5H_{10}$); IR (KBr) $cm^{-1}$: 1728 (vs, C=O); Anal. calcd. for $C_{23}H_{26}O_5$: C, 72.23; H, 6.85. Found: C, 71.95; H, 6.88.

EXAMPLE 28

(±)-10,11-trans-10,11-Dihydro-10-ethyl-4-propyl-6,6,11-trimethyl-2H,6H,12H-benzo[1,2-b:3,4-b"]tripyran-2,12-dione (15c) and (±)-10,11-cis-10,11-dihydro-10-ethy-4-propyl-6,6,11-trimethyl-2H,6H, 12H-benzo[1,2b:3,4-b':5,6-b"]tripyran-2,12-dione (15d, Scheme V)

To a solution of 14c (2.44 g, 5.11 mmol) and triphenylphosphine (1.96 mg, 7.48 mmol) in THF (30.0 mL) was slowly added diethyl azodicarboxylate (DEAD, 1.16 mL, 7.37 mmol) under $N_2$. The red solution was stirred for 2.5 h at room temperature, then quenched with saturated $NH_4Cl$ (22 mL). The solution was warmed to room temperature and extracted with ethyl acetate (400 mL), washed with $H_2O$ (100 mL) and brine (100 mL) and dried over magnesium sulfate. After filtration, the solution was concentrated in vacuo to provide a yellow residue (5.75 g). The crude product was purified by repetitive silica gel column chromatography (3X) using ethyl acetate/hexane (1:4.5) as eluent. The desired fractions were combined, concentrated in vacuo and dried under high vacuum overnight in the presence of $P_2O_5$ to afford 15c (765.4 mg, 39.2%) and 15d (350.4 mg, 17.9%).

15c ($R_1$=n—Pr, $R_2$=$R_4$=$R_7$=$R_8$=H, $R_3$=$R_5$=$R_6$=Me, $R_9$=Et): mp 155–158° C.; $^1$H NMR (CDCl$_3$): 1.03 (3H, t, J=7.4 Hz, CH$_3$), 1.13 (3H, t, J=7.4 Hz, CH$_3$), 1.22 (3H, d, J=6.9 Hz, CH$_3$), 1.53 (3H, s, CH$_3$), 1.56 (3H, s, CH$_3$), 1.64 (2H, sextet, J=7.6 Hz, CH$_2$), 1.78–1.95 (2H, m, CH$_2$), 2.62 (1H, dq, J=10.4 Hz, J=7.0 Hz, H$_{11}$), 2.88 (2H, t, J=7.7 Hz,CH$_2$), 4.14 (1H, ddd, J=3.5 Hz, J=7.8 Hz, J=10.7 Hz, H$_{10}$), 5.61 (1H, d, J=10.0 Hz, H$_7$), 6.04 (1H, s, H$_3$), 6.66 (1H, d, J=10.0 Hz, H$_8$); EIMS: 382 (37.2, M$^+$), 367 (100, M—CH$_3$), 297 (47.2, M—CH$_3$—C$_5$H$_{10}$); IR (KBr) cm$^{-1}$: 1738 (vs, C=O); Anal. calcd. for $C_{23}H_{26}O_5$: C, 72.23; H, 6.85. Found: C, 71.75; H. 7.02.

15d ($R_1$=n-Pr, $R_2$=$R_3$=$R_7$=$R_8$=H, $R_4$=$R_5$=$R_6$=Me, $R_9$=Et): mp 100–102° C.; $^1$H NMR (CDCl$_3$): 1.03 (3H, t, J=7.3 Hz, CH$_3$), 1.07 (3H, t, J=7.4 Hz, CH$_3$), 1.14 (3H, d, J=7.3 Hz, CH$_3$), 1.54 (3H, s, CH$_3$),1.55 (3H, CH$_3$), 1.65 (2H, sextet, J=7.6 Hz, CH$_2$),1.83–1.98 (2H, m, CH$_2$), 2.70 (1H, dq, J=3.2 Hz, J=7.3 Hz, H$_{11}$), 2.88 (2H, t, J=7.6 Hz, CH$_2$), 4.39 (1H, ddd, J=3.4 Hz, J=5.3 Hz, J=8.8 Hz, H$_{10}$), 5.60 (1H, d, J=10.0 Hz, H$_7$), 6.05 (1H, s, H$_3$), 6.66 (1H, d, J=10.0 Hz, H$_8$); EIMS: 382 (55.0, M$^+$), 367 (100, M—CH$_3$), 297 (52.7, M—CH$_3$—C$_5$H$_{10}$); IR (KBr) cm$^{-1}$: 1732 (vs, C=O); Anal. calcd. for $C_{23}H_{26}O_5$: C, 72.23; H, 6.85. Found: C, 71.80; H, 6.97.

EXAMPLE 29

(±)-10,12cis-10,11-Dihydro-12-hydroxy-6,6,10,11, 11-pentamethyl-4-propyl-2H, 6H, 12H-benzol[1,2-b:3,4b':5,6-b"]tripyran-2-one (16a) and (±)-10,12-trans-10,11dihydro-12-hydroxy-6,6,10,11,11-pentamethyl-4-propyl-2H,6H,12H-benzo[1,2-b:3, 4b':5,6-b"]tripyran-2one (16b, Scheme V)

To a solution of 15a (252 mg, 0.661 mmol) in ethanol/THF (1:1, 8 mL) was added sodium borohydride (25.1 mg, 0.661 mmol) and the solution stirred at room temperature for 30 minutes. The reaction was quenched by the addition of water (1 mL), and the solvent then removed in vacuo. The residue was partitioned between 20 mL each of ethyl acetate and 1 M HCl, and the organic phase separated and washed sequentially with 5% NaHCO$_3$ and saturated brine. After drying over magnesiumn sulfate, the solution was evaporated to give the product as a pale-yellow foam. TLC analysis (ethyl acetate/hexane, 1:2) showed the two epimeric alcohols 16a and 16b at R$_f$ 0.30 amd 0.25, as well as a minor impurity at R$_f$ 0.55. Separation via column chromatography (75 g silica gel, ethyl acetate/hexane, 1:2) provided 16a (127.7 mg, 50.3%) and 16b (18.8 mg, 7.4%) as a white foamn and an off-white waxy solid, respectively.

16a ($R_1$=n-Pr, $R_2$=$R_7$=$R_8$=H, $R_3$=$R_4$=$R_5$=$R_6$=$R_9$=Me): $^1$H NMR (CDCl$_3$): 1.04 (3H, t, J=7.3 Hz, CH$_3$), 1.06 (6H, s, 2 CH$_3$), 1.40 (3H, d, J=6.7 Hz, CH$_3$), 1.47 (3H, s, CH$_3$), 1.50 (3H, s, CH$_3$), 1.66 (2H, sextet, J=7.3 Hz, CH$_2$), 2.80–2.99 (2H, m, CH$_2$), 3.39 (1H, d, J=3.2 Hz, OH), 3.99 (1H, q, J=6.7 Hz, H$_{10}$), 4.70 (1H, d, J=3.2 Hz, H$_{12}$), 5.54 (1H, d, J=9.9 Hz, H$_7$), 5.94 (1H, s, H$_3$), 6.63 (1H, d, J=9.9 Hz, H$_8$); EIMS: 384 (59.0, M$^+$), 369 (100, M—CH$_3$), 314 (44.7, M—C$_5$H$_{10}$), 299 (88.8, M—CH$_3$—C$_5$H$_{10}$); IR (KBr) cm$^{-1}$: 3432 (broad-s, OH), 1734 (vs, C=O); Anal. calcd. for $C_{23}H_{28}O_5$: C, 71.85; H, 7.34. Found: C, 71.74; H, 7.43.

16b ($R_1$=n-Pr, $R_2$=$R_7$=$R_8$=H, $R_3$=$R_4$=$R_5$=$R_6$=$R_9$=Me): $^1$H NMR (CDCl$_3$): 0.78 (3H, s, CH$_3$), 1.04 (3H, t, J=7.3 Hz, CH$_3$),1.11 (3H, s, CH$_3$), 1.36 (3H, d, J=6.5 Hz, CH$_3$), 1.49 (6H, s, 2 CH$_3$), 1.64 (2H, m, CH$_2$), 2.47 (1H, broad-s, OH), 2.89 (2H, m, CH$_2$), 4.35 (1H, q, J=6.5 Hz, H$_{10}$), 4.63 (1H, broad-s, H$_{12}$), 5.54 (1H, d, J=9.8 Hz, H$_7$), 5.96 (1H, s, H$_3$), 6.65 (1H, d, J=9.8 Hz, H$_8$); EIMS: 384 (40.7, M$^+$), 369 (100, M—CH$_3$), 314 (13.5, M—C$_5$H$_{10}$), 299 (48.4, M—CH$_3$—C$_5$H$_{10}$); Anal. calcd. for $C_{23}H_{28}O_5$: C, 71.85; H, 7.34. Found: C, 71.79; H, 7.49.

EXAMPLE 30

(±)11,12cis-10,11-Dihydro-12-hydroxy-6,6,10,10, 11-pentamethyl-4-propyl-2H, 6H, 12H-benzo[1,2-b:3,4-b':5,6-b"]tripyran-2-one (16c) and (±)11,12-trans-10,11-dihydro-12-hydroxy-6,6,10,10,11-pentamethyl-4-propyl-2H,6H,12H-benzo[1,2-b:3,4-b':5,6-b"]tripyran-2-one (16d, Scheme V)

To a solution of 15b (289.7 mg, 0.75 mmol), triphenylphosphine oxide (927.0 mg, 3.33 mmol) and CeCl$_3$ (H$_2$O)$_7$ (842.0 mg, 2.25 mmol) in ethanol (15 mL) at 0° C. was slowly added NaBH$_4$ (195.0 mg, 5.15 mmol) under N$_2$. The suspension was stirred for 1 h at room temperature, then quenched with saturated NH$_4$Cl (30 mL). The solution was extracted with ethyl acetate (200 mL), washed with brine (50 mL), dried over magnesium sulfate, filtered and concentrated to afford a pink crystalline solid (1.38 g). Silica gel column chromatography (ethyl acetate/hexane, 1:5) provided 16c (100.0 mg, 34.3%) as off-white foam and 16d which was further purified by preparative TLC (silica gel, diethyl ether/hexane, 2:1) as off-white foam (56.0 mg, 19.2%).

16c ($R_1$=n-Pr, $R_2$=$R_3$=$R_7$=H, $R_4$=$R_4$=$R_6$=$R_8$=$R_9$=Me): mp 44–45° C.; $^1$H NMR (CDCl$_3$): 1.04 (3H, t, J=7.3 Hz, CH$_3$), 1.24 (3H, d, J=7.1 Hz, CH$_3$), 1.38 (3H, s, CH$_3$), 1.45 (3H, s, CH$_3$), 1.47 (3H, s, CH$_3$), 1.51 (3H, s, CH$_3$), 1.66 (2H, sextet, J=7.3 Hz, CH$_2$), 1.96–2.04 (1H, m, H$_{11}$), 2.8–3.0 (2H, m, CH$_2$), 3.02 (1H, d, J=4.0 Hz, OH), 4.94 (1H, t, J=4.2 Hz, H$_{12}$), 5.53 (1H, d, J=10.0 Hz, H$_7$), 5.94 (1H, s, H$_3$), 6.65 (1H, d, J=9.9 Hz, H$_8$); EIMS: 385 (22.1, M+1), 384 (61.8, M$^+$), 369 (71.1, M—CH$_3$), 351 (29.5, M—CH$_3$—H$_2$O), 299 (100, M—CH$_3$—C$_5$H$_{10}$); IR (KBr) cm$^{-1}$: 3451 (broad-m, OH), 1709 (s, C=O); Anal. calcd. for $C_{23}H_{28}O_5$: C, 71.85; H, 7.33. Found: C, 71.63; H, 7.64.

16d ($R_1$=n-Pr, $R_2$=$R_4$=$R_7$=H, $R_3$=$R_5$=$R_6$=$R_8$=$R_9$=Me): mp 40–42° C.; $^1$H NMR (CDCl$_3$): 1.04 (3H, t, J=7.3 Hz, CH$_3$), 1.13 (3H, d, J=7.0 Hz, CH$_3$), 1.21 (3H, s, CH$_3$), 1.46 (3H, s, CH$_3$), 1.48 (3H, s, CH$_3$), 1.52 (3H, s, CH$_3$), 1.67 (2H, sextet, J=7.6 Hz, CH$_2$), 2.03 (1H, quintet, J=7.2 Hz, H$_{11}$), 2.8–3.0 (2H, m, CH$_2$), 3.66 (1H, s, OH), 4.69 (1H, d, J=7.4 Hz, H$_{12}$), 5.54 (1H, d, J=10.0 Hz, H$_7$), 5.94 (1H, s, H$_3$), 6.63 (1H, d, J=9.9 Hz, H$_8$); EIMS: 385 (8.7, M+1), 384 (36.0, M$^+$), 369 (65.8, M—CH$_3$), 351 (17.6, M—CH$_3$—H$_2$O), 299 (100, M—CH$_3$—C$_5$H$_{10}$); IR (KBr) cm$^{-1}$: 3437 (w, OH), 1734 (s, C=O); Anal. calcd. for $C_{23}H_{28}O_5$: C, 71.85; H, 7.33. Found: C, 71.70; H, 7.56.

EXAMPLE 31

(±)-10,11-trans-11,12-cis-10,11-Dihydro-10-ethyl-12-hydroxy-4-propyl-6,6,11-trimethyl-2H,6H,12H-benzo[1,2-b:3,4-b':5,6-b"]tripyran-2one (16e) and (±)-10,11-trans-11,12-trans-10,11-dihydro-10-ethyl-12-hydroxy-4-propyl-6,6,11-trimethyl-2H,6H,12H-benzo[1,2-b:3,4-b':5,6-b"]tripyran-2-one (16f, Scheme V)

To a suspension of 15c (454.7 mg, 1.19 mmol), triphenylphosphine oxide (1.38 g, 4.96 mmol) and CeCl$_3$(H$_2$O)$_7$ (1.21 g, 3.25 mmol) in ethanol (10 mL) at 0° C. was slowly added NaBH$_4$ (312.0 mg, 8.25 mmol) under N$_2$. The suspension was stirred for 3 h at room temperature. The reaction mixture was quenched with saturated NH$_4$Cl (15 mL), extracted with ethyl acetate (100 mL×3), washed with brine (50 mL), dried over magnesium sulfate, filtered and concentrated to provide pink crystals (1.97 g). Silica gel column chromatography (ethyl acetate/hexane, 1:4) afforded a yellow oil, which consisted of mixture of 16e and 16f (261.0 mg). The compounds were separated using preparative HPLC (normal phase, ethyl acetatethexane, 3:7). The desired fractions were combined and concentrated in vacuo and dried overnight under high vacuum in the presence of P$_2$O$_5$ to afford 16e (yellow oil, 46.5 mg, 10.1%) and 16f (white solid, 137.6 mg, 30.1%).

16e (R$_1$=n-Pr, R$_2$=R$_4$=R$_7$=R$_8$=H, R$_3$=R$_5$=R$_6$=Me, R$_9$=Et): $^1$H NMR (CDCl$_3$): 1.03 (3H, t, J=7.3 Hz, CH$_3$),1.10 (3H, t, J=7.6 Hz, CH$_3$). 1.13 (3H, d, J=6.8 Hz, CH$_3$), 1.48 (3H, s, CH$_3$), 1.49 (3H, s, CH$_3$), 1.65 (2H, sextet, J=7.4 Hz, CH$_2$), 1.76–1.98 (3H, m, CH$_2$+H$_{11}$), 2.80–2.92 (3H, m, CH$_2$+OH), 4.10 (1H, ddd, J=2.9 Hz, J=7.9 Hz, J=10.7 Hz, H$_{10}$), 4.98 (1H, d, J=3.3 Hz, H$_{12}$), 5.54 (1H, d, J=9.9 Hz, H$_7$), 5.94 (1H, s, H$_3$), 6.63 (1H, d, J=9.9 Hz, H$_8$); EIMS: 385(10.5, M+1), 384 (35.8,M$^+$), 369 (78.4, M—CH$_3$), 366 (43.1, M—H$_2$O), 351 (39.0, M—CH$_3$—H$_2$O), 337 (100, M—H$_2$O— C$_2$H$_5$), 299 (37.7, M—CH$_3$—C$_5$H$_{10}$); IR (neat, thin film) cm$^{-1}$: 3432 (w, OH), 1709 (s, C=O); Anal. calcd. for C$_{23}$H$_{28}$O$_5$.¼H$_2$O: C, 71.02; H, 7.38. Found: C, 71.10; H, 7.40.

16f (R$_1$=n-Pr, R$_2$=R$_4$=R$_7$=R$_8$=H, R$_3$=R$_5$=R$_6$=Me, R$_9$=Et): mp 103–105° C.; $^1$H NMR (CDCl$_3$): 1.04 (3H, t, J=7.3 Hz, CH$_3$),1.07 (3H, t, J=7.4 Hz, CH$_3$), 1.13 (3H, d, J=6.9 Hz, CH$_3$), 1.47 (3H, s, CH$_3$), 1.51 (3H, s, CH$_3$), 1.66 (2H, sextet, J=7.6 Hz, CH$_2$), 1.79–1.90 (2H, m, CH$_2$), 2.05 (1H, m, H$_{11}$), 2.90 (2H, m, CH$_2$), 3.53 (1H, s, OH), 3.78 (1H, dt, J=4.1 Hz, J=8.1 Hz, H$_{10}$), 4.73 (1H, d, J=6.7 Hz, H$_{12}$), 5.54 (1H, d, J=10.0 Hz, H$_7$), 5.95 (1H, s, H$_3$), 6.63 (1H, d, J=9.9 Hz, H$_8$); EIMS: 385 (7.6, M+1), 384 (31.1, M$^+$), 369 (100, M—CH$_3$), 351 (9.5, M—CH$_3$—H$_2$O), 337 (11.5, M—H$_2$O—C$_2$H$_5$), 299 (36.9, M—CH$_3$—C$_5$H$_{10}$); IR (KBr) cm$^{-1}$: 3493, 3435 and 3250 (w, OH), 1699 (s, C=O); Anal. calcd. for C$_{23}$H$_{28}$O$_5$: C, 71.85; H, 7.33. Found: C, 71.46; H, 7.34.

EXAMPLE 32

(±)-10,11-cis-11,12-trans-10,11-Dihydro-10-ethyl-12-hydroxy-4-propyl-6,6,11-trimethyl-2H,6H,12H-benzo[1,2-b:3,4-b':5,6-b"]tripyran-2-one (16g) and (±)-10,11,12-cis-10,11-dihydro-10-ethyl-12-hydroxy-4-propy-6,6,11-trimethyl-2H,6H,1 2H-benzo[1,2-b:3,4-b':5,6b"]tripyran-2-one (16h, Scheme V)

To a solution of 15d (290.5 mg,0.76 mmol) in ethanol (15 mL) at 25° C. was added NaBH$_4$ (269.0 mg, 7.11 mmol) portionwise under N$_2$. The suspension was stirred for 1 h at room temperature, then quenched with saturated NH$_4$Cl (6 mL). The solution was extracted with ethyl acetate (200 mL), washed with brine (80 mL), dried over magnesium sulfate, filtered and concentrated to provide a pink residue (455.8 mg). The crude product was purified by silica gel preparative TLC (ethyl acetatelhexane, 2:1). The desired bands were scraped, combined, extracted, concentrated in vacuo and dried under high vacuum overnight in the presence of P$_2$O$_5$ to afford the desired products 16g (229 mg, 78% yield) with 95% purity as indicated by HPLC and 16h (55.9 mg, 19% yield) with 92% purity. The analytical samples were obtained by further purification via preparative HPLC (normal phase, ethyl acetate/hexane, 3:7).

16g (R$_1$=n-Pr, R$_2$=R$_3$=R$_7$=R$_8$=H, R$_4$=R$_5$=R$_6$=Me, R$_9$=Et): $^1$H NMR (CDCl$_3$): 1.03 (3H, t, J=7.4 Hz, CH$_3$), 1.04 (3H, t, J=7.3 Hz, CH$_3$),1.12 (3H, d, J=7.1 Hz, CH$_3$), 1.49 (3H, s, CH$_3$), 1.66 (2H, sextet, J=7.3 Hz, CH$_2$), 1.8–2.0 (2H, m, CH$_2$), 2.3–2.4 (1H, m, H$_{11}$), 2.8–3.0 (2H, m, CH$_2$), 3.30 (1H, s, OH), 4.06 (1H, dt, J=10.1 Hz, J=3.3 Hz, H$_{10}$), 5.10 (1H, d, J=5.2 Hz, H$_{12}$), 5.55 (1H, d, J=10.0 Hz, H$_7$), 5.94 (1H, s, H$_3$), 6.63 (1H, d,J=10.0 Hz, H$_8$); EIMS: 385 (6.3, M+1), 384 (27.3, M$^+$), 369 (100, M—CH$_3$), 351 (6.8, M—CH$_3$—H$_2$O), 337 (4.2, M—H$_2$O—C$_2$H$_5$), 299 (34.7, M—CH$_3$—C$_5$H$_{10}$); IR (KBr) cm$^{-1}$: 3449 (m, OH), 1734 (vs, C=O); Anal. calcd. for C$_{23}$H$_{28}$O$_5$: C, 71.85; H, 7.33. Found: C, 71.79; H, 7.39.

16h R$_1$=n-Pr, R$_2$=R$_3$=R$_7$=R$_8$=H, R$_4$=R$_5$=R$_6$=Me, R$_9$=Et): $^1$H NMR (CDCl$_3$): 0.79 (3H, d, J=7.3 Hz, CH$_3$), 1.04 (3H, t, J=7.3 Hz, CH$_3$), 1.11 (3H, t, J=7.3 Hz, CH$_3$), 1.49 (3H, s, CH$_3$), 1.51 (3H, s, CH$_3$), 1.67 (2H, sextet, J=7.4 Hz, CH$_2$), 1.92 (2H, m, CH$_2$), 2.10 (1H, tq, J=2.0 Hz, J=7.3 Hz, H$_{11}$), 2.79 (1H, s, OH), 2.81–2.90 (2H, m, CH$_2$), 4.23 (1H, ddd, J=1.9 Hz, J=5.4 Hz, J=8.7 Hz, H$_{10}$), 4.87 (1H, d,J=1.9 Hz, H$_{12}$), 5.54 (1H, d, J=10.0 Hz, H$_7$), 5.96 (1H, s, H$_3$), 6.66 (1H, d, J=9.9 Hz, H$_8$); EIMS: 385 (6.1, M+1), 384 (26.0, M$^+$), 369 (100, M—CH$_3$), 351 (9.8, M—CH$_3$—H$_2$O), 337 (8.2, M—H$_2$O—C$_2$H$_5$), 299 (17.6, M—CH$_3$—C$_5$H$_{10}$); IR (neat, thin film) cm$^{-1}$: 3410 (w, OH), 1732 (s, C=O).

EXAMPLE 33

(±)10,11-trans-4-Propyl-7,8,10,11-tetrahydro-6,6,10,11-tetramethyl-2H,6H,12H-benzo[1,2-b:3,4-b':5,6-b"]tripyran-2,12-dione (Scheme VI, 18a, R$_1$=n-Pr, R$_2$=R$_4$=R$_7$R$_8$=H, R$_3$=R$_5$=R$_6$=R$_9$=Me)

To a solution of (±)-7 (534 mg, 1.45 mmol) in ethanol/methylene chloride (1:1, 50 mL, Parr apparatus) under N$_2$ was added 10% palladium/carbon (53.4 mg) at ambient temperature. The mixture was shaken under hydrogen (2 atm) for 1 h, then gravity filtered through Whatmann filter paper. The solvent was evaporated to give a white crystalline solid which was filtered through a short plug of silica gel, eluting with methylene chloride/methanol (97:3). The pure compound (±)-18a (441 mg, 82.2%) was obtained as white plates by recrystallization from ethyl acetate: mp 165° C.; $^1$H NMR (CDCl$_3$): 1.01 (3H, t, J=7.3 Hz, CH$_3$),1.21 (3H, d, J=6.8 Hz, CH$_3$), 1.42 (3H, s, CH$_3$), 1.44 (3H, s, CH$_3$), 1.53 (3H, d, J=6.2 Hz, CH$_3$), 1.61 (2H, sextet, J=7.5 Hz, CH$_2$), 1.84 (2H, apparent dt, J=2.4 Hz, J=6.7 Hz, CH$_2$), 2.53 (1H, dq, J=11.2 Hz, J=6.8 Hz, H$_{11}$), 2.69 (2H, apparent dt, J=3.4 Hz, J=6.7 Hz, CH$_2$), 2.88 (2H, t, J=7.5 Hz, CH$_2$), 4.28 (1H, dq, J=11.2 Hz, J=6.2 Hz, H$_{10}$), 6.02 (1H, s, H$_3$); EIMS: 371 (40.8, M+1); 370 (100, M$^+$), 314 (99.3, M—C$_4$H$_8$),299 (21.6, M—C$_5$H$_{10}$−1), 286 (65.0, M—CH$_3$—C$_5$H$_{10}$+1), 271 (20.5, M—CH$_3$—C$_5$H$_8$O),259 (47.5, M—C$_4$H$_8$—C$_3$H$_4$O+ 1); IR (KBr) cm$^{-1}$: 1740 (vs, C=O); Anal. calcd. for C$_{22}$H$_{26}$O$_5$: C, 71.33; H,7.07. Found: C, 71.00; H, 7.22.

EXAMPLE 34

(±)10,11-trans-10,11-Dihydro-4-propyl-6,6,10,11-tetramethyl-2H, 6H, 12H-benzo[1,2-b:3,4-b':5,6b"] tripyran-2,12-dione-12-oxime (Scheme VI, 19a, R$_1$=n-Pr, R$_2$=R$_4$=R$_7$=R$_8$=H, R$_3$=R$_5$=R$_6$R$_9$=Me, R$_{10}$=H)

Into a 100 mL one-necked round-bottom flask was placed (±)-7 (1.47 g, 4.00 mmol) and NH$_2$OH.HCl (1.39 g, 20.0 mmol). To this mixture was added methanol (60 mL), and the solution heated to reflux with magnetic stirring until the ketone dissolved. Solid K$_2$CO$_3$ powder (1.38 g, 10.0 mmol)

was then carefully added, and the reaction allowed to stir at reflux for 4 hours. The solution was cooled at room temperature, filtered to remove the $K_2CO_3$ and evaporated in vacuo, to provide a yellow solid. The residue was partitioned between 150 mL each of $H_2O$ and ethyl acetate. The organic phase was collected and washed sequentially with 1 N HCl and saturated brine, then dried over magnesium sulfate, filtered and evaporated to afford a thick yellow syrup, which was purified via silica gel column chromatography (75 g), eluting with methylene chloride/methanol (97:3) to afford the desired product as a white solid (657 mg, 43%). An analytical sample was obtained via recrystallization from acetone/hexane (1:3) as colorless prisms; mp 200–201° C.; $^1$H NMR (CDCl$_3$): 1.04 (3H, t, J=7.4 Hz, CH$_3$), 1.23 (3H, d, J=7.0 Hz, CH$_3$), 1.33 (3H, d, J=6.5 Hz, CH$_3$), 1.51 (3H, s, CH$_3$), 1.54 (3H, s, CH$_3$), 1.67 (2H, sextet, J=7.4 Hz, CH$_2$), 2.82–3.01 (2H, m, CH$_2$), 3.79 (1H, dq, J=2.0 Hz, J=7.0 Hz, H$_{11}$), 4.46 (1H, dq, J=2.0 Hz, J=6.5 Hz, H$_{10}$), 5.57 (1H, d, J=9.9 Hz, H$_7$), 6.02 (1H, s, H$_3$), 6.67 (1H, d, J=9.9 Hz, H$_8$), 9.46 (1H, broad-s, OH); EIMS: 384 (12.9,M+1), 383 (49.22, M$^+$), 368 (100, M—CH$_3$), 366 (21.1, M—OH), 352 (15.2, M—NOH); IR (KBr) cm$^{-1}$: 3223 (broad, OH), 1740 (C=O); Anal. calcd. for $C_{22}H_{25}NO_5 \cdot \frac{1}{4}H_2O$: C, 68.11; H, 6.63; N, 3.61. Found: C, 68.40; H, 6.59; N, 3.58.

EXAMPLE 35

(±)-10,11-trans-10,11-Dihydro-4-propyl-6,6,10,11-tetramethyl-2H, 6H, 12H-benzo[1,2-b:3,4-b':5,6-b"]tripyran-2,12-dione-12-methoxime (Scheme VI, 19b, R$_1$=n-Pr, R$_2$=R$_4$=R$_7$=R$_8$H, R$_3$=R$_5$=R$_6$=R$_9$=Me, R$_{10}$=Me)

Into a one-necked 100 mL round-bottom flask was placed (±)-7 (1.47 g, 4.00 mmol) and NH$_2$OCH$_3$·HCl (1.67 g, 20.0 mmol). To this mixture was added methanol (60 mL), and the solution heated to reflux with magnetic stirring until the ketone dissolved. Solid $K_2CO_3$ powder (1.38 g, 10.0 mmol) was then careflilly added, and the reaction allowed to stir at reflux for 4 hours. The solution was cooled to room temperature, filtered to remove the $K_2CO_3$ and evaporated in vacuo, to provide a yellow oil. The residue was partitioned between 150 mL $H_2O$ and 150 mL ethyl acetate. The organic phase was collected and washed sequentially with 1 N HCl and saturated brine, then dried over magnesiun sulfate, filtered and evaporated to afford a thick yellow syrup. The product was purified a silica gel column chromatography (75 g), eluting with ethyl acetate/hexane (1:3) to afford the desired product as a faintly yellow oil which, upon standing, formed a white solid (598 mg, 38%). An analytical sample was obtained via recrystallization from acetone/hexane (1:3) as white plates; mp 143–144° C.; $^1$H NMR (CDCl$_3$): 1.01 (3H, t, J=7.3 Hz, CH$_3$), 1.16 (3H, d, J=7.0 Hz, CH$_3$), 1.28 (3H, d, J=6.4 Hz, CH$_3$), 1.49 (3H, s, CH$_3$), 1.50 (3H, s, CH$_3$), 1.64 (2H, sextet, J=7.3 Hz, CH$_2$), 2.79–2.99 (2H, m, CH$_2$), 3.57 (H, dq, J=1.9 Hz, J=7.0 Hz, H$_{11}$), 4.06 (3H, s, OCH$_3$), 4.37 (1H, dq, J=1.9 Hz, J=6.4 Hz, H$_{10}$), 5.54 (1H, d, J=10.0 Hz, H$_7$), 6.00 (1H, s, H$_3$), 6.62 (1H, d, J=10.0 Hz, H$_8$); EIMS: 397 (61.2, M$^+$), 382 (100, M—CH$_3$), 366 (12.9, M—OCH$_3$); IR (KBr) cm$^{-1}$: 1728 (vs, C=O); Anal. calcd. for $C_{23}H_{27}NO_5$: C, 69.50; H, 6.85; N, 3.52. Found: C, 69.39; H, 6.90; N, 3.59.

EXAMPLE 36

Conversion of (−)-Calanolide A into (−)-Calanolide B

To a solution of (−)-calanolide A (341 mg, 0.922 mmol) in anhydrous methylene chloride (5 mL) at −78° C. under $N_2$ was added a solution of diethylamidosulfur trifluoride (DAST, 178 mg, 1.11 mmol) in methylene chloride (1 ml) and the resulting yellow solution stirred at −78° C. for 4 hours. The reaction was quenched with 0.5 mL methanol, then allowed to warm to room temperature. The solution was diluted with methylene chloride (20 mL), then washed with water (50 mL) and saturated brine (50 mL). After drying over magnesium sulfate, the solution was filtered and evaporated to provide a light yellow solid. TLC analysis (silica gel, 3% methanol in methylene chloride) showed two components, one fast-moving and one slow. The material was chromatographed through 80 g silica gel, eluting with 1% methanol in $CH_2Cl_2$, and the fractions containing the respective components combined and evaporated to afford 198 mg (61% yield) of compound 22 and 75.3 mg (22%) of (−)-calanolide B.

10(S)-4-propyl-6,6,10,11-tetramethyl-2H,6H,10H-benzo[1,2-b:3,4b':5,6-b"]tripyran-2-one (22): $^1$H NMR (CDCl$_3$): 1.03 (3H, t, J=7.4 Hz, CH$_3$), 1.39 (3H, d, J=6.6 Hz, CH$_3$), 1.47 (3H, s, CH$_3$). 1.51 (3H, s, CH$_3$), 1.66 (2H, sextet, J=7.4 Hz, CH$_2$), 1.85 (3H, s, CH$_3$), 2.88 (2H, m, CH$_2$), 4.89 (1H, q, J=6.6 Hz, H$_{10}$), 5.55 (1H, d, J=10.0 Hz, H$_7$), 5.93 (1H, s, H$_3$), 6.62 (1H, d, J=10.0 Hz, H$_8$), 6.64 (1H, s, H$_{12}$); EIMS: 353 (15.5, M+1), 352 (53.2, M$^+$), 337 (100, M—CH$_3$). IR (KBr) cm$^{-1}$: 1724 (s, C=O); Anal. calcd. for $C_{22}H_{24}O_4$: C, 74.98; H, 6.86. Found: C, 74.87; H, 7.00.

(−)-Calanolide B: $^1$H NMR (CDCl$_3$): 1.03 (3H, t, J=7.3 Hz, CH$_3$), 1.14 (3H, d, J=7.0 Hz, CH$_3$), 1.43 (3H, d, J=6.4 Hz, CH$_3$), 1.48 (3H, s, CH$_3$), 1.49 (3H, CH$_3$), 1.66 (2H, sextet, J=7.6 Hz, CH$_2$), 1.72–1.79 (1H, m, H$_{11}$), 2.60 (1H, d, J=3.8 Hz, OH), 2.89 (2H, m, CH$_2$), 4.26 (1H, dq, J=10.7 Hz, 6.3 Hz, H$_{10}$), 4.97 (1H, J=3.8 Hz, H$_{12}$), 5.53 (1H, d, J=10.0 Hz, H$_7$), 5.95 (1H, s, H$_3$), 6.63 (1H, d, J=10.0 Hz, H$_8$); EIMS: 370 (31.1, M$^+$), 355 (100, M—CH$_3$), 299 (29.7, M—CH$_3$—C$_4$H$_8$); IR (KBr) cm$^{-1}$: 3478 (s, sharp, OH), 1703 (s, C=O).

EXAMPLE 37

Activity of (+)-Calanolide A against Tuberculosis

In the in vitro primary screening assay against *Mycobacterium tuberculosis* H37Rv in BACTEC 12B medium using the BACTEC 460 radiometric system,[44] both (+)- and (−)-calanolide A demonstrated 98% inhibition at a concentration of 12.5 µg/mL. (+)-Calanolide A was further tested at lower concentrations against *M. tuberculosis* H37Rv in CABTEC 460 to determine the actual minimum inhibitory concentration (MIC), the lowest concentration inhibiting 99% of the inoculum. It was found that (+)-calanolide A exhibited moderate anti-TB activity, with MIC value being 3.13 µg/mL (8.4 µM), comparing with the positive control drug rifampicin which had MIC value of 0.06 µg/mL.

EXAMPLE 38

In Vitro Evaluation of Calanolide Analogues

In the in vitro primary screening assay against *Mycobacterium tuberculosis* H37Rv in BACTEC 12B medium using the BACTEC 460 radiometric system,[44] FIG. 1 calanolide analogues (−)-soulattrolide, (−)-costatolide and (−)-7,8dihydrosoulattrolide demonstrated 99% inhibition at a concentration of 12.5 µg/mL. The Calanolide analogues were further tested at lower concentrations against *M. tuberculosis* H37Rv in CABTEC 460 to determine the actual minimum inhibitory concentration (MIC), the lowest concentration inhibiting 99% of the inoculum. It was found that the calanolide exhibited moderate anti-TB activity, compared with the positive control drug rifampicin which had MIC value of 0.06 μg/mL. Soulattrolide may be prepared using the procedures outline for (+)-calanolide A or extracted from natural sources. See Lin et al. *Pharmaceutical Biology* 1999, Vol. 37(1), pp. 71–76.

| Compound | MIC (μg/ml) | % Inhibition | Activity |
|---|---|---|---|
| Soulattrolide | <12.5 | 99 | + |
| Costatolide | <12.5 | 99 | + |
| (–)-7,8-Dihydrosoulatrolide | <12.5 | 99 | + |
| (–)-Trans-ketone | <12.5 | 78 | – |
| (±)-Trans-ketone | <12.5 | 59 | – |
| (±)-Cis-ketone | <12.5 | 57 | – |
| (±)-Trans-dihydroketone | <12.5 | 43 | – |

REFERENCES CITED

1. Lopez, A. in *Disease Control Priorties in Developing Countries*, Jamison, D. T., Mosely, W. H. Eds. (Oxford Univ. Press for the World Bank, New York, 1992), p.21

2. Murray, C. J. L., Stybio, K., Rouillon, A. in *Disease Control Priorties in Developing Countries*, Jamison, D. T., Mosely, W. H. Eds. (Oxford Univ. Press for the World Bank, New York, 1992), p.50; *Bull Int Union Tuberc.* 1990, 65, 24.

3. Raviglione, M. C., Snider, D. E., Koch, A. *JAM*, 1995, 273, 220.

4. Ozdemir, F. N., Buz, G., Kayatas, M. Sezer, S, arsian, H., Turan, N L *Transplantation Proceedings*, 1998, 30, 846.

5. Harries, A. D., Mahler, D. TB/HIV A Clinical Manual Published by the World Health Organization 1996, Printer: Stabilimento Tipografico Ferrero s.r.l.-Romano Canavese [TO], Italy.

6. Nivin, B., Nicholas, P., Gayer, M., Frieden, T. R., Fujiwara, P. I. *Clin. Infect. Dis.* 1998, 26,303.

7. Bernstein, J., Lott, W. A., Steinberg, B. A., Yale, H. L. *Am. Rev. Tuberc.* 1952, 65, 357.

8. Fix, H. H. *Science*, 1952, 116, 129.

9. Pansy, F., Stander, H., Donovick, R. *Am. Rev. Tuberc.* 1952, 63, 761.

10. Robitzek, E. H., Selikoff, I. F. *Am. Rev. Tuberc.* 1952, 65, 402.

11. a. *Wall Street Journal* (May 29, 1998).
    b. Petersen, Andrea *Wall Street Journal* (Jun. 24, 1998), pp. B5.

12. Mitchison, D. A. *J Antimicrob. Chemo.* 1992, 29, 477493.

13. Pablos-Mendez, A., Raviglione, M. C., Laszlo, A., Binkin, N. Rieder, H. L., Bustreo, F., Cohn, D. L., Lambregts-van Weezenbeek, C. S. B., Kim, S. J., Chaulet, P., Nunn, P. *New Eng. J Med.* 1998, 338, 1641.

14. Middlebrook, G. *Am. Rev. Tuberc.* 1952, 65, 765.

15. Johnsson, K., Schultz, P. G. *J. Am. Chem.* 1994, 116, 7425.

16. Zhang, Y., Heym, B., Allen, B., Young, D., Cole, S. *Nature* 1992, 358, 591.

17. Winder, Y., Collins, P. B. *J Gen. Microb.* 1970, 63, 41.

18. Winder, F. G. in Physiology, in *Identification, and Classification, of The Biology of the Mycobacteria* Vol I. Ratledge, C., Standford, J. Eds. (Academic Press, London, 1982)

19. Davison, L. A., Takayama, K., *Antimicrob. Agents Chemother.* 1979, 16, 104.

20. Levin M. E., Hatfull, G. F. Mycobacterium nsmegmatis RNA polymerase: DNA supercoiling, action of rifampicin and mechanism of rifampicin resistance. *Mol. Microbiol.* 1993, 8, 277.

21. Konno, K., Feldmann, F. M., McDermott, W. *Am. Rev. Respir. Dis.* 1967, 95,461.

22. a. Mitchison, D. A. *Nature Medicine* 1996, 2 (6), 635
    b. Scorpio and Zhang, *Nature Medicine* 1996, 2 (6), 662

23. Takayama, K., Armstrong, E. L., Kunigi, K. A., Kilburn, J. O. *Antimicrob. Agents Chemother.* 1979, 16, 240.

24. Morris, S., Bai, G. H., Suffys, P., Portillo-Gomez, L. Fairchock, M., Rouse, D. *J. Infec. Dis.* 1995, 171,954.

25. Musser, J. M., Kapur, V., Williams, D. L., Kreiswirth, B. N., van Embdan, J. D. A. *J Infect. Dis.* 1996, 173, 196.

26. Quemard, A., Sacchettini, J. C., Dessen, A., Vilecheze, C., Bittman, R., Jacob, Jr., W. R., Blanchard, J. S. *Biochemistry* 1995, 34, 8235.

27. Dessen A, Quemard A., Blanchard, J. S., Jacobs, Jr. W. R., Saccettini, J. C. *Science* 1995, 267, 1638.

28. Johnsson, K, King, D. S., Schyltz, P. G. *J. Am. Chem. Soc.* 1995, 117, 5009

29. Heym, B., Honore, N., Truffot-Pernot, C., Banerjee, A., Schurra, C., Jacobs Jr., W. R., Van Embden, J. D. A., Grosset, J. H., Cole, S. T. *Lancet* 1994, 344, 293.

30. Martila, H. J., Soini, H., Houovinen, P., Vijanen, M. K. *Antimicrob. Agents Chemother.* 1996, 40, 2187.

31. O'Brien, K. L., Dietz, H. C., Romalmoli, M., Eiden, J. *Mol. Cell. Probes* 1996, 10, 1.

32. Mdluli, K., Sherman, D. R., Hickey, M. J. Kreiswirth, B. N., Nirrusm S, M., Stover, C. K., Barry III, C. E. *J. Infect. Dis.* 1996, 174, 1085.

33. Mdluli, K., Slayden, R. A., Zhu, Y., Ramaswamy, S., Pan, X., Mead, D., Crane, D. D., Musser, J. M., Barry III, C. E. *Science*, 1998, 280, 1607.

34. Cole, S. T., Brosch, R., Parkhill, F., Garnire, T., Chrucher, C., Hzrris, D., Gordon, S. V., Elghmeler, K., Gas, S., Barry III, C. E., Tekala, F., Badcock, K., Basham, D., Brown, D., Chillingworth T., Connor, R., Davier, R., Devlin, K., Feltwell, T., Gentles, S., Hamlin, N., Holroyd, S., Hornsby, T., Jagels, K., Kroghss, A. McLean, J., Moule, S., Murphy, L., Oliver, K., Osborne, J., Quall, M. A., Rajandream, M.-A., Rogers, J., Rutter, S., Seeger, K., Skelton, K., Squares, R., Sulston, J. E., Taylor, K., Whitehead, S., Barrell, B. G. *Nature* 1998, 393, 537.

35. Herzog, H. *Respiration* 1998, 65, 5.

36. Perrins, J. H. et al. *Am. Rev. Respir. Dis.* 1991, 144, 750.

37. Snider, D. E., Roper, W. L., *New Engl. J. Med.* 1992, 326, 703.

38. Frieden, T. R. et al., *New Engl. J. Med.* 1993, 328, 521.

39. Ormerod, L. P. *Arch. Dis. Child* 1998, 78, 160.

40. Flavin, M. T., Rizzo, J. D., Khilevich, A., Kucherenko, A., Sheinkman, A. K., Vilaychack, V., Lin, L., Chen, W., Masta, E., Pengsuparp, T., Pezzuto, J. M., Hughes, S. H., Flavin, T. N., Cibulski, M., Boulanger, W. A., Shone, R. L., Xu, Z.-Q. *J. Med. Chem.* 1996,39, 1303.

41. Kucherenko, A., Flavin, M. T., Boulanger, W. A., Khilevich, A., Shone, R. L., Rizzo, J. D. Sheinkman, A. K., Zu, Z.-Q. *Tetrahedron Lett.* 1995, 36, 5475

42. Khilevich, A., Rizzo, J. K. Flavin, M. T., Sheinkinan, A. K., Mar, A., Kucherenko, A., Yan, C., Dzekhtser, S., Barnkovic, D., Lin, L., Liu, J., Rizzo, T. M., Xu, Z.-Q. *Synthetic Commun.* 1996, 20, 3757.

43. Khilevich, A., Mar, A., Flavin, M. T., Rizzo, J. D., Dzekhtser, S., Brankovic, D., Lin, L. Zhang, H., Chen, W., Liao, S., Zembower, D. E., Xu, Z.-Q. *Tetrahedron Asymmetry* 1996, 7,3315.

44. Frank, P., Flavin, M. T., Roca-Actin, J., Xu, Z.-Q. *4th Conference on Retroviruses and Opportunistic Infections*, Washington, D.C., Jan. 22–26, 1997, Abstract 225.

45. Creagh, T., Xu, Z.-Q., Ray, L. Giltner, J., Nayer, T., Ruckle, J 5th *Conference on Retroviruses and Opportunistic Infections,* Chicago, Feb. 1–5, 1998, Abstract 652.

46. Boyer, P. L., Currens, M. J., McMahon, J. B., Boyd, M. R., Hughes, S. H., *J. Virol.* 1993, 67, 2412.

47. Currens, M. J. Gulakowski, R. J., Mariner, J. M., Moran, R. A., Buckheit, R. W. Jr., Gustafson, K. R., McMahon, J. B., Boyd, M. R. *J. Pharmacol Exp. Ther.* 1996, 279, 645.

48. Inderleid, C. B., Nash, K. A. *Antibiotics in Laboratory Medicine* 4th ed. (Ed: Lorian, v. 1996) Williams and Wilkins, Baltimore, p. 127–175

49. Inderleid, C. B. and M. Salfinger. *Manual of Clinical Microbiology,* 6th ed. (Eds: Murray, P. R., Baron, E. J., Pfaller, M. A., Tenover, F. C. Yolken, R. H. 1995) ASM Press. Washington, D.C p.1385–1404.

51. Siddiqi, S. H. *Clinical Microbiology Procedures Handbook Vol. I.* (Ed: Isenberg, H D 1992) American Society for Microbiology, Washington, D.C. p. 5.14.2–5.14.25

52. Heifets, L. B. *Drug Susceptibility in the Chemotherapy of Mycobacterial Infections.* (Ed: Heifets, L. B. 1991) CRC Press, Boca Raton, p. 89–122.

53. Collins, L. S., Franzblau, S. G. Antimicrob. Agents and Chemother. 1997, 41:1004.

54. Cantrell, C. L., Lu, T. Fronczek, F. R., Fischer, N. H., Adams, L. B., Franzblau, S. G., *J. Nat. Prod.* 1996,59,1131

55. Kelley, B. P., Furney, S. K., Jessen, M. T., Orme, I. M.., *Antimicrob. Agents Chemother.* 1996, 40,2809.

56. Chenera, B.; West, M. L.; Finkelstein, J. A.; Dreyer, G. B., Total Synthesis of (±)-Calanolide A, a Non-Nucleoside Inhibitor of HIV-1 Reverse Transcriptase. *J. Org. Chem.* 1993, 58, 5605–5606.

57. Sethna, S.; Phadke, R., The Pechmann Reaction. *Org. React.,* 1953, 7, 1–58 and references cited therein.

58. a. Hughes, D. L., The Mitsunobu Reaction. *Org. React.,* 1992, 42, 335–656 and references cited therein.

b. Mitsunobu, O., The Use of Diethyl Azodicarboxylate and Triphenylphosphine in Synthesis and Transformation of Natural Products. *Synthesis,* 1981, 1–28.

c. Castro, B. R., Replacement of Alcoholic Hydroxyl Groups by Halogens and Other Nucleophiles via Oxyphosphonium Intermediates. *Org. React.* 1983,29, 1–162.

d. Hudlicky, M., Fluorination with Diethylaminosulfur Trifluoride and Related Aminofluorosulfanes. *Org. React.* 1988, 35, 513–637.

59. Gemal, A. L.; Luche, J. L., Lanthanoids in Organic Synthesis. 6. The Reduction of α-Enones by Sodium Borohydride in the Presence of Lanthanoid Chlorides: Synthetic and Mechanistic Aspects. *J. Am. Chem. Soc.,* 1981, 103, 5454–5459.

60. a Feuer, H.; Vincent, B. F., Jr.; Bartlett, R. S., The Reduction of Oximes with Diborane. A New Synthesis of N-Monosubstituted Hydroxylamines. *J. Org. Chem.,* 1965, 30, 2877–2880.

b. Feuer, H.; Braunstein, D. M., The Reduction of Oximes, Oxime Ethers, and Oxime Esters with Diborane. A Novel Synthesis of Amnines. *J. Org. Chem.,* 1969, 34, 1817–1821.

c. Borch, R. F.; Bernstein, M. D.; Durst, H. D., The Cyanohydridoborate Anion as a Selective Reducing Agent. *J. Amer. Chem. Soc.,* 1971, 93, 2897–2904.

61. For a review, see Nielsen, A. T.; Houlihan, W. J., The Aldol Condensation. *Org React.* 1968, 16, 1–438.

62. For reviews, see:

a. Mukaiyama, T., The Directed Aldol Reaction. *Org. React.* 1982, 28, 203–331.

b. Reetz, M. T., Chelation or Non-Chelation Control in Addition Reactions of Chiral α- and β-Alkoxy Carbonyl Compounds, *Angew. Chem. Int. Ed. Eng.* 1984, 23, 556–569.

c. Shibata, I.; Baba, A., Organotin Enolates in Organic Synthesis. *Org. Prep. Proc. Int.* 1994,26, 85–100.

63. For a review on chiral titanium complexes, see Duthaler, R. O.; Hafner, A., Chiral Titanium Complexes for Enantioselective Addition of Nucleophiles to Carbonyl Groups. *Chem. Rev.,* 1992, 92, 807–832 and reference cited therein.

64. For a review on chiral boron complexes, see Paterson, L.; Goodman, J. M.; M., Aldol Reactions in Polypropinonate Synthesis: High π-Face Selectivity of Enol Borinates from α-Chiral Methyl and Ethyl Ketones under Substrate Control. *Tetrahedron Lett.* 1989, 30, 7121–7124 and references cited therein.

65. Tsunoda, T.; Yamamiya, Y.; Kawamura, Y.; Ito, S., Mitsunobu Acylation of Sterically Congested Secondary Alcohols by N,N,N$^1$,N$^1$-Tetramethylazodicarboxamide-Tributylphosphie Reagents. *Tetrahedron Lett.* 1995, 36, 2529–2530.

66. Crombie, L.; Jones, R. C. F.; Palmer, C. J., Synthesis of the Mammea Coumarin. Part 1. The Coumarin of the Mammea A, B, and C Series. *J. Chem. Soc., Perkin Trans.* 1, 1987, 317–331.

67. Very recently, a similar work has been published in the literature; Cardellina, J. H., II; Bokesch, H. R.; McKee, T. C.; Boyd, M. R., Resolution and Comparative Anti-HIV Evaluation of the Enantiomers of Calanolides A and B. *Bioorg. Med. Chem. Lett.* 1995, 5, 1011–1014.

68. Deshpande, P. P., Tagliaferri, F.; Victory, S. F.; Yan, S.; Baker, D. C., Synthesis of Optically Active Calanolides A and B. *J Org. Chem.* 1995, 60, 2964–2965.

What is claimed is:

1. A method of preventing or treating a mycobacterium infection comprising administering to a mammal an effective amount of at least one compound of the formula I:

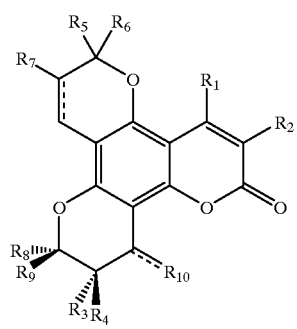

wherein $R_1$, is H, halogen, hydroxyl, amino, $C_{1-6}$ alkyl, aryl-$C_{1-6}$ alkyl, mono-or poly-fluorinated $C_{1-6}$ alkyl, hydroxy-$C_{1-6}$ alkyl, $C_{1-6}$ alkoxy, amino-$C_{1-8}$ alkyl, $C_{1-6}$ alkylamino, di($C_{1-6}$ alkyl)amino, $C_{1-8}$ alkylamino-$C_{1-8}$ alkyl, di($C_{1-6}$ alkyl) amino-$C_{1-8}$ alkyl, cyclohexyl, aryl, or heterocycle, wherein aryl or heterocycle is each optionally unsubstituted or substituted with one or more of the following: $C_{1-6}$ alkyl, $C_{1-6}$ alkoxy, hydroxy-$C_{1-4}$ alkyl, hydroxyl, amino, $C_{1-6}$ alkylamino, di($C_{1-6}$ alkyl) amino, amino-$C_{1-8}$ alkyl, $C_{1-8}$ alkylamino-$C_{1-8}$ alkyl, di($C_{1-6}$ alkyl)amino-$C_{1-8}$ alkyl, nitro, azido or halogen;

$R_2$ is H, halogen, hydroxyl, $C_{1-6}$ alkyl, aryl-$C_{1-6}$ alkyl, mono- or poly-fluorinated $C_{1-6}$ alkyl, aryl or heterocycle;

$R_3$ and $R_4$ are independently selected from the group consisting of H, halogen, hydroxyl, amino, $C_{1-6}$ alkyl, aryl-$C_{1-6}$alkyl, mono- or poly-fluorinated $C_{1-6}$alkyl, hydroxy-$C_{1-6}$ alkyl, amino-$C_{1-8}$ alkyl, $C_{1-8}$ alkylamino-$C_{1-8}$ alkyl, di($C_{1-6}$ alkyl)amino-$C_{1-8}$ alkyl, cyclohexyl, aryl or heterocycle; and $R_3$ and $R_4$ can be taken together to form a 5–7 membered saturated cycle ring or heterocyclic ring;

$R_5$ and $R_6$ are independently selected from the group consisting of H, $C_{1-6}$ alkyl, aryl-$C_{1-6}$ alkyl, mono- or poly-fluorinated $C_{1-6}$ alkyl, aryl or heterocycle; and $R_5$ and $R_6$ can be taken together to form a 5–7 membered saturated cycle ring or heterocycle ring;

$R_7$ is H, halogen, methyl, or ethyl;

$R_8$ and $R_9$ are independently selected from the group consisting of H, halogen, $C_{1-6}$ alkyl, aryl-$C_{1-6}$ alkyl, mono- or poly-fluorinated $C_{1-6}$ alkyl, hydroxy-$C_{1-6}$ alkyl, amino-$C_{1-8}$ alkyl, $C_{1-8}$ alkylamino-$C_{1-8}$ alkyl, di($C_{1-6}$ alkyl)amino-$C_{1-8}$ alkyl, cyclohexyl, aryl or heterocycle; and $R_8$ and $R_9$ can be taken together to form a 5–7 membered saturated cycle ring or heterocyclic ring;

$R_{10}$ is halogen, O, $OR_{11}$, $NOR_{,11}$, $NHOR_{11}$, $NOR_{12}$, $NHOR_{12}$, $NR_{11}R_{12}$, $NR12$, or $NR_{12}R_{13}$; wherein $R_{11}$ is H, acyl, $P(O)(OH)_2$, $S(O)(OH)_2$, $CO(C_{1-10}$ alkyl) $CO_2H$, ($C_{1-8}$ alkyl)$CO_2H$, $CO(C_{1-6}$ alkyl)$NR_{12}R_{13}$, ($C_{1-8}$ alkyl) $NR_{12}R_{13}$; $R_{12}$ and $R_{13}$ are independently selected from the group consisting of H, $C_{1-6}$ alkyl, aryl, and aryl-$C_{1-6}$ alkyl; and $R_{12}$ and $R_{13}$ can be taken together to form a 5–7 membered saturated heterocyclic ring containing said nitrogen; or a pharmaceutically acceptable salt thereof.

2. The method of claim 1, wherein the mycobacterium infection is selected from the group consisting of *Mycobacterium avium* complex (MAC), *Mycobacterium kansaii, Mycobacterium marinum, Mycobacterium phlei, Mycobacterium ulcerans, Mycobacterium xenopi, Mycobacterium gordonae, Mycobacterium terrae* complex, *Mycobacterium haemophilum, Mycobacterium fortuitum, Mycobacterium tuberculosis, Mycobacterium laprae, Mycobacterium scrofulaceum* and *Mycobacterium smegmatis*.

3. The method of claim 1, wherein the compound is selected from the group consisting of (+)-calanolide A, (−)-calanolide A, (±)-calanolide A, (−)-calanolide B, soulattrolide, and (−)-7,8-dihydrosoulattrolide.

4. The method of claim 1, which further comprises co-administering an effective therapeutic amount of at least one compound selected from the group consisting of an anti-microbial agent, an antiviral compound, an immunostimulant, an immunomodulator, an antibiotic, or a chemokine inhibitor.

5. The method of claim 4, wherein the anti-microbial agent is an anti-mycobacterial agent.

6. The method of claim 5, wherein the mycobacterial agent is an anti-TB agent.

7. The method of claim 6, wherein the anti-TB agent comprises isoniazid, rifampin, rifabutin, rifapentine, pyrazinamide or ethambutol.

8. The method of claim 4, wherein the antiviral compound is a protease inhibitor.

9. The method of claim 8, wherein the protease inhibitor is selected from the group consisting of indinavir, saquinavir, ritonavir, and nelfinavir.

10. The method of claim 4, wherein the antiviral compound is a biflavanoid.

11. The method of claim 10, wherein the biflavanoid is selected from the group consisting of robustaflavone, amentoflavone, and a derivative or salt thereof.

12. The method of claim 4, wherein the antiviral compound is selected from the group consisting of AZT, ddC, ddI, D4T, 3TC, acyclovir, gancyclovir, fluorinated nucleosides and nonnucleoside analog compounds.

13. The method of claim 4, wherein the immunostimulant is an interleukin or cytokine.

14. The method of claim 4, wherein the antibiotic is an antibacterial agent, antifungal agent, or anti-pneumocysitis agent.

15. The method of claim 12, wherein the nonnucleoside analog compound is selected from the group consisting of delavirdine, nevirapine, efavirenz, α-interferon, recombinant CD4, amantadine, rimantadine, ribavirin and vidarabine.

16. A method of preventing or treating a tuberculosis infection in a mammal comprising administering to said mammal an effective anti-tuberculosis infection amount of a compound selected from the group consisting of (+)calanolide A, (−)-calanolide A, (−)-soulattrolide, (−)-costatolide and (−)-7,8-dihydrosoulattrolide.

17. The method of claim 16 further comprising an antiviral compound selected from the group consisting of AZT, ddC, ddI, D4T, 3TC, acyclovir, gancyclovir, fluorinated nucleosides and nonnucleoside analog compounds.

18. The method of claim 17, wherein the nonnucleoside analog compound is selected from the group consisting of delavirdine, nevirapine, efavirenz, α-interferon, recombinant CD4, amantadine, rimantadine, ribavirin and vidarabine.

* * * * *